(12) United States Patent
Crawford et al.

(10) Patent No.: US 8,574,567 B2
(45) Date of Patent: *Nov. 5, 2013

(54) MULTIPOTENT STEM CELLS AND USES THEREOF

(75) Inventors: Keith D. Crawford, Westwood, MA (US); Chris Southgate, Sudbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/890,195

(22) Filed: Sep. 24, 2010

(65) Prior Publication Data

US 2011/0070205 A1    Mar. 24, 2011

Related U.S. Application Data

(63) Continuation-in-part of application No. 12/598,047, filed as application No. PCT/US2008/005742 on May 5, 2008.

(60) Provisional application No. 60/927,596, filed on May 3, 2007, provisional application No. 61/247,242, filed on Sep. 30, 2009, provisional application No. 61/249,172, filed on Oct. 6, 2009.

(51) Int. Cl.
    *C12N 5/00*    (2006.01)

(52) U.S. Cl.
    USPC ........................................ 424/93.7; 435/325

(58) Field of Classification Search
    None
    See application file for complete search history.

(56) References Cited

U.S. PATENT DOCUMENTS

| | | | |
|---|---|---|---|
| 4,714,680 A | 12/1987 | Civin | |
| 5,035,994 A | 7/1991 | Civin | |
| 5,061,620 A | 10/1991 | Tsukamoto et al. | |
| 5,130,144 A | 7/1992 | Civin | |
| 5,256,560 A | 10/1993 | Lawman et al. | |
| 5,306,624 A * | 4/1994 | Roelant | 435/39 |
| 5,409,813 A | 4/1995 | Schwartz et al. | |
| 5,429,938 A | 7/1995 | Humes | |
| 5,486,359 A | 1/1996 | Caplan et al. | |
| 5,591,625 A | 1/1997 | Gerson et al. | |
| 5,599,705 A | 2/1997 | Cameron | |
| 5,605,829 A | 2/1997 | McGlave et al. | |
| 5,635,387 A | 6/1997 | Fei et al. | |
| 5,643,741 A | 7/1997 | Tsukamoto et al. | |
| 5,654,183 A | 8/1997 | Anderson et al. | |
| 5,658,564 A | 8/1997 | Sykes et al. | |
| 5,677,136 A | 10/1997 | Simmons | |
| 5,733,541 A | 3/1998 | Taichman et al. | |
| 5,750,376 A | 5/1998 | Weiss et al. | |
| 5,750,397 A | 5/1998 | Tsukamoto et al. | |
| 5,753,506 A | 5/1998 | Johe | |
| 5,766,944 A | 6/1998 | Ruiz | |
| 5,772,994 A | 6/1998 | Ildstead et al. | |
| 5,811,301 A | 9/1998 | Cameron | |
| 5,827,742 A | 10/1998 | Scadden | |
| 5,834,308 A | 11/1998 | Peck et al. | |
| 5,840,580 A | 11/1998 | Terstappen et al. | |
| 5,851,832 A | 12/1998 | Weiss et al. | |
| 5,861,315 A | 1/1999 | Nakahata | |
| 5,876,708 A | 3/1999 | Sachs | |
| 5,906,940 A | 5/1999 | Wandrey et al. | |
| 5,916,553 A | 6/1999 | Schmidt | |
| 6,001,647 A | 12/1999 | Peck et al. | |
| 6,006,752 A | 12/1999 | Sykes et al. | |
| 6,043,066 A | 3/2000 | Mangano | |
| 6,071,889 A | 6/2000 | Weiss et al. | |
| 6,093,531 A | 7/2000 | Bjornson et al. | |
| 6,129,911 A | 10/2000 | Faris | |
| 6,207,451 B1 | 3/2001 | Dennis et al. | |
| 6,214,369 B1 | 4/2001 | Grande et al. | |
| 6,228,640 B1 | 5/2001 | Cezayirli et al. | |
| 6,251,665 B1 | 6/2001 | Cezayirli et al. | |
| 6,331,403 B1 | 12/2001 | Potempa et al. | |
| 6,395,546 B1 | 5/2002 | Zobel et al. | |

(Continued)

FOREIGN PATENT DOCUMENTS

EP     1 845 154 A1    10/2007
WO     WO 01/11011 A2    2/2001

(Continued)

OTHER PUBLICATIONS

Lee et al., Blood, 103:1669-1675 (2004). "Isolation of multipotent mesenchymal stem cells from umbilical cord blood."
Schrepfer et al., Transplant Proc, 39:573-576 (2007). "Stem cell transplantation: the lung barrier."
Drukker et al., PNAS, 99(15):9864-9869 (2002). "Characterization of the expression of MHC proteins in human embryonic stem cells."

(Continued)

*Primary Examiner* — Lora E Barnhart Driscoll
(74) *Attorney, Agent, or Firm* — Mark J. Fitzgerald; Nixon Peabody LLP

(57) ABSTRACT

The invention provides a quiescent stem cell having the capacity to differentiate into ectoderm, mesoderm and endoderm, and which does not express cell surface markers including MHC class I, MHC class II, CD44, CD45, CD13, CD34, CD49c, CD73, CD105 CD90, CD66A, CD66E, CXCR4, CD133 or an SSEA. The invention further provides a proliferative stem cell, which expresses genes including Oct-4, Nanog, Sox2, GDF3, P16INK4, BMI, Notch, HDAC4, TERT, Rex-1, TWIST, KLF-4 and Stella but does not express cell surface markers including MHC class I, MHC class II, CD44, CD45, CD13, CD34, CD49c, CD73, CD105, CD90, CD66A, CD66E, CXCR4, CD133 or an SSEA. The cells of the invention can be isolated from adult mammals, have embryonic cell characteristics, and can form embryoid bodies. Methods for obtaining the stem cells, as well as methods of treating diseases and differentiated the stem cells, are also provided.

19 Claims, 30 Drawing Sheets

(56) References Cited

U.S. PATENT DOCUMENTS

| | | |
|---|---|---|
| 6,399,369 B1 | 6/2002 | Weiss et al. |
| 6,448,075 B1 | 9/2002 | Thomas |
| 6,497,872 B1 | 12/2002 | Weiss et al. |
| 6,497,876 B1 | 12/2002 | Maraskovsky et al. |
| 6,555,374 B1 | 4/2003 | Gimble et al. |
| 6,593,372 B2 | 7/2003 | Enikolopov et al. |
| 6,596,274 B1 | 7/2003 | Abatangelo et al. |
| 6,638,763 B1 | 10/2003 | Steindler et al. |
| 6,699,471 B2 | 3/2004 | Radice et al. |
| 6,709,864 B1 | 3/2004 | Pittenger et al. |
| 6,713,065 B2 | 3/2004 | Baron et al. |
| 6,761,887 B1 | 7/2004 | Kavalkovich et al. |
| 6,767,738 B1 | 7/2004 | Gage et al. |
| 6,777,234 B1 | 8/2004 | Dennis et al. |
| 6,805,860 B1 | 10/2004 | Alt |
| 6,824,973 B2 | 11/2004 | Tang et al. |
| 6,828,145 B2 | 12/2004 | Avital et al. |
| 6,844,312 B2 | 1/2005 | Weiss et al. |
| 6,872,389 B1 | 3/2005 | Faris |
| 6,902,932 B2 | 6/2005 | Altman et al. |
| 6,911,201 B1 | 6/2005 | Merchav et al. |
| 6,911,220 B1 | 6/2005 | Sachs |
| 6,929,948 B1 | 8/2005 | Smith et al. |
| 6,936,281 B2 | 8/2005 | Seshi |
| 6,972,195 B2 | 12/2005 | Xu |
| 6,989,030 B1 | 1/2006 | Ohgushi |
| 7,029,915 B2 | 4/2006 | Yang |
| 7,048,934 B2 | 5/2006 | Thompson et al. |
| 7,052,907 B2 | 5/2006 | Shi et al. |
| 7,056,738 B2 | 6/2006 | Prockop et al. |
| 7,060,494 B2 | 6/2006 | Bhat |
| 7,067,118 B2 | 6/2006 | Graddis et al. |
| 7,078,232 B2 | 7/2006 | Konkle et al. |
| 7,115,418 B2 | 10/2006 | Weiss et al. |
| 7,132,286 B2 | 11/2006 | Laeng et al. |
| 7,132,287 B2 | 11/2006 | Rajan et al. |
| 7,150,989 B2 | 12/2006 | Goldman et al. |
| 7,157,080 B2 | 1/2007 | Radice et al. |
| 7,160,725 B2 | 1/2007 | Warzecha |
| 7,166,277 B1 | 1/2007 | Weiss et al. |
| 7,166,280 B2 | 1/2007 | Franco |
| 7,186,558 B2 | 3/2007 | Aberdam et al. |
| 7,192,769 B2 | 3/2007 | Pykett et al. |
| 7,204,979 B2 | 4/2007 | Bjornson et al. |
| 7,217,570 B2 | 5/2007 | Herlyn et al. |
| 7,259,011 B2 | 8/2007 | Lucas et al. |
| 7,282,222 B2 | 10/2007 | Phillips |
| 7,297,540 B2 | 11/2007 | Mitrani |
| 7,311,905 B2 | 12/2007 | Hariri |
| 7,341,062 B2 | 3/2008 | Chachques et al. |
| 7,361,505 B1 | 4/2008 | Weiss et al. |
| 7,374,937 B1 | 5/2008 | Prockop et al. |
| 7,375,077 B2 | 5/2008 | Mao |
| 7,384,784 B2 | 6/2008 | Rudnicki et al. |
| 7,390,484 B2 | 6/2008 | Fraser et al. |
| 7,410,797 B2 | 8/2008 | Ogle et al. |
| 7,422,736 B2 | 9/2008 | Hwang |
| 7,429,488 B2 | 9/2008 | Fraser et al. |
| 7,438,902 B2 | 10/2008 | Habener et al. |
| 7,452,532 B2 | 11/2008 | Alt |
| 7,462,483 B2 | 12/2008 | Scadden et al. |
| 7,473,420 B2 | 1/2009 | Fraser et al. |
| 7,494,644 B2 | 2/2009 | Lee |
| 7,498,168 B2 | 3/2009 | Sharpe |
| 7,501,115 B2 | 3/2009 | Fraser et al. |
| 7,504,099 B2 | 3/2009 | Gazit et al. |
| 7,504,100 B2 | 3/2009 | Yu et al. |
| 7,514,075 B2 | 4/2009 | Hedrick et al. |
| 7,521,231 B2 | 4/2009 | Germain et al. |
| 7,524,492 B2 | 4/2009 | Sharma |
| 7,524,493 B2 | 4/2009 | Flugelman et al. |
| 7,534,609 B2 | 5/2009 | Merchav et al. |
| 7,534,765 B2 | 5/2009 | Gregg et al. |
| 7,537,756 B2 | 5/2009 | Habener et al. |
| 7,541,183 B2 | 6/2009 | Rudnicki et al. |
| 7,544,509 B2 | 6/2009 | Toma et al. |
| 7,544,511 B2 | 6/2009 | Yang et al. |
| 7,547,674 B2 | 6/2009 | Anversa et al. |
| 7,585,670 B2 | 9/2009 | Hedrick et al. |
| 7,588,936 B2 | 9/2009 | Sharpe |
| 7,595,043 B2 | 9/2009 | Hedrick et al. |
| 7,601,344 B2 | 10/2009 | Kanno |
| 7,604,990 B2 | 10/2009 | Pebay et al. |
| 7,604,993 B2 | 10/2009 | Thompson et al. |
| 7,611,895 B2 | 11/2009 | Tan et al. |
| 7,618,621 B2 | 11/2009 | Sugaya et al. |
| 7,622,108 B2 | 11/2009 | Collins et al. |
| 7,635,467 B2 | 12/2009 | Sugaya et al. |
| 7,651,684 B2 | 1/2010 | Hedrick et al. |
| 7,655,224 B2 | 2/2010 | Snyder et al. |
| 7,659,121 B2 | 2/2010 | Endo et al. |
| 7,670,596 B2 | 3/2010 | Collins et al. |
| 7,687,059 B2 | 3/2010 | Fraser et al. |
| 7,709,442 B2 | 5/2010 | Mao |
| 7,723,105 B2 | 5/2010 | Bordoni et al. |
| 7,727,762 B2 | 6/2010 | Fukuda |
| 7,745,113 B2 | 6/2010 | Evans et al. |
| 7,754,486 B2 | 7/2010 | Pasquet-Vallejo |
| 7,767,202 B2 | 8/2010 | Pardoll et al. |
| 7,771,716 B2 | 8/2010 | Hedrick et al. |
| 7,776,586 B2 | 8/2010 | Cregan et al. |
| 7,776,592 B2 | 8/2010 | Wandinger-Ness et al. |
| 7,790,456 B2 | 9/2010 | Terstegge et al. |
| 7,795,025 B2 | 9/2010 | Klimanskaya et al. |
| 7,795,031 B2 | 9/2010 | Demeneix et al. |
| 7,803,364 B2 | 9/2010 | Trapp et al. |
| 7,807,461 B2 | 10/2010 | Kang et al. |
| 7,807,462 B2 | 10/2010 | Rameshwar |
| 7,811,822 B2 | 10/2010 | Lindquist et al. |
| 7,816,140 B2 | 10/2010 | Lau et al. |
| 7,838,290 B2 | 11/2010 | Friedlander et al. |
| 7,846,467 B2 | 12/2010 | Coroneo |
| 7,846,898 B2 | 12/2010 | Weiss et al. |
| 7,850,960 B2 | 12/2010 | Moon et al. |
| 7,862,810 B2 | 1/2011 | Anversa |
| 7,875,273 B2 | 1/2011 | Messina et al. |
| 7,892,534 B2 | 2/2011 | Lee et al. |
| 7,892,829 B2 | 2/2011 | Pittenger et al. |
| 7,892,835 B2 | 2/2011 | Akaike et al. |
| 7,897,588 B2 | 3/2011 | Parhami |
| 7,901,936 B2 | 3/2011 | Temple et al. |
| 7,906,110 B2 | 3/2011 | Chancellor et al. |
| 7,906,330 B2 | 3/2011 | Thies |
| 7,914,779 B2 | 3/2011 | Hariri |
| 7,918,854 B2 | 4/2011 | Schwartz |
| 7,927,785 B2 | 4/2011 | Milhem et al. |
| 7,928,068 B2 | 4/2011 | Liu et al. |
| 7,932,084 B2 | 4/2011 | Katz et al. |
| 7,939,057 B2 | 5/2011 | Battista et al. |
| 7,939,059 B2 | 5/2011 | Yang et al. |
| 7,951,592 B2 | 5/2011 | Chen et al. |
| 7,955,846 B2 | 6/2011 | Tilly et al. |
| 7,955,850 B2 | 6/2011 | Carinci et al. |
| 7,955,852 B2 | 6/2011 | Peled et al. |
| 7,976,836 B2 | 7/2011 | Hariri |
| 7,985,586 B2 | 7/2011 | Bieberich et al. |
| 7,994,131 B2 | 8/2011 | Tucker |
| 7,994,144 B2 | 8/2011 | Symonds et al. |
| 7,998,472 B2 | 8/2011 | Huss et al. |
| 2002/0127715 A1 | 9/2002 | Benvenisty et al. |
| 2004/0107453 A1* | 6/2004 | Furcht et al. .................. 800/18 |
| 2005/0042595 A1* | 2/2005 | Haas ................................ 435/2 |
| 2005/0089513 A1 | 4/2005 | Sakuragawa et al. |
| 2005/0234013 A1* | 10/2005 | Parsons .......................... 514/54 |
| 2005/0255588 A1 | 11/2005 | Young et al. |
| 2006/0211109 A1 | 9/2006 | Totey et al. |
| 2007/0042491 A1 | 2/2007 | Karp et al. |
| 2010/0291042 A1 | 11/2010 | Crawford et al. |

FOREIGN PATENT DOCUMENTS

| | | |
|---|---|---|
| WO | 2005/001076 A2 | 1/2005 |
| WO | WO 2005/017117 A | 2/2005 |
| WO | WO 2007/064090 A1 | 6/2007 |

(56) References Cited

FOREIGN PATENT DOCUMENTS

| WO | 2008036374 A2 | 3/2008 |
|---|---|---|
| WO | 2008/137115 | 11/2008 |
| WO | 2009032456 A2 | 3/2009 |
| WO | 2009092092 A1 | 7/2009 |

OTHER PUBLICATIONS

Kogler et al., J Exp Med, 200(2):123-135 (2004). "A new human somatic stem cell from placental cord blood with intrinsic pluripotent differentiation potential."
Parolini et al., Stem Cells, 26:300-311 (2008). "Concise review: Isolation and characterization of cells from human term placenta: Outcome of the first international workshop on placenta derived stem cells."
Fukada et al., Stem Cells, 25(10):2448-59 (2007). "Molecular signature of quiescent satellite cells in adult skeletal muscle".
Ratajczak et al., Stem Cell Rev, 4:89-99 (2008). "Very small embryonic-like (VSEL) stem cells: purification from adult organs, characterization, and biological significance."
Crawford, K. et al., "Identification of Dendritic Cells and Mesenchymal Stem Cells in the Synovial Fluid of Osteoarthritic Patients", ORS Poster, San Diego, CA, Feb. 11, 2007-Feb. 14, 2007, Poster No. 0446.
PCT/ISA/210, WO, Aug. 6, 2008.
PCT/ISA/237, WO, Aug. 6, 2008.
EPO Form 1507S, EP, Jun. 7, 2010.
Bartholomew A., et al; Mesenchymal stem cells suppress lymphocyte proliferation in vitro and prolong skin graft survival in vivo. Exp. Hematol. 2002;30:42-48.
Dinicola M., et al.; Human bone marrow stromal cells suppress T-lymphocyte proliferation induced by cellular or nonspecific mitoogenicstimuli. Blood. 2002;99:3838-3843.
Krampera M. et al.; Bone marrow mesenchymal stem cells inhibit the response of naive and memory antigen-specific T cells to their cognate peptide. Blood. 2003;101:3722-3729.
Jiang XX, et al.; Human mesenchymal stem cells inhibit differentiation and function of monocyte-derived dendritio cells; Blood. May 15, 2005; 105(10): 4120-6. Epub Feb. 3, 2005.
Zeng (2006) Stem Cells. Nov. 2006;24(11):2355-66. Epub Aug. 24.
Reyes (2001, retracted) Blood Nov. 1;98(9):2615-25.
Aranguren et al. (2007) Blood vol. 109, No. 6, pp. 2634-2642.
Ross et al. (2007) J. Clin. Invest. July;117(7):2014.
Carlin (2006) Reprod Biol Endocrinol. Feb. 6;4:8.
Zou et al. (2009) Nature Cell Biology, published online Apr. 12, 2009; DOI 10.1038/ncb1869.
Hua J. et al. (2009) Reprod Biomed Online. Jul;19(1):99-105.
Drusenheimer N. (2007) Soc Reprod Fertil Suppl. 63:69-76.
Nayernia K (2006) Lab Invest. Jul;86(7):654-63. Epub May 1.
Kucia M. (2006) Leukemia Feb. 20: 857-869.
De Coppi P. (2007) Nature Biotechnology. vol. 25, No. 1, 100-106.
Jiang Y. (2002) Nature. vol. 418, 41-49.
Kucia M. (2005) Leukemia 19. May: 1118-1127.
Rogers I. (2007) Science Direct. Experimental Cell Research 313: 1839-1852.
Ringe J. (2008) Journal of Tissue Engineering and Regenerative Medicine; 2: 136-146.
Ratajczk et al. A hypothesis for an embryonic origin of pluripotent Oct-4 positive stem cells in adult bone marrow and other tissues. IN: Leukemia. Mar. 8, 2007. vol. 21 No. 5 p. 860-867.
Kucia et al. Morphological and molecular characterization of novel population of CXCR4 positive SSEA-4 positive Oct-4 positive very small embryonic-like cells ;purified from human cord blood preliminary report. IN: Leukemia. Feb. 2007 vol. 21 No. 2 p. 297-303.
Stemcell Technologies. RosetteSep: Human Granulocyte Depletion. 2006. Available online at www.stemcell.com/product_catalog/product_catalog_index.aspxtype=catalog_item&id=496. p. 1.
D'ippolito G. et al., Marrow-isolated adult multilineage inducible (MIAMI) cells, a unique population of postnatal young and old human cells with extensive expansion and differentiation potential. Journal of Cell Science, Cambridge University Press, London, GB LNKD-DOI: 10.1242/JCS. 01103, vol. 117, No. 14, Jun. 15, 2004, pp. 2971-2981.
Matikainen et al. Placenta—an alternative source of stem cells. Toxicology and Applied Pharmacology, Academic Press, US LNKD-DOI: 10.1016/J. TAAP, 2005.01.039, vol. 207, No. 2, pp. 544-549.
Verfaillie C. M. Adult stem cells: assessing the case for pluripotency. Trends in Cell Biology, Elsevier Science, Ltd. ZXX LNKD-DOI: 10.1016/S0962-8924(02)02386-3, vol. 12, No. 11, Nov. 1, 2002, pp. 502-508.
Sakaguchi Yusuke et al. Comparison of human stem cells derived from various mesenchymal tissues—Superiority of synovium as a cell source. Arthritis & Rheumatism, vol. 52, No. 8, Aug. 2005, pp. 2521-2529.
Londolfo Da Silva Meirelles et al. Mesenchymal stem cells reside in virtually all post-natal organs and tissues. Journal of Cell Science, Cambridge University Press, London, GB LNKD-DOI: 10.1242/JCS.02932, vol. 119, No. 11, Jun. 1, 2006, pp. 2204-2213.
Stemcall Technologies 2. Identification of Viable Stem and Progenitor Cells with Aldefluor Technical Bulletin 2004. Available on the internet at <URL: http://www.stemcell.com/technical/12_aldefluor.pdf>. p. 1, Assay Principle and Fig 2.
Attarian et al. Long-term cryopreservation of bone marrow for autologous transplantation. IN:Bone Marrow Transplant. Mar. 1996 vol. 17 No. 3 p. 425-430> abstract only.
Cottler-Fox et al. Stem Cell Mobilization. IN: Hematology AM Soc Hematol Educ Program Book, 2003 vol. 1 p. 419-37, abstract only.
Lange et al. Hepatocytic gene expression in cultured rat mesenchymal stem cells. IN: Transplant Proc. Jan.-Feb. 2005 vol. 37 No. 1 p. 276-279. Abstract only.
Reyes et al. Origin of endothelial progenitors in human postnatal bone marrow. IN: J Clin Invest. Feb. 2002 vol. 109 No. 3 p. 337-46. Abstract only.
Oric Stem cell repair in ischemic hear disease: an experimental model IN: Int J Hematol. Aug. 2002 vol. 76 Suppl 1 p. 144-145. Abstract only.
Fu et al. Enhanced wound-healing quality with bone marrow mesenchymal stem cells autografting after skin injury. IN: Wound Repair Regen. May Jun. 2006 vol. 14, No. p. 325-335. Abstract only.
Chadwick et al Cyoknes and BMP-4 promote hemaopoietc diferentaton of human embryonic stem cells. IN: Blood Aug. 1, 2003 vol. 102 No. 3 p. 906-915, especially p. 907 left col Material and Methods.
Traynor et al. Treatment of severe systemic lupus erythematosus with high-dose chemotherapy and haemopoietic stem-cell transplantation: a phase 1 study. IN: Lancet. Aug. 26, 2000. vol. 356 No. 9231 p. 701-707. Abstract only.
Peck et al. Generation of islets of Langerhans from adult pancreatic stem cells. IN. J Hepatobillary Pancreat Sur. Jun. 2002 vol. 9 No. 6 p. 707-709. Abstract only.
Wada et al. Generation of different fates from multipotent muscle stem cells. IN: Development Jun. 2002. vol. 197 No. 12 p. 2987-2995. Especially abstract and p. 2987 left col para 1.
Fukuda et al. Purification and cell-surface marker characterization of quiescent satellite cells from murine skeletal muscle by a novel monoclonal antibody. IN: Experimental Cell Research, Jun. 10, 2004. vol. 296. No. 2 p. 245-255. Abstract only.
Robin Lovell-Badge, Banking on spermatogonial stem cells: Frozen assets and foreign investments, Nature Medicine, vol. 2, No. 6, Jun. 1996, pp. 638-639.
Meachem, Sarah et al., Spermatogonia: stem cells with a great perspective. Reproduction (2001) 121, 825-834.
Nisal, Manuel et al., Decrease in the Number of Human Ap and Ad Spermatogonia and in the Ap/Ad Ratio with Advancing Age. J Androl 1987; 8:64-68.
Pacchiarotti, J. et al. Differentiation potential of germ line stem cells derived from the postnatal mouse ovary. Differentiation (2010), doi:10.1016/j.diff.2010.01.001.
Paniagua, Ricardo et al., Quantification of cell types throughout the cycle of the human seminiferous epithelium and their DNA content. Anat Embryol (1987) 176:225-230.

(56) References Cited

OTHER PUBLICATIONS

Schulze, Cornelia. Response of the human testis to long-term estrogen treatment: Morphology of Sertoli cells, Leydig cells and spermatogonial stem cells. Cell Tissue Res (1988) 251:31-43.

Johnson, Joshua et al. Germline stem cells and follicular renewal in the postnatal mammalian ovary. Nature, vol. 428, Mar. 11, 2004, pp. 145-150.

Byskov, Anne Grete et al. Eggs forever? Differentiation (2005) 73:438-466.

Arpinati et al., Transplant Immunology, 11:345-356 (2003). "Role of plasmacytoid dendritic cells in immunity and tolerance after allogeneic hematopoietic stem cell transplantation."

Colter et al., PNAS, 97(7):3213-3218 (2000). "Rapid expansion of recycling stem cells in cultures of plastic-adherent cells from human bone marrow."

Colter et al., PNAS, 98(14):7841-7845 (2001). "Identification of a subpopulation of rapidly self-renewing and multipotential adult stem cells in colonies of human marrow stromal cells."

Haasters et al., J. Anat., 214:759-767 (2009). "Morphological and immunocytochemical characteristics indicate the yield of early progenitors and represent a quality control for human mesenchymal stem cell culturing."

The International Stem Cell Initiative (Adewumi et al.), Nature Biotechnology, 25(7):803-816 (2007). "Characterization of human embryonic stem cell lines by the International Stem Cell Initiative."

Izadpanah et al., J. Cell Biochem, 99(5):1285-1297 (2006). "Biologic properties of mesenchymal stem cells derived from bone marrow and adipose tissue."

Jones et al., Arthritis & Rheumatism, 50(3):817-827 (2004). "Enumeration and Phenotypic Characterization of Synovial Fluid Multipotential Mesenchymal Progenitor Cells in Inflammatory and Degenerative Arthritis."

Kobayashi et al., Cell Transplantation, 17:291-301 (2008). "Multilineage Potential of Side Population Cells From Human Amnion Mesenchymal Layer."

Lin et al., Biochem Biophys Res Commun, 355(1):111-116 (2007). "Stem cell regulatory function mediated by expression of a novel mouse Oct4 pseudogene."

Pain et al., The Journal of Biological Chemistry, 280(8):6265-6268 (2005). "Multiple Retropseudogenes from Pluripotent Cell-specific Gene Expression Indicates a Potential Signature for Novel Gene Identification."

Palmqvist et al., Stem Cells, 23:663-680 (2005). "Correlation of Murine Embryonic Stem Cell Gene Expression Profiles with Functional Measures of Pluripotency."

Pochampally et al., Blood, 103:1647-1652 (2004). "Serum deprivation of human marrow stromal cells (hMSCs) selects for a subpopulation of early progenitor cells with enhanced expression of OCT-4 and other embryonic genes."

Prockop et al., Cytotherapy, 3(5):393-396 (2001). "Isolation and characterization of rapidly self-renewing stem cells from cultures of human marrow stromal cells."

Ruggeri et al., Science, 295:2097-2100 (2002). "Effectiveness of Donor Natural Killer Cell Alloreactivity in Mismatched Hematopoietic Transplants."

Sekiya et al., Biochemical and Biophysical Research Communications, 284:411-418 (2001). "BMP-6 Enhances Chondrogenesis in a Subpopulation of Human Marrow Stromal Cells."

Tao et al., Chinese Journal of Medical Genetics, 17(5):352-354, English Abstract only (2000). "The application of CD71 and Hoechst33258 to staining method for sorting fetal nucleated red blood cells in the peripheral blood of pregnant women."

Yau et al., Exp. Hematol., 18:219-222 (1990). "Purging of T-lymphocytes with Magnetic Affinity Colloid."

* cited by examiner

Forward and Side Scatter of Synovial Fluid Mononuclear Cells

Comparison of Class-I and CD44 Expression in Groups A, B, and C

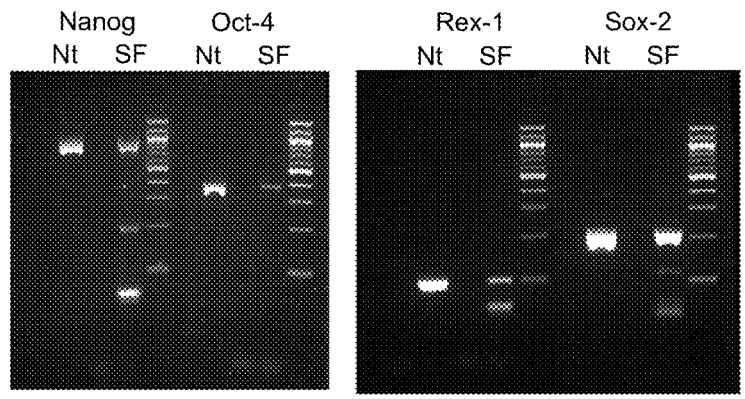
Nt: Ntera-2 embryonic carcinoma cell line; SF: OA synovial fluid
Expression of embryonic stem cell genes(Nanog, Oct-4, Rex-1, and Sox-2)
FIG. 2
Day 0
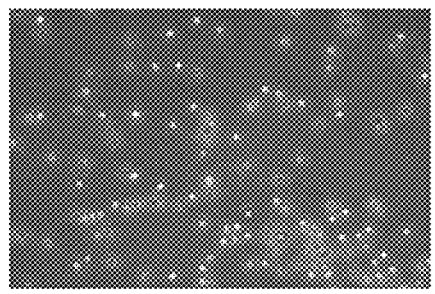
Quiescence
Day 3
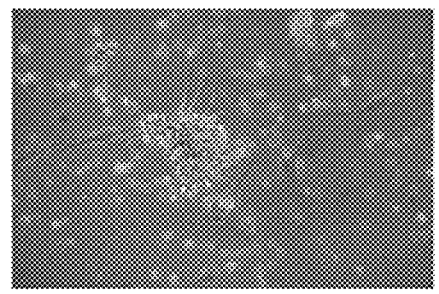
Aggregate
*Day 6
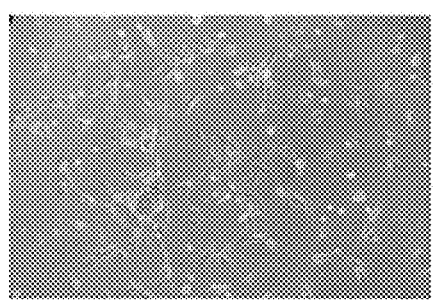
Proliferative
*Day 9
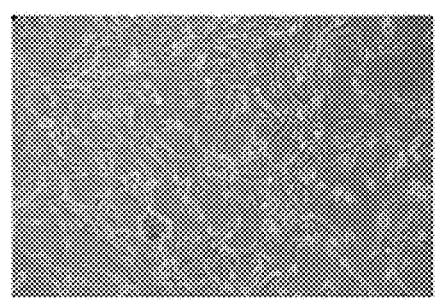
Proliferative
*Days 6 and 9 are at a lower magnification of the day 3 image
Expansion of Undifferentiated JEMS
FIG. 3A Differentiation of JEMS into Osteoblast, Adipocytes, and Neuron Differentiated JEMS Express Osteoblast- or Adipocyte-specific Genes Internal Cell Staining: Demonstration of Oct 4
Protein Expression in JEMS

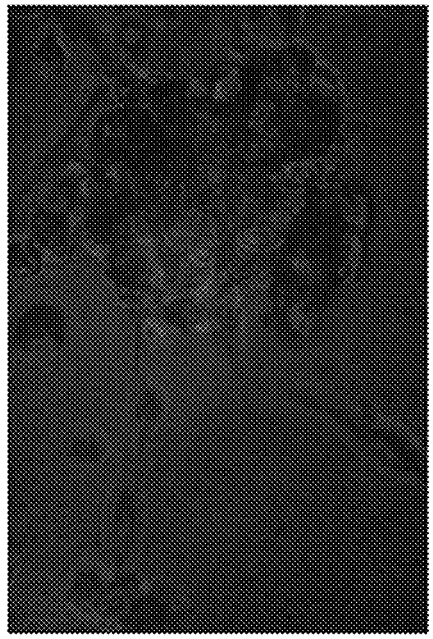
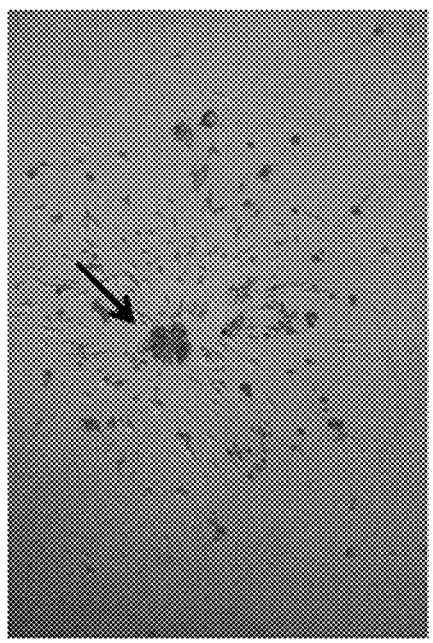
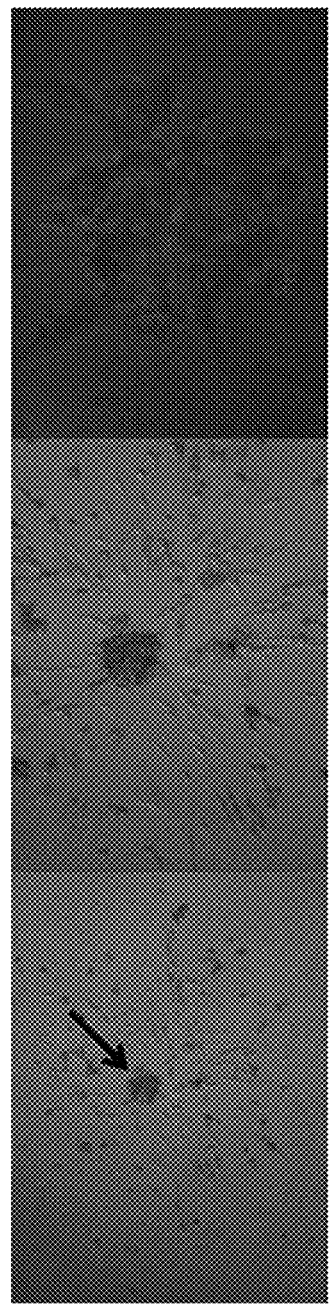
FIG. 7A Day 3 Post Transduction of JEMS with Lenti-Oct 4-GFP
FIG. 7B Day 4 Post Transduction of JEMS with Lenti-Oct 4-GFP Day 9 Post Transduction of JEMS with Lenti-Oct 4-GFP Day 3 Post Transduction of JEMS with Lenti-Nagog-GFP Lentiviral vector for the stem cell-specific expression of GFP-ZEOCIN in human adult stem cells Lentiviral vector for the stem cell-specific expression of a master regulator gene (e.g. CDX4/HOXB4 etc) and IRES EGFP in human adult stem cells.

Co-transducible lentiviral vectors for the tetracycline-inducible and stem/ lineage progenitor cell-specific expression of a master regulator gene (e.g. CDX4 and/or HOXB4 etc) and IRES EYFP in human adult stem cells Co-transducible lentiviral vectors for the tetracycline-inducible expression of a TAT-HA master regulator fusion genes (e.g. TAT-HA-CDX4 and/or TAT-HA-HOXB4 etc) and IRES EYFP in human ceder cells or human embryonic stem cells or derivatives of human embryonic stem cells

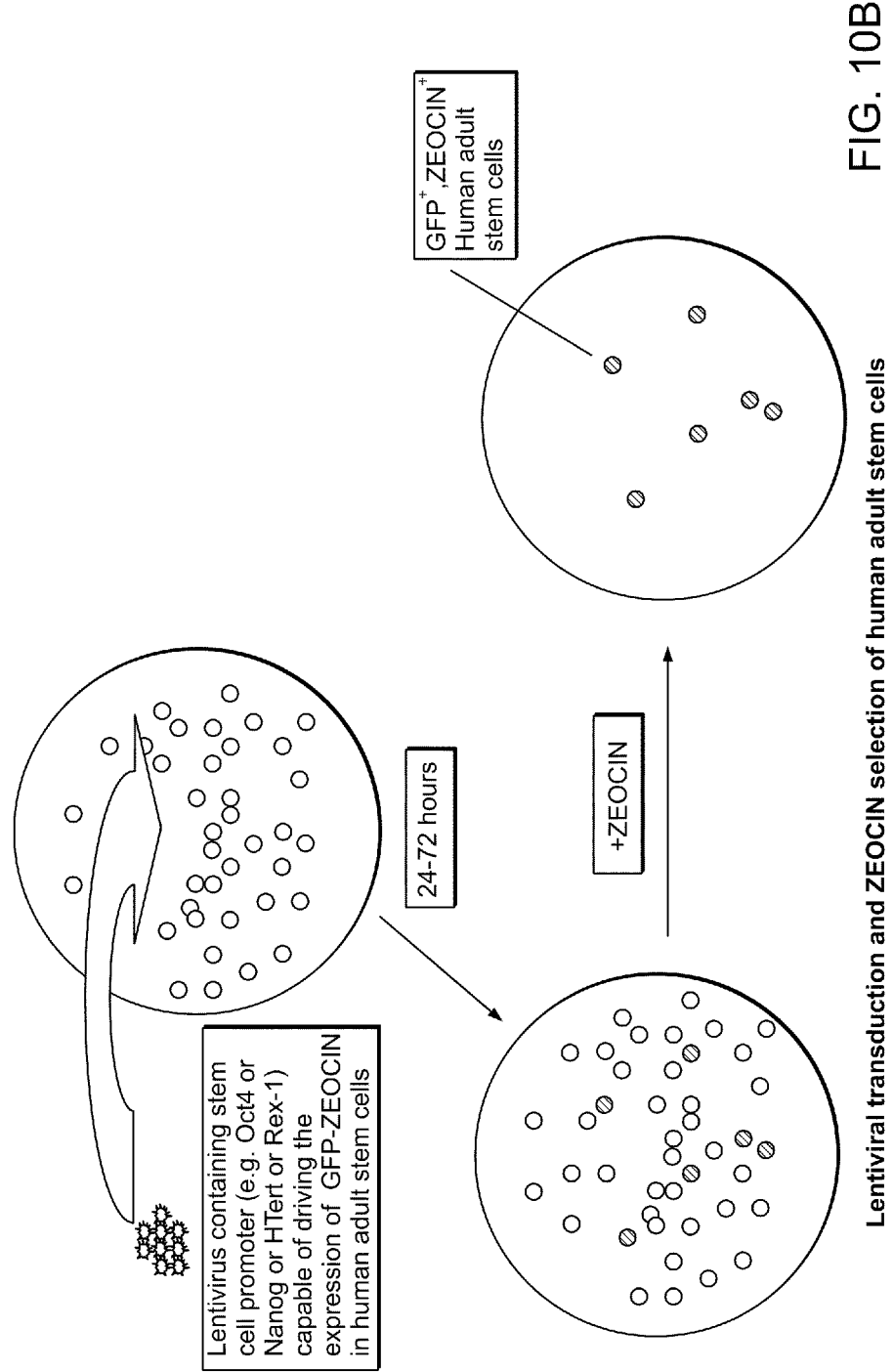

Tetracycline-inducible and stem/lineage progenitor cell-specific expression of master gene(s) in human adult stem cells and/or human adult stem / cell lineage progenitor cells Tetracycline-inducible expression of TAT-HA-master gene(s) in human feeder cells (e.g. human embryonic stem cells) and co-culture with human adult stem cells Generation of humanized rTtA transgenic mice for the in vivo expansion of repopulating human cell lineage-specific progenitor/stem (e.g. human CD34+ repopulating hematopoietic stem cells)

Generation of humanized cre transgenic mice for the in vivo expansion of repopulating human cell lineage-specific progenitor/stem cells (e.g. human Vav+ CD34+ repopulating hematopoietic stem cells)

Phenotypic Characteristics of Various Types of ASC

| | |
|---|---|
| Mesenchymal stem cells (MSC)[a] | International Society for Cellular Therapy criteria CD105, CD73, CD90, CD45-, CD34-, CD14-, CD11b, CD79a-, CD19-, HLA-DR- Other additional markers: Stro-1, SB-10(CD166), SH-2, (epitope on CD105), SH-3 and SH-4(epitope on CD73),CD44, CD29, CD31-, vWF- Markers of most primitive:CXCR4, CD133,CD34, p75LNGFR |
| Multipotent adult stem cells (MASC)[a] | CD13, CD49b, CD90, CD73, CD44, CD29, CD49a, CD105, MHC 1, HLA-DR-, CD14-, CD34-, CD45-, CD38-, CD133-, c-kit(cd117)- |
| Marrow-isolated adult multi-lineage Inducible cells (MIAMI)[a] | CD29, CD63, CD81,CD122, CD164, c-Met, BMPR1B, NTKR3, CD34-, CD36-, CD45-, CD117(c-kit)-, HLA-DR- |
| Multipotent adult progenitor cells (MAPC)[a] | SSEA-1, CD13, Flk-1 low, Thy-1 low, CD34-, CD44-, CD45-, CD117(c-kit)-, MHC I-, MHC II-, |
| Very small embryonic like stem cells (VSEL) | CXCR4, CD133, CD34, SSEA-1 (mouse), SSEA-4(human), AP, e-Met, LIF-R, CD45-, Lin-, HLA-DR-, MHC I-, CD90-, CD29-, CD105- |

*Phenotype of culture expanded adherent cells          *Stem Cell Review (2008) 4:89-99*

FIG. 13

MULTIPOTENT STEM CELLS AND USES THEREOF

CROSS-REFERENCE TO RELATED APPLICATIONS

This application claims the benefit under 35 U.S.C. §119 (e) of U.S. Provisional Application Ser. Nos. 61/247,242, filed Sep. 30, 2009, and 61/249,172, filed Oct. 6, 2009, and is a continuation-in-part of U.S. Application Ser. No. 12/598, 047, filed Jul. 28, 2010, which is a 35 U.S.C. §371 National Phase Entry Application of International Application No. PCT/US2008/005742, filed May 5, 2008, which designates the United States, and which claims the benefit under 35 U.S.C. §119(e) of U.S. Provisional Application Ser. No. 60/927,596, filed May 3, 2007, the entire contents of each of which the aforementioned patent applications are incorporated herein by reference in their entireties.

GOVERNMENT SUPPORT

This invention was made with government support under Grant No. AR050243 awarded by the National Institute of Arthritis and Musculoskeletal and Skin Diseases (NIAMS). The government has certain rights in the invention.

BACKGROUND OF THE INVENTION

A stem cell is commonly defined as a cell that (i) is capable of renewing itself; and (ii) can give rise to more than one type of cell through asymmetric cell division. Stem cells typically give rise to a type of multipotent cell called a progenitor cell; progenitor cells, in turn, proliferate and differentiate into lineage-committed cells that populate the body.

Pluripotent stem cells have the potential to differentiate into almost any cell type, whereas multipotent stem cells have the potential to differentiate into many cell types.

Stem cells exist in many tissues of embryos and adult mammals. Many different types of mammalian stem cells have been characterized and certain stem cells have not only been isolated and characterized, but have also been cultured under conditions to allow differentiation to a limited extent. Both adult and embryonic stem cells are able to differentiate into a variety of cell types and, accordingly, may be a source of replacement cells and tissues for tissues that are damaged in the course of disease or infection, or absent due to congenital abnormalities.

Various types of putative stem cells exist which, when differentiated into mature cells, carry out the unique functions of particular tissues, such as heart, liver, or neuronal tissue. These cells are important for the treatment of a wide variety of disorders, including malignancies, inborn errors of metabolism, hemoglobinopathies, immunodeficiencies and the replacement of damaged and diseased tissues. Recent successes in transplanting such stem cells have provided new clinical tools to reconstitute and/or supplement bone marrow after myeloablation due to disease, exposure to toxic chemicals and/or radiation. Evidence exists that demonstrates that stem cells can be employed to repopulate many, if not all, tissues and restore physiologic and anatomic functionality. The use of stem cells in tissue engineering, gene therapy delivery and cell therapeutics is also advancing rapidly.

Prior to the present invention, it was difficult to obtain sufficient quantities and populations of human stem cells capable of differentiating into a variety of cell types. Presently, stem cells are in critically short supply. Obtaining sufficient numbers of human stem cells has been problematic for several reasons.

First, isolation of normally occurring populations of stem cells in adult tissues has been technically difficult and costly due, in part, to the limited quantity of such cells found in blood and/or tissues. The isolation of stem cells is generally laborious, involving the harvesting of cells or tissues from a patient or donor, and subsequently culturing and/or propagating the cells in vitro. Certain cell types, such as nerve cells and cardiac cells, differentiate during development, and adult organisms are not known to generally replace these cells. Even in cell types that are replaced in adult organisms (e.g., epithelial cells and hematopoietic cells), it has been a significant challenge to readily and inexpensively obtain stem cells in significant quantities. For example, mammalian hematopoietic cells (e.g., lymphoid, myeloid, and erythroid cells) are all believed to be generated by a single cell type called the hematopoietic "stem cell". However, these hematopoietic stem cells are very rare in adults, accounting for approximately 0.01% of bone marrow cells. Isolation of these cells based on surface proteins such as CD34 results in very low yields. Schemes to fractionate human hematopoietic cells into lineage committed and non-committed progenitors are technically complicated and often do not permit the recovery of a sufficient number of cells to address multilineage differentiation.

A second reason that obtaining sufficient number of human stem cells has been problematic is that procurement of these cells from embryos or fetal tissue has raised religious, ethical, and legal concerns. Alternative sources of such cells that do not require the use of embryonic or fetal tissue are therefore highly desirably.

Prior to the present invention, there have been few viable alternative sources of stem cells, particularly human stem cells.

It would therefore be of particularly great value in treating a wide variety of diseases to have an easily accessible quantity of embryonic-like stem cells that are found in the adult body that can reliably differentiate into a desired phenotype.

In addition, it would also be advantageous to have stem cells that do not require feeder cells. Many adult stem cell propagation protocols require feeder cells, which creates risks including infection, cell fusion, and/or contamination. As such, adult stem cells are have often been very difficult to expand in culture.

Thus, there is an urgent need for methods for identifying, propagating, and altering the state (e.g., by differentiation or dedifferentiation) of stem cells and to provide a source of cells that are transplantable to in vivo tissues in order to replace damaged or diseased tissue.

SUMMARY OF THE INVENTION

The present invention provides a purified population of stem cells that exist in the synovial fluid and blood, and related therapeutic methods. The cells of the invention are embryonic in character and prior to culture do not present the surface markers generally associated with other adult stem cells, even after days in culture. These cells also express key embryonic transcription factors within a few days of isolation, in contrast to other adult stem cells, which require longer periods of culture before such expression. Further, these cell can differentiate into all three germ layers (mesoderm, ectoderm, and endoderm) and do not form teratoma bodies in vitro. This discovery allows for a non-controversial supply of easily attainable embryonic-like stem cells.

Accordingly, in one aspect, the invention features an isolated adult stem cell that is capable of proliferating and differentiating into at least two of ectoderm, mesoderm, or endoderm (e.g., ectoderm and mesoderm, ectoderm and endoderm, mesoderm and ectoderm, mesoderm and endoderm), expresses at least one, two, three, four, five, six, or all of Oct-4, KLF-4, Nanog, Sox-2, Rex-1, GDF-3, and Stella, and does not detectibly express CD13, CD45, CD90, and CD34 and further does not detectibly express at least one, two, three, four, five, six, seven, eight, nine, ten, or all of MHC class I, MHC class II, CD44, CD105, CD49c, CD73, CD66A, CD66E, CXCR4, CD133 or an SSEA.

In another aspect, the invention provides an isolated quiescent adult stem cell that is capable of proliferating and differentiating into at least two of ectoderm, mesoderm, and endoderm and does not detectibly express Oct-4, CD13, CD45, CD90, and CD34 and further does not detectibly express at least one, two, three, four, five, six, seven, eight, nine, ten, or all of MHC class I, MHC class II, CD44, CD105, CD49c, CD73, CD66A, CD66E, CXCR4, CD133 or an SSEA.

In another aspect, the invention provides a population of isolated adult stem cells that are capable of proliferating and differentiating into at least two of ectoderm, mesoderm, and endoderm, express at least one, two, three, four, five, six, or all of Oct-4, KFL-4, Nanog, Sox-2, Rex-1, GDF-3, and Stella, and does not detectibly express CD13, CD45, CD90, and CD34 and further does not detectibly express at least one, two, three, four, five, six, seven, eight, nine, ten, or all of MHC class I, MHC class II, CD44, CD105, CD49c, CD73, CD66A, CD66E, CXCR4, CD133 or an SSEA, where from about 10% to about 30% of the population of adult stem cells are quiescent. In one embodiment, the population is a culture expanded population. In another embodiment, the cells are cryopreserved and the population is included within a container (e.g., vial, syringe or other container suitable for local delivery into a site within a human or animal, such as a bag or other container suitable for intravenous delivery of cells within a human or animal). In another embodiment, the population comprises stem cells in an amount of at least $1\times10^3$, at least $1\times10^6$, at least $1\times10^9$, at least $1\times10^{12}$, or at least $1\times10^{14}$. In another embodiment, the population is contained in a 0.9% NaCL solution. In one embodiment, the population further contains a bioactive compound (e.g., expresses a growth factor, a cytokine, an antibody or fragment thereof, or the population contains an organic molecule having a mass of less than 5,000 daltons.

In another aspect, the invention provides a master cell bank containing a plurality of cryopreserved individually packaged populations of isolated adult stem cells, each population including at least $1\times10^2$ or more of the cells of previous aspect.

In another aspect, the invention provides a method of forming an adipocyte, the method involving culturing a stem cell of a previous aspect under adipocyte-differentiating conditions. In one embodiment, the adipocyte-differentiating conditions include culturing with at least one, two, three or all of dexamethasone, 3-isobutyl-1-methylxanthine (IBMX), insulin, and indomethacin.

In another aspect, the invention provides a method of forming a muscle cell, THE method involving culturing a stem cell of a previous aspect under muscle cell differentiating conditions. In one embodiment, the conditions include culturing the cell with PDGF and TGF-β1.

In another aspect, the invention provides a method of forming a neural cell, the method involving the steps of contacting a stem cell of claim 1 under neural cell-forming conditions. In one embodiment, the conditions include culturing the cell with bFGF, FGF-8, SHH, and BDNF.

In another aspect, the invention provides a method of forming a hepatocyte, the method involving culturing a stem cell of claim 1 under hepatocyte-forming conditions. In one embodiment, the conditions include culturing the cell with hepatocyte growth factor (HGF) and FGF-4.

In another aspect, the invention provides a method of forming an endothelial cell, the method involving culturing a stem cell of claim 1 under endothelial cell-forming conditions. In one embodiment, the conditions include conditions include culturing the cell with VEGF.

In another aspect, the invention provides a method of forming a hematopoietic cell, the method involving culturing a stem cell of claim 1 under hematopoietic cell forming conditions. In one embodiment, the conditions include conditions include culturing the cell with bone morphogenic protein-4 (BMP4), VEGF, bFGF, stem cell factor (SCF), Flt3L, hyper IL6, thrombopoietin (TPO) and erythropoietin (EPO).

In another aspect, the invention provides a method for promoting wound healing in a subject, the method involving administering a stem cell of claim 1, or a committed or differentiated progeny thereof, to the wound or to a site near the wound in an amount sufficient to promote the healing of the wound. In one embodiment, the administration of the cells results in reduced scarring at the wound site.

In another aspect, the invention provides a method for treating a cardiovascular disease in a subject, the method involving administering to the subject a stem cell a previous aspect, or a committed or differentiated progeny thereof, in an amount sufficient to treat the disease. In one embodiment, the cardiovascular disease is myocardial infarction, congestive heart failure, ischemic cardiomyopathy, and coronary artery disease.

In another aspect, the invention provides a method of increasing vascularization in a subject, the method involving administering to the subject a stem cell of a previous aspect, or a committed or differentiated progeny thereof, in an amount sufficient to increase vascularization. In one embodiment, the subject is suffering from type II diabetes.

In another aspect, the invention provides a method for treating a neurological disorder in a subject, the method involving administering to the subject a stem cell of a previous aspect, or a committed or differentiated progeny thereof, in an amount sufficient to treat the disease. In one embodiment, the neurological disorder is a neurodegenerative disease (e.g., Parkinson's disease, Alzheimer's disease, or Huntington's disease) or neurological injury.

In another aspect, the invention provides a method for treating an autoimmune disease in a subject, the method involving administering to the subject a stem cell of a previous aspect, or a committed or differentiated progeny thereof, in an amount sufficient to treat the disease.

In another aspect, the invention provides a method for reducing or preventing rejection of a transplanted tissue in a subject, the method involving administering to the subject a stem cell of a previous aspect, or a committed or differentiated progeny thereof, in an amount sufficient to reduce or prevent the rejection.

In another aspect, the invention provides a process for expanding the population of a previous aspect involving passaging the population at least about three, four, five, six, seven, eight, nine, ten, fifteen, twenty, thirty, or forty times.

In another aspect, the invention provides a population of stem cells obtained according to the process of a previous aspect or any other method delineated herein.

In another aspect, the invention provides a process for differentiating the isolated stem cell of a previous aspect involving culturing the isolated stem cell under conditions sufficient to differentiate the isolated stem cell.

In various embodiments of the above aspects or any other aspect of the invention delineated herein, the SSEA is SSEA-4. In other embodiment of the above aspects, the cell is synovial fluid derived, blood derived or tissue derived. In other embodiments, the cell is substantially purified (e.g., at least about 20%, 25%, 30%, 40%, 50%, 75%, 80% or more cells of the invention. In other embodiments, the cell is isolated from a mammal (e.g., human). In other embodiments, the cell is isolated from an adult mammal. In still other embodiments, the cell contains a heterologous nucleic acid sequence.

In still another aspect, the invention features an isolated (e.g., purified or substantially purified) stem cell which is capable of proliferating and differentiating into ectoderm, mesoderm, and endoderm, expresses at least one of (e.g., at least 2, 4, 5, or 6 of) Oct-4, Nanog, Sox-2, KLF4, c-Myc, Rex-1, GDF-3, LIF receptor, and Stella, and does not express at least one of (e.g., at least 2, 3, 4, 5, 6, 7, 8, or all of) MHC class I, MHC class II, CD44, CD45, CD13, CD34, CD49c, CD66b, CD73, CD105, and CD90 cell surface proteins.

In another aspect, the invention features an isolated (e.g., purified or substantially purified) quiescent stem cell which is capable of proliferating and differentiating into ectoderm, mesoderm, and endoderm and does not express Oct-4 and at least one of (e.g., at least 2, 3, 4, 5, 6, 7, 8, or all of) MHC class I, MHC class II, CD44, CD45, CD13, CD34, CD49c, CD66b, CD73, CD105, and CD90 cell surface proteins. The stem cell may be proliferative following 1, 2, 3, 4, 5, 6, 7, 8, or 10 days in culture.

In either of the above two aspects, the stem cell may not express CD13, CD44, CD45, CD90, and CD105. The stem cell may be isolated from synovial fluid, blood, or other tissue. The cell may be isolated from a human or non-human animal (e.g., any described herein). The cell may be about 6 μm to about 15 μm or to 20 μm in size. The cell may further contain a heterologous nucleic acid sequence, which may include a stem cell-specific promoter (e.g., an embryonic transcription factor promoter such as an Oct-4 promoter, Nanog promoter, Sox-2 promoter, KLF4 promoter, c-Myc promoter, Rex-1 promoter, GDF-3 promoter, Stella promoter, FoxD3 promoter, Polycomb Repressor Complex 2 promoter, and CTCF promoter). The promoter may be operably linked to a detectable gene product (e.g., a fluorescent protein such as a GFP) or any gene product, including those described herein.

In another aspect, the invention features a population of cells including cells of either of the previous two aspects. The population may contain at least 5%, 10%, 20%, 30%, 40%, 50%, 60%, 70%, 80%, 90%, 95%, or 99% of the cells of the previous two aspects (e.g., an embryoid body). The population may further be part of a composition including a cryoprotectant (e.g., any described herein). The population may be present with a dendritic cell or an antigen presenting cell (e.g., in a cell culture including a dendritic cell or antigen-presenting cell). In another embodiment, the population of cells may be part of a composition with other types of stem cells (e.g., any known in the art such as mesenchymal cells or embryonic stem cells) or differentiated cells (e.g., any described herein, including myocytes, adipocytes, fibromyoblasts, ectodermal cells, muscle cells, osteoblasts, chondrocytes, endothelial cells, fibroblasts, pancreatic cells, hepatocytes, bile duct cells, bone marrow cells, neural cells, and genitourinary cells. Such cells may be autologous or allogenic to the stem cells of the invention.

In another aspect, the invention features a method for isolating a population of stem cells. The method includes the steps (a) providing a bodily fluid from a subject (e.g., a mammal such as a human); (b) enriching for a population of cells that are about 6 μm to 20 μm in size; and may optionally include (c) depleting cells from the population expressing stem cell surface markers or MHC proteins (e.g., any described herein), thereby isolating a population of stem cells. Step (c) may include depleting cells expressing MHC class I, CD66b, glycophorin a, or glycophorin b, or any of the cell surface markers described herein. The subject may be administered a stem cell mobilizing agent prior to step (a) providing. The subject may be suffering from osteoarthritis. The method may further include (d) cryopreserving the cells. In another embodiment, the method further includes (d) transfecting the cells with a polynucleotide vector containing a stem cell-specific promoter (e.g., an Oct-4, Nanog, Sox-9, GDF3, Rex-1, or Sox-2 promoter, or any promoter described herein) operably linked to a reporter or selection gene; and (e) further enriching the population for the stem cells using expression of the reporter or selection gene (e.g., using flow cytometry). In another embodiment, the method further includes (d) contacting the cells with a detectable compound (e.g., carboxyfluorescein diacetate, succinimidyl ester, or Aldefluor) which enters said cells, the compound being selectively detectable in proliferating and non-proliferating cells; and (e) enriching the population of cells for the proliferating cells. In another embodiment, the method further includes culturing the cells under conditions which form embryoid bodies (e.g., those described herein). The method may further include separating (e.g., by cell depletion) cell types such as granulocytes, T-cells, B-cells, NK-cell, red blood cells, or any combination thereof, from the stem cells of the invention. The method may further include culturing the population of stem cell under conditions which support proliferation of the cells (e.g., where the culturing conditions include the presence of dendritic cells or antigen-presenting cells). In any of the embodiments of this aspect of the invention, the cells may further be cryopreserved.

The invention also features a cell produced by any of the above methods. The invention also provides a method for identifying a stem cell, the method including the steps of introducing into a stem cell a vector comprising a stem cell-specific promoter coupled to at least one selectable marker gene, wherein said stem cell that does not express at least one of (e.g., at least 2, 3, 4, 5, 6, 7, 8, or all of) MHC class I, MHC class II, CD44, CD45, CD13, CD34, CD49c, CD66b, CD73, CD105, and CD90 cell surface proteins, is capable of differentiating into mesoderm, ectoderm, and endoderm; and expresses at least one embryonic transcription factor (e.g., Oct-4, Nanog, Sox-2, Rex-1, GDF-3, Stella, FoxD3, Polycomb), expressing the selectable marker gene from the stem-cell specific promoter in said stem cell; and detecting expression of the marker gene in the stem cell, thereby identifying the stem cell. The method may further comprise isolating the stem cell. The stem cell can be derived from the bodily fluid of a mammal, such as synovial fluid or blood. Preferably, the mammal is a human. In certain embodiments, the cell does not express CD13, CD44, and CD90.

In various embodiments, the stem cell-specific promoter is an Oct-4 promoter, Nanog promoter, Sox-2 promoter, Rex-1 promoter, GDF-3 promoter, Stella promoter, FoxD3 promoter, Polycomb Repressor Complex 2 promoter, or CTCF promoter. In one embodiment, the stem cell-specific promoter is flanked by loxP sites. In another embodiment, the vector is a retroviral vector.

In yet another embodiment, the selectable marker gene encodes a fluorescent protein, such as a Green Fluorescent Protein (GFP).

In yet another embodiment, the vector comprises two selectable marker genes. In a specific embodiment, the two selectable marker genes are a fluorescent protein and a protein sensitive to drug selection.

In yet another embodiment, the selectable marker gene encodes a cell surface protein.

In another aspect, the invention provides a stem cell isolated by a method comprising the steps of introducing into a stem cell a vector comprising a stem cell-specific promoter coupled to at least one selectable marker gene, wherein said stem cell does not express MHC class I, MHC class II, CD44, CD45, CD13, CD34, CD49c, CD73, CD105 and CD90 cell surface proteins; expressing the selectable marker gene from the stem-cell specific promoter in said stem cell; and detecting expression of the marker gene in the stem cell.

In yet another aspect, the invention provides a method for isolating proliferative stem cells from a population of mobilized cells, the method comprising the steps of introducing into a population of mobilized cells a vector comprising a stem cell-specific promoter coupled to at least one selectable marker gene, wherein said population comprises proliferative stem cells which express Oct-4, Nanog, Sox-2, Rex-1, GDF-3, and Stella, and do not express MHC class I, MHC class II, CD44, CD45, CD13, CD34, CD49c, CD73, CD105 and CD90 cell surface markers; expressing the selectable marker gene in said proliferative stem cells; detecting expression of the marker gene in said proliferative stem cells; and isolating said proliferative stem cells from the population of mobilized cells.

In one embodiment, about 5% to about 30% proliferative stem cells are isolated from a population of about 500,000-12,000,000 mobilized cells without expansion in vitro.

In yet another aspect, the invention provides proliferative stem cells isolated by the method comprising the steps of introducing into a population of mobilized cells a vector comprising a stem cell-specific promoter coupled to at least one selectable marker gene, wherein said population comprises proliferative stem cells which express Oct-4, Nanog, Sox-2, Rex-1, GDF-3 and Stella, and do not express MHC class I, MHC class II, CD44, CD45, CD13, CD34, CD49c, CD73, CD105 and CD90 cell surface markers; expressing the selectable marker gene in said proliferative stem cells; detecting expression of the marker gene in said proliferative stem cells.

In yet another aspect, the invention provides a method of obtaining stem cells from synovial fluid, the method comprising the steps of obtaining synovial fluid from a subject optionally treated with a stem cell mobilizing agent; centrifuging the synovial fluid at about 200 g to form a first pellet of cells, thereby obtaining a population of stem cells. The method may further include any of the enrichment procedures described herein. Such methods include applying said cells to a discontinuous density gradient and centrifuging the gradient at about 500 g to form a second pellet of cells; suspending the second pellet of cells in a solution to form a suspension. The method may also include contacting the suspension with an agent that binds to an MHC class I cell surface protein; to form a binding complex between said agent and cells that express an MHC class I cell surface protein; contacting the suspension with an agent that binds to glycophorin to form a binding complex between said agent and cells that express glycophorin; and removing the binding complex from the suspension to form an MHC class I and glycophorin-depleted suspension, thereby obtaining stem cells from synovial fluid. The method may further comprise isolating proliferative stem cells from the obtained stem cells, wherein said proliferative stem cells express Oct-4, Nanog, Sox-2, Rex-1, GDF-3 and Stella, and do not express MHC class I, MHC class II, CD44, CD45, CD13, CD34, CD49c, CD73, CD105 and CD90 cell surface markers. The invention also features a stem cell isolated by this method.

In yet another aspect, the invention provides a stem cell obtained from synovial fluid by a method comprising the steps of obtaining synovial fluid from a subject optionally treated with a stem cell mobilizing agent; centrifuging the synovial fluid at about 200 g to form a first pellet of cells; applying said cells to a discontinuous density gradient and centrifuging the gradient at about 500 g to form a second pellet of cells; suspending the second pellet of cells in a solution to form a suspension; contacting the suspension with an agent that binds to an MHC class I cell surface protein; to form a binding complex between said agent and cells that express an MHC class I cell surface protein; contacting the suspension with an agent that binds to glycophorin to form a binding complex between said agent and cells that express glycophorin; and removing the binding complex from the suspension to form an MHC class I and glycophorin-depleted suspension.

In yet another aspect, the invention provides a method for the differentiation of a stem cell of the invention into a cell lineage of a germ layer selected from the group consisting of ectoderm, mesoderm and endoderm, and/or a specific cell type including but not limited to a neural, glial, chondroblast, osteoblast, adipocyte, hepatocyte, muscle cell (e.g., smooth muscle or skeletal muscle), cardiac cell, pancreatic cell, pulmonary cell, and endothelial cell.

In yet another aspect, the invention provides a method of forming an adipocyte by culturing a stem cell of any of the previous aspects under adipocyte forming conditions (e.g., with dexamethasone, 3-isobutyl-1-methylxanthine (IBMX), insulin and indomethacin), thereby forming an adipocyte.

In yet another aspect, the invention provides a method of forming a cartilage cell by culturing a stem cell of any of the previous aspects under chondrocyte-forming conditions (e.g. with TGF-β1 and BMP-4) thereby forming a cartilage cell.

In yet another aspect, the invention provides a method of forming a bone cell by culturing a stem cell of any of the previous aspects under osteoblast-forming conditions (e.g. with BMP-2) thereby forming a bone cell.

In yet another aspect, the invention provides a method of forming a muscle cell by culturing a stem cell of any of the previous aspects under muscle cell-forming conditions (e.g., with PDGF and TGF-β1), thereby forming a muscle cell.

In yet another aspect, the invention provides a method of forming a neural cell by culturing a stem cell of any of the previous aspects under neural cell-forming conditions (e.g., with bFGF, FGF-8, SHH and BDNF), thereby forming a neuron.

In yet another aspect, the invention provides a method of forming a hepatocyte by contacting a stem cell of any of the previous aspects under hepatocyte-forming conditions (e.g., with hepatocyte growth factor (HGF) and FGF-4), thereby forming a hepatocyte.

In yet another aspect, the invention provides a method of forming an endothelial cell by contacting a stem cell of any of the previous aspects under endothelial cell-forming conditions (e.g., with VEGF), thereby forming an endothelial cell.

In yet another aspect, the invention provides a method of forming a hematopoietic cell by culturing a stem cell of any of the previous aspects under hematopoietic cell-forming conditions (e.g., with one or more of bone morphogenic protein-4 (BMP4), VEGF, bFGF, stem cell factor (SCF), Flt3L, hyper IL6, thrombopoietin (TPO), and erythropoietin (EPO)), thereby forming a hematopoietic cell.

In any of the above differentiating methods, the method may further include transplanting the differentiated cell into a subject (e.g., a human).

The invention also features the use of stem cells to treat disease. The stem cells of the invention may be used to treat any disease or condition including but not limited to those described herein.

In another aspect, the invention features a method for promoting wound healing in a subject. The method includes administering a stem cell of any of the above aspects, or a committed or differentiated progeny of the stem cell, to the wound or to a site near the wound in an amount sufficient to promote the healing of the wound. The administration of the cells may result in reduced scarring at the wound site.

In another aspect, the invention features a method for treating a cardiovascular disease in a subject. The method includes administering to the subject a stem cell of any of the above aspects, or a committed or differentiated progeny of the stem cell, in an amount sufficient to treat the disease (e.g., myocardial infarction, congestive heart failure, ischemic cardiomyopathy, and coronary artery disease).

In another aspect, the invention features a method of increasing vascularization in a subject. The method includes administering to the subject a stem cell of any of the above aspects, or a committed or differentiated progeny of the stem cell, in an amount sufficient to increase vascularization. For example, the subject may be suffering from type II diabetes.

In another aspect, the invention features a method of treating a neurological disorder or neurological damage. The method includes administering to the subject a stem cell of any of the above aspects, or a committed or differentiated progeny of the stem cell, in an amount sufficient to treat the disorder. The disorder may be a neurodegenerative disease (e.g., Parkinson's disease or any neurodegenerative disease described herein).

In another aspect, the invention features a method of suppressing an immune response in a subject (e.g., a subject suffering from an autoimmune disease such as those described herein) by administering a stem cell of the invention to the subject.

In another aspect, the invention features a method of treating skeletal muscle disease such as fibrosis (e.g., muscular dystrophy, such as such as Duchenne's and Becker's muscular dystrophy, and denervation atrophy), by administering a stem cell of the invention, or a differentiated progeny of the stem cell, in an amount sufficient to treat the disease.

In another aspect, the invention features a method of treating an autoimmune disease (e.g., any described herein). The method includes administering to the subject a stem cell of any of the above aspects, or a committed or differentiated progeny of the stem cell, in an amount sufficient to treat the disease.

In another aspect, the invention features a method of replacing or repairing bone or cartilage. The method includes administering to the subject a stem cell of any of the above aspects, or a committed or differentiated progeny of the stem cell, in an amount sufficient to partially or completely repair or replace the cartilage or bone.

In any of the above treatment methods, the stem cells of the invention may be administered simultaneously with, prior to, or following administration of a differentiated cell (e.g., an autologous or allogenic cell).

In any of the above treatment methods, autologous or allogenic stem cells may be administered.

BRIEF DESCRIPTION OF THE DRAWINGS

FIG. 1a shows forward and side scatter of synovial fluid mononuclear cells. FIG. 1b shows Group A cell surface profile: small size and side scatter. FIG. 1c shows group B cell surface profile: medium size and small side scatter. FIG. 1d shows group C cell surface profile: large size and small side scatter. FIG. 1e shows a comparison of Class-I and CD44 expression in Groups A, B, and C.

FIG. 2 shows the expression of embryonic stem cell genes: Nanog, Oct-4, Rex-1 and Sox-2.

FIG. 3 shows expansion and proliferative capacity of undifferentiated stem cells of the invention. FIG. 3a depicts a low-power light microscopic view of cell morphology after culture for 3 days, 6 days, and 9 days.

FIGS. 7a-7d show an example of stem cells transduced with Lenti-Oct-4 GFP (3.5 kb Oct 4 promoter) or Lenti-Nanog-GFP (2.5 kb Nanog promoter). Freshly isolated stem cells were sorted as previously described, pulsed with $10^7$-$10^8$ viral particles per ml, and assessed for fluorescence daily. FIG. 7a shows a stem cell aggregate 3 days after transduction, low (left panel) and high (right panel). FIG. 7b shows a stem cell aggregate 4 days after transduction, at low (left), medium (middle), and high (right) magnifications. FIG. 7c shows a stem cell aggregate 9 days after transduction, at low (left) and high (right) magnifications. FIG. 7d shows a stem cell aggregate 3 days after transduction, at low (left), medium (middle), and high (right) magnifications.

FIG. 8a shows H2B-EGFP, and FIG. 8b shows GFP-ZEOCIN in human adult stem cells. FIG. 8c is a map of the lentiviral vector for the stem-cell specific expression of a master regulator gene and IRES-EGFP in human adult stem cells.

FIG. 9a shows a co-transducible lentiviral vector system for the tetracycline-inducible and stem/lineage progenitor cell-specific expression of a master regulator gene and IRES EYFP in human adult stem cells. FIG. 9b shows a co-transducible lentiviral vector system for the tetracycline-inducible expression of a TAT-HA master regulator fusion gene construct and IRES EYPF in human feeder cells or human embryonic stem cells or derivatives of human embryonic stem cells.

FIGS. 10a-10c are schematic diagrams showing lentiviral transduction and FACS (FIG. 10a) or ZEOCIN (FIG. 10b) selection of human adult stem cells. FIG. 10c shows expression of master genes in human adult stem cells.

FIG. 12a shows generation of humanized rTtA transgenic mice for the in vivo expansion of repopulating human cell lineage-specific progenitor/stem cells. FIG. 12b shows generation of humanized cre transgenic mice for the in vivo expansion of repopulating human cell-lineage specific progenitor/stem cells.

FIG. 13 shows the phenotypic characteristics of other adult stem cells. Classical stem cell surface proteins are used to distinguish the different types of adult stem cells (e.g. mesenchymal stem cells and multipotent adult stem cells). Cell surface proteins common to other adult stem cells are not characteristic of the ELA Stem Cell™. Note the presence of CXCR4 and CD133 on mesenchymal and very small embryonic like stem cells. These surface markers are not present on the ELA Stem Cell™.

DETAILED DESCRIPTION OF THE INVENTION

Figure 1A:
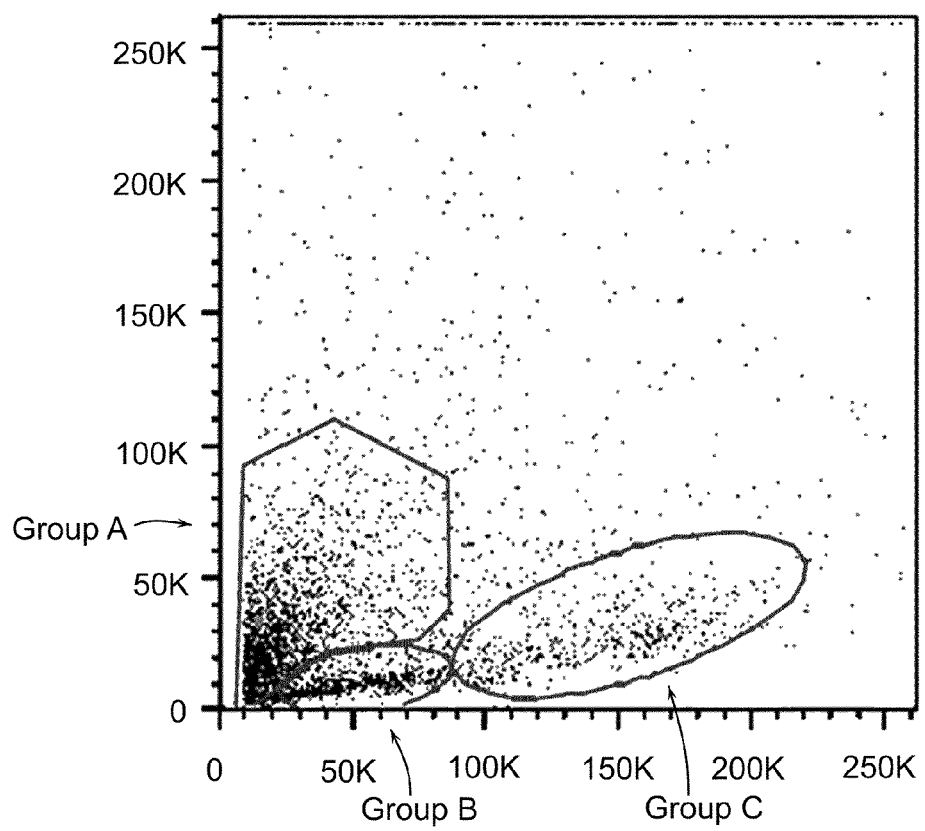
FIGS. 1a-1e show dot plots of undifferentiated stem cells of the invention. The freshly isolated stem cells were sorted into 3 groups as shown, Groups A, B, and C, and analyzed for Oct-4, Rex-1, Runx2, Sox-9, Nanog, Class I, CD44, and CD45 expression.
Figure 1B:
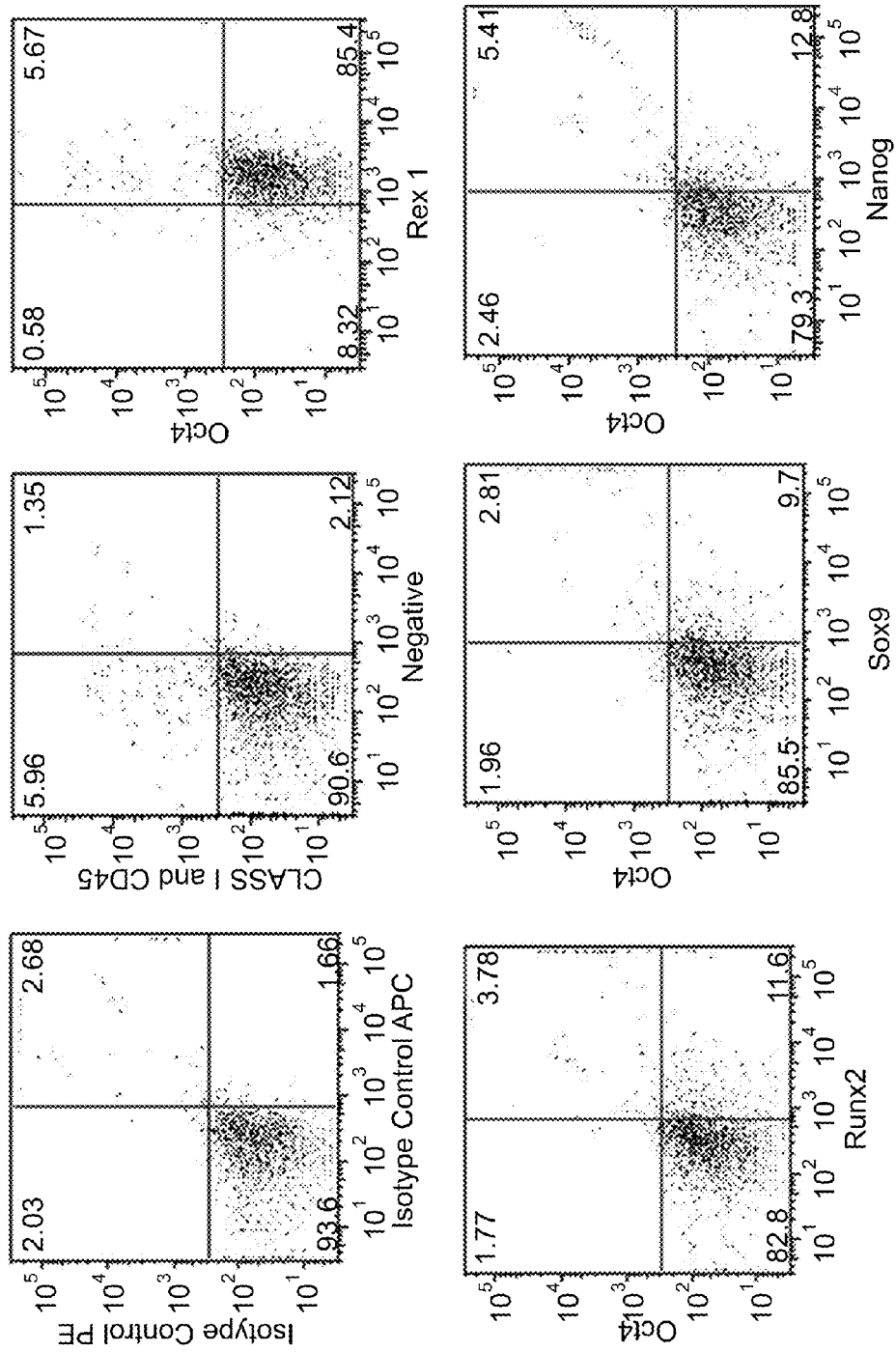
Figure 1C:
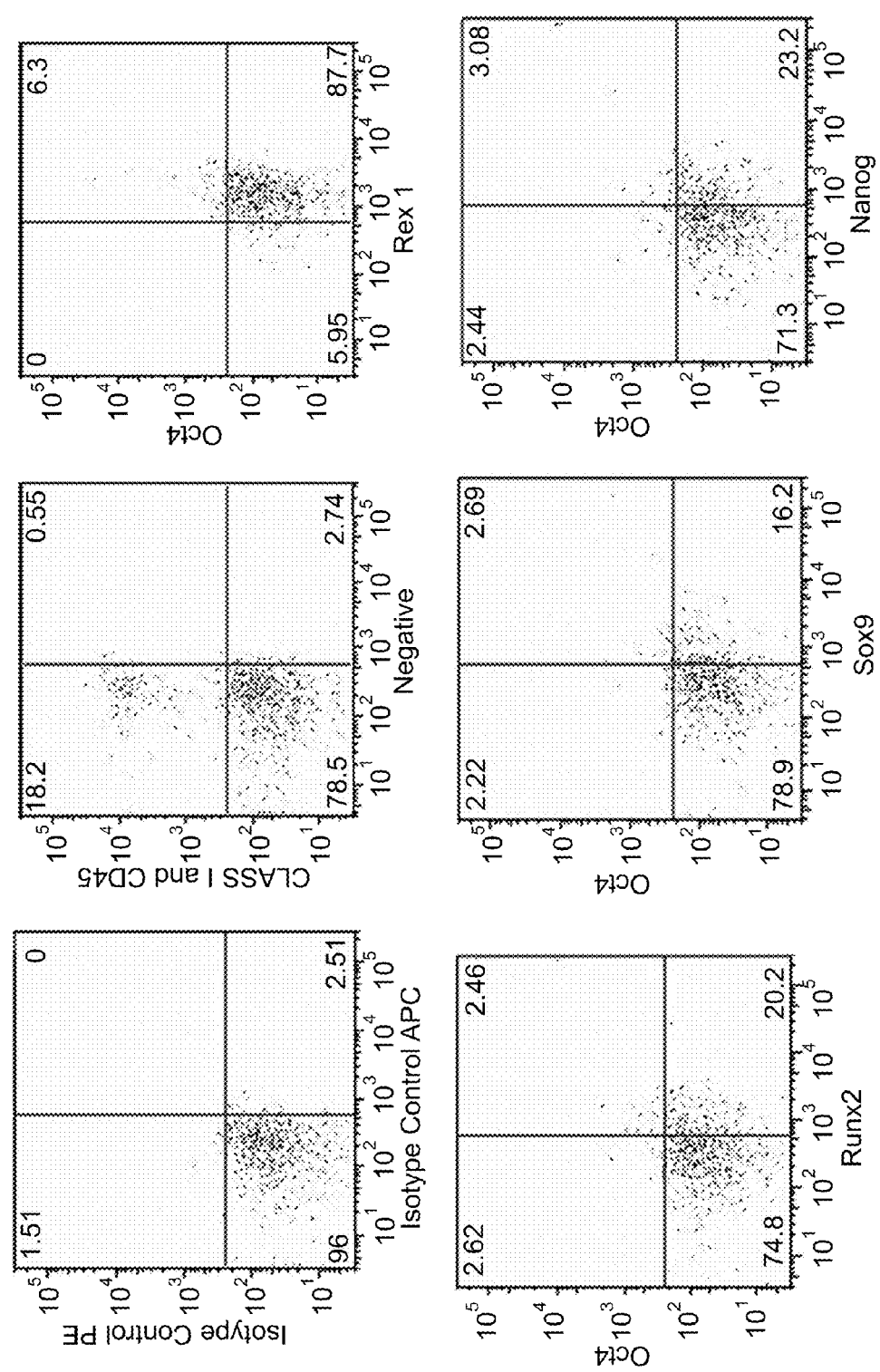
Figure 1D:
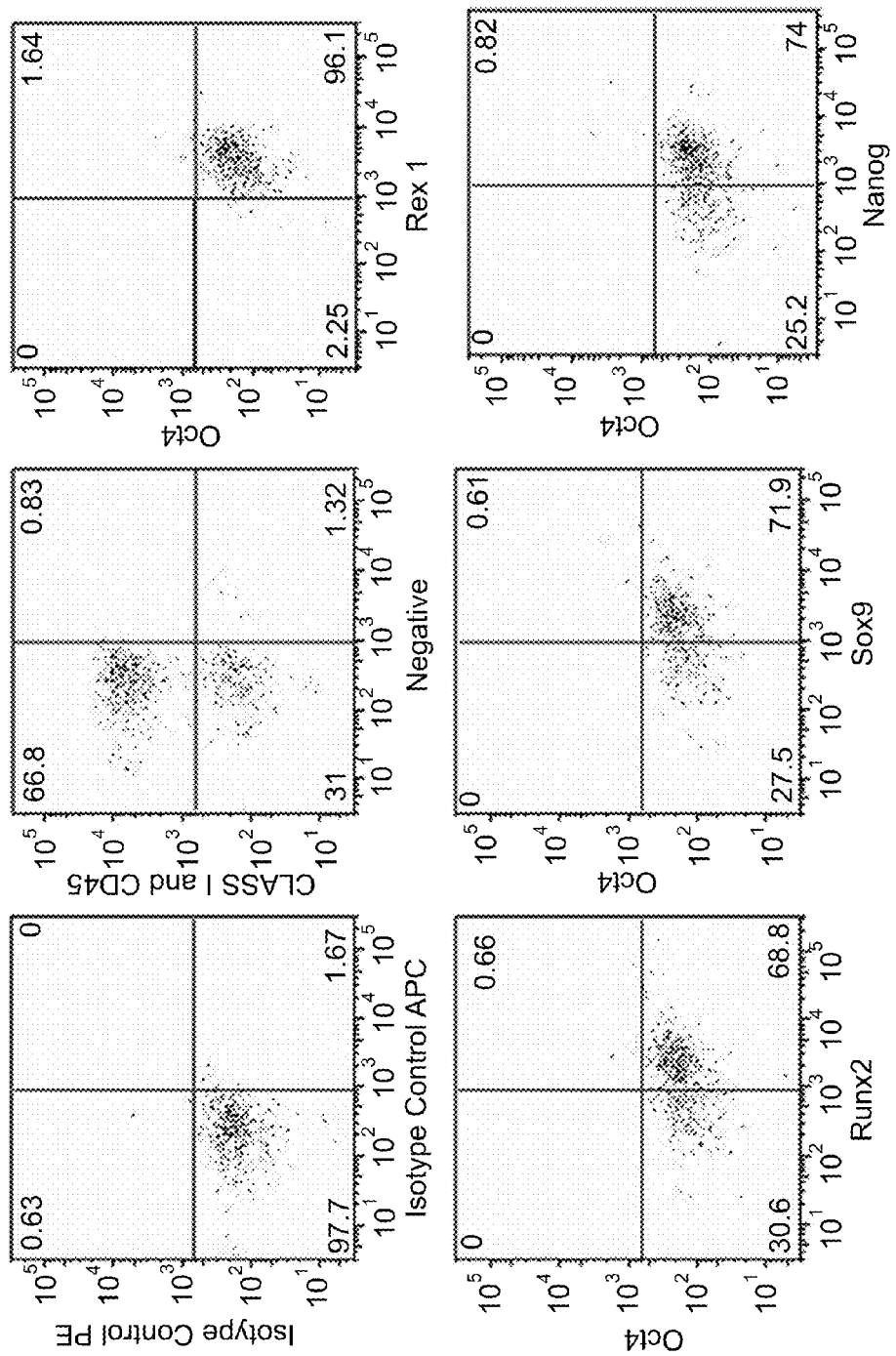
Figure 1E:
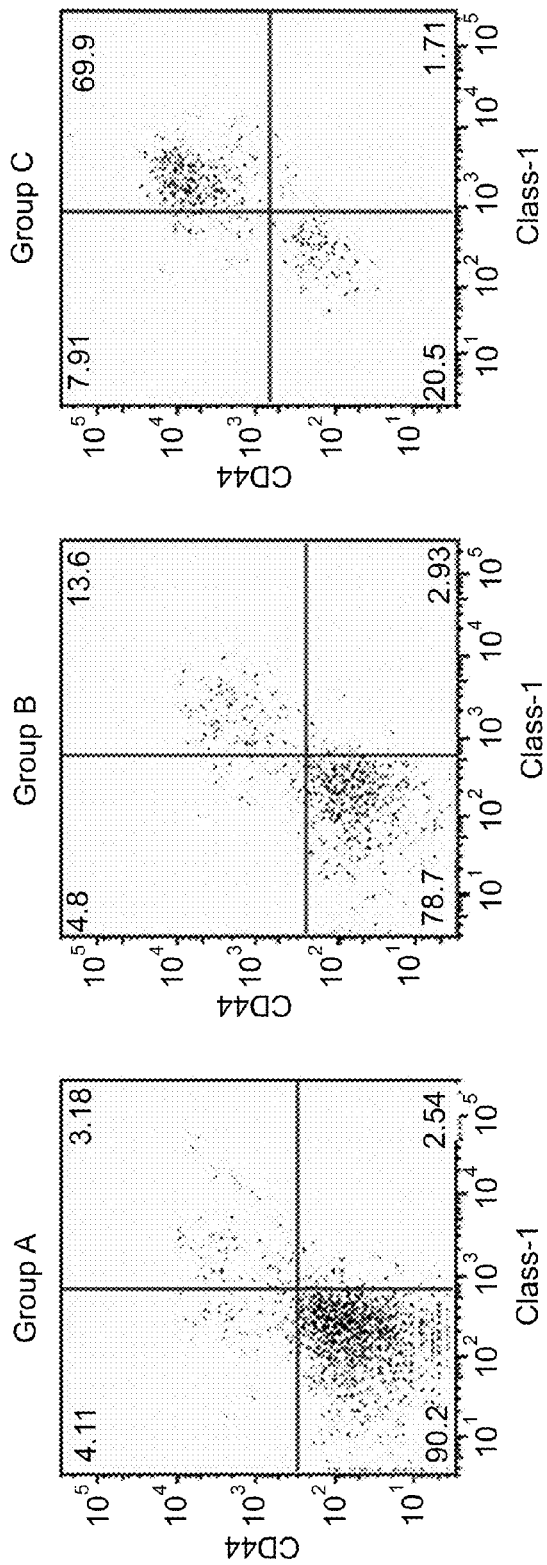

The invention provides adult stem cells and related therapeutic methods.

The invention is based, at least in part, on the discovery that adult stem cells of the invention lack the expression of certain cell surface markers typically found in differentiated cells, as well as lacking the expression of classical adult stem markers.

As used herein, a "stem cell" is a multipotent or pluripotent cell that (i) is capable of self-renewal; and (ii) can give rise to more than one type of cell through asymmetric cell division. The term "self renewal" as used herein, refers to the process by which a stem cell divides to generate one (asymmetric division) or two (symmetric division) daughter cells having development potential indistinguishable from the mother cell. Self renewal involves both proliferation and the maintenance of an undifferentiated state.

As used herein, a "proliferative stem cell" refers to a stem cell that is rapidly dividing, for example, at a rate of one division every 12, 18, 24, 36, or 48 hours.

As used herein, a "quiescent stem cell" refers to a stem cell that is not dividing and is in the Gap0 (G0) phase of the cell cycle. A "quiescent stem cell" expresses genes responsible for sustaining an epigenetic state of silence, which refers to a state in which the cellular chromatin is organized such that gene expression is substantially decreased. For example, acetylation of histone H3 and H4 correlates with gene expression activation, while deacetylation correlates with gene expression silencing (Fry et al., Curr. Biol. 11:R185-197, 2001). To date at least eight acetylatable lysine positions are known in the N termini of histone H3 (K9, K14, K18, and K23) and H4 (K5, K8, K12, and K16) and six methylatable lysine positions exist in those of histone H3 (K4, K9, K27, K36, and K79) and H4 (K20). Methylation of histone H3 (which can be acetylated at lysine position K4) also marks active chromatin, which contrasts with the modulation of inactive chromatin by methylation of H3 (which can be methylated at K9) (Lachner et al., J. Cell Sci. 116:2117-2124, 2003). Methylation of H3 at position K27 is an epigenetic marker for recruitment of polycomb group (Pc-G) complexes (Czermin et al., Cell 111:185-196, 2002) and is prominent in the inactivated X chromosome of female mammalian somatic cells (Plath et al., Science 300:131-135, 2003; Silva et al., Dev. Cell 4:481-495, 2003; Cao et al., Science 298:1039-1043, 2002). Thus, acetylation and methylation of histone H3 and H4 amino termini result in regulation of gene activity through the modulation of chromatin conformation, which propagates stably activated or silenced chromatin domains.

As used herein, the term "mobilized cells" refers to cells which have been exposed to an agent (e.g., any of those described herein) that promotes movement of the cells from the bone marrow into the peripheral blood and/or other reservoirs of the body (e.g., synovial fluid) or tissue.

As used herein, the term "stem cell-specific promoter" is a promoter that is capable of driving transcription of a gene in a multipotent stem cell, but not in a lineage-committed or differentiated cell. Exemplary stem cell-specific promoters are described herein.

A "nucleic acid molecule" is a strand of linked nucleic acids. The term "nucleic acid" is well known in the art. A "nucleic acid" as used herein will generally refer to a molecule (i.e., a strand) of DNA, RNA, or a derivative or analog thereof, comprising a nucleobase. A nucleobase includes, for example, a naturally occurring purine or pyrimidine base found in DNA (e.g., an adenine, guanine, thymine, or cytosine) or RNA (e.g., an adenine, guanine, uracil, or cytosine).

As used herein, the term "heterologous nucleic acid molecule" refers to any heterologous polynucleotide sequence. The sequence can comprise a polynucleotide sequence obtained from a source other than the cell into which it is introduced (e.g., an exogenous sequence). The polynucleotide can comprise a sequence of synthetic or naturally occurring DNA or RNA nucleotide bases.

As used herein, the term "selectable marker gene" refers to a gene, which upon its expression into a polypeptide in a cell, is detectable due to a specific property of the polypeptide (e.g., enzymatic activity or fluorescence).

As used herein "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to, small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

As used herein "RNAi" (RNA interference) refers to a post-transcriptional silencing mechanism initiated by small double-stranded RNA molecules that suppress expression of genes with sequence homology.

As used herein, the term "cell surface protein" refers to a protein that is present on the surface of a cell.

As used herein, the term "expansion" refers to the propagation of a cell or cells without terminal differentiation.

As used herein, the term "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell, or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). By "committed" or "differentiated" is meant a cell that expresses one or more markers or other characteristic of a cell of a particular lineage.

As used herein, the term "isolated" refers to a stem cell or population of daughter stem cells in a non-naturally occurring state outside of the body (e.g., isolated from the body or a biological sample from the body). The biological sample can include synovial fluid, blood (e.g., peripheral blood), or tissue.

As used herein, the term "purified" as in a "purified cell" refers to a cell that has been separated from the body of a subject but remains in the presence of other cell types also obtained from the body of the subject. By "substantially purified" is meant that the desired cells are enriched by at least 20%, more preferably by at least 50%, even more preferably by at least 75%, and most preferably by at least 90% or even 95%.

By a "population of cells" is meant a collection of at least ten cells. Preferably, the population consists of at least twenty cells, more preferably at least one hundred cells, and most preferably at least one thousand, or even one million cells. Because the stem cells of the present invention exhibit a capacity for self-renewal, they can be expanded in culture to produce populations of even billions of cells.

"Germ layers" are the three primary layers formed as a result of gastrulation in early stage embryos, consisting of endoderm, mesoderm, and ectoderm. Embryonic germ layers are the source from which all tissues and organs derive. The endoderm is the source of, for example, pharynx, esophagus, stomach, intestine and associated glands (e.g., salivary glands), liver, epithelial linings of respiratory passages and gastrointestinal tract, pancreas and lungs. The mesoderm is the source of, for example, smooth and striated muscle, connective tissue, vessels, the cardiovascular system, blood cells, bone marrow, skeleton, reproductive organs and excretory organs. Ectoderm is the source of, for example, epidermis (epidermal layer of the skin), sensory organs, the entire nervous system, including brain, spinal cord, and all the outlying components of the nervous system.

The term "multipotent," with respect to stem cells of the invention, refers to the ability of the stem cells to give rise to cells of all three primitive germ layers (endoderm, mesoderm, and ectoderm) upon differentiation.

The term "allogeneic," as used herein, refers to cells of the same species that differ genetically from cells of a host.

The term "autologous," as used herein, refers to cells derived from the same subject.

The term "engraft" as used herein refers to the process of stem cell incorporation into a tissue of interest in vivo through contact with existing cells of the tissue.

By "does not detectibly express" means that expression of a protein or gene cannot be detected by standard methods. In the case of cell surface markers, expression can be measured by, e.g., flow cytometry, using a cut-off values as obtained from negative controls (i.e., cells known to lack the antigen of interest) or by isotype controls (i.e., measuring non-specific binding of the antibody to the cell). Thus, a cell that "does not detectibly express" a marker appears similar to the negative control for that marker. For gene expression, a gene "does not detectibly express" if the presence of its snRNA cannot be visually detected on a standard agarose gel following standard PCR protocols.

Conversely, a cell "expresses" the protein or gene if it can be detected by the same method.

The term "culture expanded population" means a population of cells whose numbers have been increased by cell division in vitro. This term may apply to stem cell populations and non-stem cell populations alike.

The term "passaging" refers to the process of transferring a portion of cells from one culture vessel into a new culture vessel.

The term "cryopreserve" refers to preserving cells for long term storage in a cryoprotectant at low temperature.

The term "bioactive compound" refers to agents capable of affecting the biological activity of a cell, tissue, or organ. A bioactive compound may be a small chemical compound, a polypeptide or biologically active fragment thereof, or a polynucleotide or a biologically active fragment thereof.

The term "master cell bank" refers to a collection of cryopreserved cells. Such a cell bank may comprise stem cells, non-stem cells, and/or a mixture of stem cells and non-stem cells.

As used herein, the term "conditions sufficient to differentiate" refers to cell culture conditions that are capable of supporting the differentiation of one or more undifferentiated cells to a particular cell fate. The differentiation need not be complete. In certain embodiments, the undifferentiated cell cultured under conditions sufficient to differentiate the cell expresses one or more markers characteristic of a differentiated cell.

As used herein, the term "loxP sites" refers to the consensus sites recognized by an enzyme of a bacteriophage (Cre-recombinase) in mediating site-specific recombination and excision.

As used herein, a "vector" or "expression vector" is a nucleic acid-based delivery vehicle comprising regulatory sequences and a gene of interest, which can be used to transfer its contents into a cell.

A "subject" is a vertebrate, preferably a mammal (e.g., a non-human mammal), more preferably a primate and still more preferably a human. Mammals include, but are not limited to, primates, humans, farm animals, sport animals, and pets.

By "embryoid body" is meant an aggregate of stem cells of the invention. In addition to expression of one or more of the transcription factors described herein (e.g., Oct-4, Nanog, Sox-2, Rex-1, GDF-3, and Stella), the cells in the embryoid body can also express KLF-4 or Myc.

The term "obtaining" as in "obtaining the stem cell" is intended to include purchasing, synthesizing or otherwise acquiring the stem cell (or indicated substance or material).

In this disclosure, the terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout the specification.

Stem Cells of the Invention

The invention provides quiescent adult stem cells having embryonic stem cell characteristics with the capacity to differentiate into two or more of ectoderm, mesoderm and endoderm, and having low immunogenic potential, as the stem cells of the invention do not express detectable levels of one or more cell surface markers including MHC class I, MHC class II, CD44, CD45, CD13, CD34, CD49c, CD73, CD66A, CD66b, CD66E, CD105, CD90, CXCR4, CD133 or an SSEA (e.g., SSEA-4). In one embodiment, the stem cells of the invention do not detectibly express CD13, CD45, CD90, and CD34.

The quiescent stem cells are in the resting phase of the cell cycle, Gap0 (G0), and therefore, may not exhibit proliferative characteristics, such as expression of the transcription factor Oct-4. Such stem cells are found in bodily fluids such as blood and synovial fluid or tissue. The blood may be mobilized or non-mobilized blood.

Upon activation, the quiescent stem cell becomes proliferative, and expresses one or more genes including, but not limited to, Oct-4 (Lau et al., Adv. Anat. Pathol. 13:76-79, 2006), Nanog (Pan et al., J. Biol. Chem. 280:1401-1407, 2005), Sox2 (Lee et al., Cell 125:301-313, 2006), GDF3 (Hexige et al., Neurosci. Lett. 389: 83-87, 2005), P16INK4 (Gray-Schopfer et al., Br. J. Cancer; 95:496-505, 2006), BMI (Itahana, K., Mol. Cell. Biol. 23:389-401, 2003), Notch (Chiang et al., Mol. Cell. Biol.; 26:6261-6271, 2006), HDAC4 (Zeremski et al., Genesis 35: 31-38, 2003), TERT (Middleman et al., Mol. Cell. Biol. 26:2146-2159, 2006), Rex-1 (Zhang et al., Stem Cells; 24:2669-2676, 2006), TWIST (Guenou et al., Hum. Mol. Genet. 14:1429-1439, 2005), KRUPPEL-LIKE FACTOR 4 (KLF-4; Takahashi et al., Cell. 2006 Aug. 25; 126(4):663-76; Yet et al., J Biol Chem. 1998 Jan. 9; 273(2):1026-31), and Stella (human DDPA3 Bowles et al., Cytogenet Genome Res. 2003; 101(3-4):261-5.), but the cells retain their low immunogenic potential because they do not express detectable levels of certain cell surface markers including one or more of MHC class I, MHC class II, CD44, CD45, CD13, CD34, CD49c, CD66b, CD73, CD105 and CD90. In certain embodiments, the cells do not express detectable levels of CD13, CD45, CD90, and CD34. The size of the cell has been observed to be about 6 μm to about 20 μm.

The proliferative stem cells of the invention are uniquely suited for large scale use. They are proliferative after less than ten days in culture, e.g., about one day, three days, or seven days in culture, and do not require expansion in order to achieve an activated and/or proliferative state. Accordingly, it is possible to obtain about 5% to about 30% proliferative stem cells from a population of about 500,000-12,000,000 mobilized cells without expansion in vitro.

Stem cells of the invention are multipotent, having the capacity to differentiate into a cell lineage of each germ layer (e.g., ectoderm, mesoderm, and endoderm). Upon further differentiation, the stem cells can be fully differentiated into cell types including but not limited to a neuron, chondroblast, osteoblast, adipocyte, hepatocyte, smooth muscle cell, skeletal muscle cell, cardiac cell, pancreatic cell, pulmonary cell, and endothelial cell. Methods for the differentiation of stem cells are well known in the art. Typically, stem cells are cultured in the presence of differentiation-specific agents, which promote lineage commitment. Differentiation-specific agents and conditions include, for example, PDGF (e.g., about 10 ng/ml) and TGF-β1 (e.g., about 5 ng/ml) for the formation of a muscle cell; bFGF (e.g., about 100 ng/ml), FGF-8 (e.g., about 10 ng/mL), SHH (e.g., about 100 ng/ml) and BDNF (e.g., about 10 ng/ml) for the formation of a neuron; hepatocyte growth factor (HGF) and FGF-4 for the formation of a hepatocyte; dexamethasone, 3-isobutyl-1-methylxanthine (IBMX), insulin and indomethacin for the formation of an adipocyte; VEGF (e.g., about 100 ng/ml of VEGF-165) for the formation of an endothelial cell; and bone morphogenic protein-4 (BMP4) (e.g., about 10 ng/ml), VEGF, bFGF, stem cell factor (SCF), Flt3L, hyper IL6, thrombopoietin (TPO), and erythropoietin (EPO) for the formation of a hematopoietic cell.

The stem cells of the invention can also form embryoid bodies upon culture. The cells forming the embryoid bodies, in addition to the embryonic transcription factors described herein, may additionally express KLF-4 or Myc. Exemplary culture conditions for embryoid body formation are described in Example 4 below.

Isolation of Stem Cells

Any bodily source where stem cells of the invention are suspected of residing may be used for purification according to the methods described herein. Methods of obtaining stem cells of the invention, particularly cells in blood and synovial fluid, can be conducted as described below.

Mobilization

Prior to removal of the cells from the subject, stem cells may optionally be mobilized using any method known in the art. Typically, stem cell mobilization is induced by administering an appropriate agent, such as a cytokine or chemotherapeutic agent, to the subject. Cytokines that can be used to mobilize stem cells include G-CSF, GM-CSF, Flt-3 ligand, stem cell factor (SCF), IL-3 receptor agonists (e.g., Daniplestim), thrombopoietin agonists, chimeric cytokines (e.g., leridistim and progenipoietin-1), peg-fligrastim, and SDF-1 antagonists (e.g., AMD 3100). Chemotherapeutic agents include cyclophosphamide (Cy), or combined chemotherapy regimens such as iphosphamide, carboplatin and etoposide (ICE) and etoposide, methylprednisolone, ara-c and cisplatin (ESHAP) (Cottler-Fox et al., Hematology Am Soc Hematol Educ Program pp. 419-37, 2003).

Purification of Stem Cells

The stem cells of the invention can be purified from any bodily fluid or tissue in which they are found, including synovial fluid and blood. In some embodiments, the stem cells of the invention are purified from the synovial fluid of a subject suffering from osteoarthritis.

One bodily reservoir in which the stem cells reside is synovial fluid. To obtain the stem cells from the synovial fluid, cells present in the fluid can be spun down in a centrifuge, pelleted, and resuspended. The cells pelleted from synovial fluid contain the stem cells of the invention. The cells from the pellet may be cultured or may be further purified, e.g., by cell depletion or using a discontinuous density gradient (e.g., DM-M, sucrose, or percoll gradients). In one exemplary protocol, synovial fluid from osteoarthritic patients is harvested, diluted in serum-free medium (AIM-V, GIBCO), and spun at about 200 g for about 15 minutes at room temperature. The pelleted population is then resuspended in AIM-V® (Invitrogen), which is a commercially available serum free defined culture media, up to the original synovial fluid volume. The cells are then counted with a hemacytometer. The resuspended, washed sample is layered over a discontinuous density gradient (DM-M, Stem Cell Technologies Inc.) and spun at 500 g for about 30 minutes at room temperature. The discontinuous density gradient separates synovial fluid into a buffy layer and a pelleted layer. This gradient advantageously prevents granulocytes from pelleting with the smaller cells (e.g., about 6 μm in diameter or less). Use of this gradient allows only two populations of cells (RBC and stem cells) to form the pellet. The buffy layer is found at the AIMV and DM-M interface while the pellet population is found in the conical portion of the tube. The desired cellular population is isolated from the pellet layer, washed in phosphate buffered saline (PBS), and prepared for flow cytometry analysis, if desired.

Stem cells of the invention may also be isolated from blood (i.e., hematopoietic tissue). Possible sources of human hematopoietic tissue include, but are not limited to, embryonic hematopoietic tissue, fetal hematopoietic tissue, and post-natal hematopoietic tissue. Embryonic hematopoietic tissue can be yolk sac or embryonic liver. Fetal hematopoietic can be selected from fetal liver, fetal bone marrow and fetal peripheral blood. The post-natal hematopoietic can be cord blood, bone marrow, normal peripheral blood, mobilized peripheral blood, hepatic hematopoietic tissue, or splenic hematopoietic tissue.

In one exemplary protocol, blood from mammals is harvested, diluted in serum-free medium (AIM-V, GIBCO), and spun at about 200 g for 10 minutes at room temperature, about three times. The pelleted red cell fraction can either be cultured or further enriched as described below. Further purification may include resuspending the cells in AIM-V up to two or three times the original volume. The resuspended, washed sample is layered over a combined gradient of Ficoll-Paque and Stem Cells Technologies Granulocyte gradient (ROSETTE SEP DM-M, Stem Cell Technologies). This gradient advantageously prevents granulocytes from pelleting with the smaller cells (e.g., 6 μm in diameter), thus allowing only two populations of cells (RBC and stem cells) to pellet. The sample is subsequently spun at about 500 g for 30 minutes at room temperature. The Ficoll-Stem Cell Technology gradients separate the cells into a buffy layer, an intermediate layer, and pelleted layer. The desired cellular population is isolated from the pelleted layer, washed in PBS, and resuspended in AIM V for further enrichment, if desired.

Further enrichment of the desired stem cells may be achieve by depletion of T cells (CD2/CD3), B cells (CD19/CD20), NK cells (CD16/CD56), dendritic cells (CD13, CD14, CD11B, MHC Class II), monocytes (CD13, CD14, CD11B Class II), granulocytes (CD13, CD14, CD66B), red blood cells, or any combination thereof.

Further separation can also be achieved using an anti-glycophorin A antibody which binds most, if not all, red blood cells. This antibody is added, and the red blood cells are depleted from the stem cell population. Sorting can then be performed either by flow cytometric or immunomagnetic bead selection. A variation of this method involves the depletion of all cells except the stem cells by using the tetrameric antibody complex, as described in U.S. Pat. No. 6,448,075.

Alternatively, red blood cells can be removed by CD71 and/or Hoechst33258 (HO258) staining, followed by sorting using flow cytometry. Such a method is described in Tao et al., Zhonghua Yi Xue Yi Chuan Xue Za Zhi. 17:352-354, 2000.

Another approach involves lysis of the red blood cells, and sorting using electric fields, as described in U.S. Pat. No. 6,043,066.

Because the stem cells of the invention, when cultured with dendritic cells typically proliferate more rapidly, and such dendritic cells occur naturally in synovial fluid, it may be desirable to purify the stem cells of the invention along with naturally occurring dendritic cells, e.g., using techniques which do not deplete dendritic cells from the stem cells of the invention.

Enrichment

Once a population of cells containing the desired stem cells has been isolated from a subject, (e.g., according to the methods described above), proliferating stem cells can be enriched. The procedures described above produce a mixed population of both quiescent and proliferating stem cells (FIGS. 1a-1e). If desired, proliferative stem cells of the invention, which are proliferative after less than ten days in culture and, do not require expansion in order to achieve an activated and/or proliferative state, can be enriched. The enrichment may be performed using dyes (e.g., either negative or positive identification of stem cells using such dyes such as those described herein), sorting techniques, or by using a vector with a stem-cell specific promoter operably linked to a detectable marker gene).

To perform the enrichment, a vector having a stem cell-specific promoter coupled to at least one selectable marker gene can be introduced into a cell population (e.g., a population of mobilized stem cells obtained from a source such as synovium or blood). Within the population are the proliferative stem cells that express at least one of Oct-4, KFL-4, Nanog, Sox-2, Rex-1, GDF-3, and Stella, and do not detectably express further does not detectably express at least one of CD105, CD66A, CD66b, CD66E, CXCR4, CD133, SSEA, MHC class I, MHC class II, CD44, CD45, CD13, CD34, CD49c, CD73, CD105 and CD90 cell surface markers. Preferably, cells of the invention do not detectibly express CD13, CD45, CD90, and/or CD34. Upon introduction into the proliferative stem cell, the selectable marker gene is expressed by internal factors that activate the stem cell-specific promoter. Detection of marker gene expression facilitates sorting and isolation of the cells according to methods known in the art (e.g., fluorescence activated flow cytometry and affinity bead purification).

The stem cell-specific promoter can be any promoter that is capable of driving transcription of a gene in a multipotent stem cell, but not in a lineage-committed or differentiated cell. Specificity for promoter activation in a multipotent cellular environment allows for activation of selectable marker gene expression within the target proliferative stem cells, but not within more committed progenitors. Preferably, the stem cell-specific promoter is an Oct-4 promoter (Sylvester et al., Nucleic Acids Res. 22:901-911, 1994), Nanog promoter (Wu da et al., Cell Res. 15:317-324, 2005), Sox2 promoter (Boer, et al., Nucleic Acids Res., 35:1773-1786, 2007), Rex-1 promoter (Shi et al., J. Biol. Chem., 281:23319-23325, 2006), GDF-3 promoter (Clark, A. T., Stem Cells, 2004; 22(2):169-79), Stella promoter (Clark, A. T., Stem Cells, 2004; 22(2): 169-79), FoxD3 promoter (Alkhateeb, A., J. Invest. Dermatol., 2005 125, 388-391), Polycomb Repressor Complex 2 promoter (Sparmann, A., Nat. Rev., 2006. 6, 846-856, and CTCF promoter (De La Rosa-Velazquez IA, Cancer Res., 2007; 67(6):2577-85).

The selectable marker gene may be any known in the art, and is preferably a gene which does not disrupt the growth and proliferation of a live cell, such as a fluorescent protein, preferably a Green Fluorescent Protein (GFP). Where additional selectivity is desirable for isolation, the vector may encode multiple selectable marker genes coupled to one or more stem cell specific promoters. For example, the vector may encode a fluorescent protein and a protein sensitive to drug selection. The selectable marker gene may also encode a cell surface protein which may be sorted according to standard methods known in the art.

The cells expressing the selectable marker gene from the stem-cell specific promoter may be isolated by, for example, fluorescence activated cell sorting as disclosed herein. A preferred sorting procedure is by fluorescent activated cell sorting (FACS), wherein the cells can be separated on the basis of the level of staining of the particular antigens. These techniques are well known to those skilled in the art and are described in various references including U.S. Pat. Nos. 5,061,620; 5,409,8213; 5,677,136; and 5,750,397; and Yau et al., Exp. Hematol. 18:219-222 (1990).

In specific embodiments, the stem cell-specific promoter is flanked by loxP sites, so that the promoter may be conveniently excised to prevent expression of the selectable marker gene following isolation. It may be advantageous to stop expression of the marker gene, for example, where clinical use of the cells is desired.

Vectors for use in enrichment methods of the invention can be any known in the art. Vectors containing both a promoter and a cloning site into which a heterologous polynucleotide can be operatively linked are well known in the art. One skilled in the art will readily recognize that any heterologous polynucleotide can be excised as a compatible restriction fragment and placed in a vector in such a manner as to allow proper expression of the heterologous polynucleotide from the stem cell-specific promoter. Such vectors are capable of transcribing RNA in vitro or in vivo, and are commercially available from sources such as Stratagene (La Jolla, Calif.) and Promega Biotech (Madison, Wis.). Examples of vectors include vectors derived from viruses, such as baculovirus, retroviruses, adenoviruses, adeno-associated viruses, and herpes simplex viruses; bacteriophages; cosmids; plasmid vectors; fungal vectors; synthetic vectors; and other recombination vehicles typically used in the art. These vectors have been used for expression in a variety of eukaryotic and prokaryotic hosts and may be used for protein expression. Specific non-limiting examples include pSG, pSV2CAT, and pXt1 from Stratagene (La Jolla, Calif.) and pMSG, pSVL, pBPV and pSVK3 from Pharamacia. Other exemplary vectors include the pCMV mammalian expression vectors, such as pCMV6b and pCMV6c (Chiron Corporation, Calif.), pSFFV-Neo, and pBluescript-SK+.

In order to optimize expression and/or in vitro transcription, it may be necessary to remove, add or alter 5' and/or 3' untranslated portions of polynucleotides to eliminate potentially extra inappropriate alternative translation initiation codons or other sequences that may interfere with or reduce expression, either at the level of transcription or translation. Alternatively consensus ribosome binding sites can be inserted immediately '5 of the start codon to enhance expression. The vector may further comprise a polyadenylation signal that is positioned 3' of the carboxy-terminal amino acid.

The vector may be introduced into a cell using any method known in the art for introducing a nucleic acid into a cell and such methods are well-known in the art and are described, for example, in Sambrook et al. (1989, In: Molecular Cloning: A Laboratory Manual, Cold Spring Harbor Laboratory Press, New York), and Ausubel et al. (1997, In: Current Protocols in Molecular Biology, Green & Wiley, New York). These methods include, but are not limited to, calcium phosphate precipitation transfection, DEAE dextran transfection, electroporation, microinjection, liposome-mediated transfer, chemical-mediated transfer, ligand-mediated transfer, and recombinant viral vector transfer, and the like.

In addition to or in place of cell enrichment using vector driven expression of various markers, additional cell enrichment techniques, including depletion techniques and other sorting techniques, may be employed.

One exemplary approach to enrich for the desired cells is magnetic bead cell sorting (MACS). The conventional MACS procedure is described by Miltenyi et al. (Cytometry 11:231-238, 1990). In this procedure, cells are labeled with magnetic beads and passed through a paramagnetic separation column. The separation column is placed in a strong permanent magnet, thereby creating a magnetic field within the column. Cells that are magnetically labeled are trapped in the column; cells that are not pass through. The trapped cells are then eluted from the column.

Stem cells of the invention can be enriched, for example, from a suitable bodily reservoir, such as the synovial fluid, using MACS to separate MHC class I and glycophorin positive cells. The sample is incubated with immunomagnetic beads that bind to MHC class I and/or glycophorin. Following incubation, samples are washed and resuspended at $10^5$-$10^6$ cells/ml and passed through a magnetic field to remove cells bound to the immunomagnetic beads. Such negative selection techniques are known to those of skill in the art. Monoclonal and polyclonal antibodies suitable for negative selection purposes are also known to those of skill in the art (see, for example, Leukocyte Typing V, Schlossman, et al., Eds. (1995) Oxford University Press), and are commercially available from a number of sources.

Other separation techniques, including affinity column chromatography using similar immunological reagents and FACS may also be used to remove particular cell populations in order to enrich for the desired cells.

Another exemplary enrichment method involves incubating purified cells with a detectable label that allows for sorting of cells. One exemplary label is carboxyfluorescein diacetate, succinimidyl ester (CFSE). CFSE passively diffuses into cells. CFSE remains colorless and nonfluorescent until the acetate group is cleaved by intracellular esterases to yield high fluorescent carboxyfluorescein succinimidyl ester. The dye-protein adducts that form in labeled cells are retained by the cells throughout development and meiosis, and can be used for in vivo tracing. The label is inherited by daughter cells after either cell division or cell fusion, and is not transferred to adjacent cells in a population. Because CFSE is partitioned equally among daughter cells with each division, thus allowing simultaneous analysis of cell number, position, as well as division status. Based on this partitioning, proliferating stem cells can therefore be identified and separated based on CFSE content.

An additional enrichment method involves the use of Aldefluor®, a fluorescent substrate for aldehyde dehydrogenase (ALDH). Human stem and progenitor cells express high levels of ALDH activity when measured by flow cytometry, whereas differentiated cells do not. Primitive hematopoietic cells are relatively resistant to alkylating agents such as the active derivatives of cyclophosphamide (e.g., 4-hydroxyperoxycyclophosphamide (4-HC) and mafosphamide). This resistance is due to the selective expression in primitive hematopoietic cells of the enzyme aldehyde dehydrogenase (ALDH). Fluorescent ALDH-substrates can be used to identify, quantitate and isolate hematopoietic cells by flow cytometry. Commercially available ALDEFLUOR® reagent systems offers a non-immunological way to identify human stem cells and progenitors from bone marrow (BM), mobilized peripheral blood (MPB) and umbilical cord blood (UCB) on the basis of their ALDH activity.

In various embodiments of the invention, multiple enrichment strategies can be combined to achieve isolation of proliferative stem cells. For example, vector-based isolation techniques can be used together with immunomagnetic sorting, either before or after vector-based sorting, and either with or without subsequent FACS analysis. In one exemplary protocol, purified cells that are MHC class I and glycophorin negative, obtained by negative selection methods described herein above, are resuspended to $10^5$ per ml and placed in 6-well tissue culture plastic. A lentiviral vector expressing GFP under the control of an Oct-4 stem cell-specific promoter is added to the cells and cultured for one day, for three days, five days, and seven days. The GFP-expressing cells are then subsequently sorted into individual wells by flow cytometry.

Culture

Stem cells of the invention can be maintained under standard cell culture conditions. For example, the cells can be maintained in Dulbecco Minimal Essential Medium (DMEM) or any other appropriate cell culture medium, supplemented with 1-50 ng/ml (e.g., about 5-15 ng/ml) platelet-derived growth factor-BB (PDGF-BB), 1-50 ng/ml (e.g., about 5-15 ng/ml) epidermal growth factor (EGF), 1-50 ng/ml (e.g., about 5-15 ng/ml) insulin-like growth factor (IGF), or 100-10,000 IU (e.g., about 1,060) LIF, with $10^{-10}$ to $10^{-8}$ M dexamethasone or other appropriate steroid, 2-10 µg/ml linoleic acid, and 0.05-0.15 µm ascorbic acid. Additional culture conditions can be identified by one of skill in the art.

In one example, about 50,000 cells are grown under suitable conditions. The cells can be plated in fibronectin-coated wells of 96 well plates in defined medium consisting of 1% PHS, 10 ng/ml IGF, 10 ng/ml EGF and 10 ng/ml PDGF-BB as well as transferrin, selenium, dexamethasone, linoleic acid, insulin, and ascorbic acid. The negatively-selected samples, which can optimally comprise a population of cells that is greater than 98% class I and glycophorin negative, can then be assessed for expression of adult and embryonic stem cell markers, as well as the undetectable expression of MHC class I, MHC class II, CD44, CD45, CD13, CD34, CD49c, CD73, CD105, CD90, cell surface markers, according to methods known in the art to confirm the identity of the purified population.

In specific embodiments, pooled human serum (1-2%) and human growth factors are used to supplement growth and proliferation. Preferably, stem cells of the invention are grown in the presence of 1-2% pooled human serum, epidermal growth factor, and platelet-derived growth factor-BB.

Other appropriate media include, for example, MCDB, Minimal Essential Medium (MEM), IMDM, and RPMI.

Minimum Essential Medium (MEM) is one of the most widely used of all synthetic cell culture media. Early attempts to cultivate normal mammalian fibroblasts and certain subtypes of HeLa cells revealed that they had specific nutritional requirements that could not be met by Eagle's Basal Medium (BME). Subsequent studies using these and other cells in culture indicated that additions to BME could be made to aid growth of a wider variety of fastidious cells. MEM, which incorporates these modifications, includes higher concentrations of amino acids so that the medium more closely approximates the protein composition of mammalian cells. MEM has been used for cultivation of a wide variety of cells grown in monolayers. Optional supplementation of non-essential amino acids to the formulations that incorporate either Hanks' or Eagles' salts has broadened the usefulness of this medium. The formulation has been further modified by optional elimination of calcium to permit the growth of cells in suspension.

Iscove's Modified Dulbecco's Media (IMDM) is a highly enriched synthetic media. IMDM is well suited for rapidly proliferating, high-density cell cultures.

MCDB media were developed for the low-protein and serum free growth of specific cell types using hormones, growth factors, trace elements and/or low levels of dialyzed fetal bovine serum protein (FBSP). Each MCDB medium was formulated (quantitatively and qualitatively) to provide a defined and optimally balanced nutritional environment that selectively promoted the growth of a specific cell line. MCDB 105 and 110 are modifications of MCDB 104 medium, optimized for long-term survival and rapid clonal growth of human diploid fibroblast-like cells (WI-38, MRC-5, IMR-90) and low passaged human foreskin fibroblasts using FBSP, hormone, and growth factor supplements. MCDB 151, 201, and 302 are modifications of Ham's nutrient mixture F-12, designed for the growth of human keratinocytes, clonal growth of chicken embryo fibroblasts (CEF) and Chinese hamster ovary (CHO) cells using low levels of FBSP, extensive trace elements or no serum protein.

RPMI-1640 was developed by Moore et. al. at Roswell Park Memorial Institute, hence the acronym RPMI. The formulation is based on the RPMI-1630 series of media utilizing a bicarbonate buffering system and alterations in the amounts of amino acids and vitamins. RPMI-1640 medium has been used for the culture of human normal and neoplastic leukocytes. RPMI-1640, when properly supplemented, has demonstrated wide applicability for supporting growth of many types of cultured cells, including fresh human lymphocytes in the 72 hour phytohemaglutinin (PHA) stimulation assay.

Stem cells of the invention can be maintained according to culture methods known in the art enhance proliferation. Preferably, proliferative stem cells of the invention are plated in fibronectin-coated wells of 96 well plates in defined medium consisting of 1% PHS, 10 ng/ml IGF, 10 ng/ml EGF and 10 ng/ml PDGF-BB as well as transferrin, selenium, dexamethasone, linoleic acid, insulin, and ascorbic acid.

To improve proliferation of these cells, the stem cells of the invention can be co-cultured with dendritic cells or antigen-presenting cells. These co-cultures can be carried out using basal or propagation culture conditions, as described herein. Dendritic cells can also be cultured using 10% pooled human serum (PHS) in standard culture medium plus antibiotics. We have observed that use of human serum results in the stem cells growing better (e.g., in 1%-2% PHS) as compared to bovine serum. Alternatively, serum free media may be used.

In other embodiments, the cells may be cultured in the presence of an extracellular matrix. Suitable procedures for proliferating cells in the presence of such matrices are described, for example, in U.S. Pat. No. 7,297,539.

Methods of Use

The production of stem cells, which can be either maintained in an undifferentiated state or directed to undergo differentiation into extraembryonic or somatic lineages ex vivo, allows for the study of the cellular and molecular biology of events of early human development, generation of differentiated cells from the stem cells for use in transplantation (e.g., autologous or allogenic transplantation), treating diseases (e.g., any described herein), tissue generation, tissue engineering, in vitro drug screening or drug discovery, and cryopreservation.

Transplant and Treatment of Disease

The stem cells of the invention may be used in autologous or allogenic stem cell transplantation. Stem cell transplantation is a useful approach for repairing damaged tissue, for example, in the treatment of diseases including, but not limited to, cardiac disease, neurodegenerative disease, diabetes, wound healing, diseases treatable by immunosuppression (e.g., autoimmune disorders), and bone and cartilage replacement or augmentation.

Stem cells of the invention have the potential to differentiate into a variety of cell types including, but not limited to, a neuron, chondroblast, osteoblast, adipocyte, hepatocyte, muscle cell (e.g., smooth muscle or skeletal muscle), cardiac cell, pancreatic cell, pulmonary cell, and endothelial cell. Accordingly, stem cells of the invention can be transplanted into a subject, engrafted into a target tissue, and differentiated in vivo to match the tissue type and supplement the target tissue, thereby restoring or enhancing function. In other cases, a stem cell is differentiated into a particular target tissue prior to transplantation.

Cardiac

The stem cells of the invention may be used in the treatment of cardiac conditions, e.g., where cardiac tissue has been damaged. Exemplary conditions include myocardial infarction, congestive heart failure, ischemic cardiomyopathy, and coronary artery disease. Such methods are described, for example, in U.S. Pat. No. 6,534,052, incorporated herein by reference in its entirety. Here, embryonic cells are introduced surgically and implanted into the infarcted area of the myocardium. After implantation, the embryonic stem cells form stable grafts and survive indefinitely within the infarcted area of the heart in the living host. In other cases, the cells are cultured under conditions that induce differentiation into cardiac tissue prior to transplantation.

Vascularization

The stem cells of the invention may also be used to increase vascularization. Doing so may be desirable when organs have been injured or in cases of diabetic disorders. Diseases in which increased vascularization is desirable include diabetes, atherosclerosis, arteriosclerosis, and any of the cardiac conditions described above.

Neurological Conditions

Stem cells of the invention or their committed or differentiated progeny may also be used to treat neural disorders where regeneration of tissue is desirable. Stem cells of the invention can address the shortage of donor tissue for use in transplantation procedures, particularly where no alternative culture system can support growth of the required committed stem cell. In another example, following transplantation into the central nervous system (CNS), ES cell-derived neural precursors have been shown to integrate into the host tissue and, in some cases, yield functional improvement (McDonald et al., Nat. Med. 5:1410-1412, 1999).

Neurological diseases that can be treated using stem cells of the invention include neurodegenerative disorders such as Parkinson's disease, polyglutamine expansion disorders (e.g., Huntington's Disease, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer's disease, amyotrophic lateral sclerosis, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Pelizaeus-Merzbacher disease, Pick's disease, primary lateral sclerosis, Refsum's disease, Sandhoff disease, Schilder's disease, spinal cord injury, brain injury, spinal muscular atrophy, Steele-Richardson-Olszewski disease, and Tabes dorsalis.

Immunosuppression and Treatment of Autoimmune Diseases

Stem cells of the invention may also be used to inhibit or reduce undesired or inappropriate immune responses. For example, the stem cells may be used to treat an autoimmune disease, to promote wound healing, or to reduce or prevent rejection of a tissue or organ. Stem cells can be used to suppress immune responses upon administration to subjects. See, e.g., U.S. Patent Application Publication No. 2005/0282272. Such approaches have also been proposed in Sykes et al., Nature 435:620-627, 2005 and Passweg et al., Semin. Hematol. 44:278-85, 2007. Other immunosuppressive uses of stem cells are described in U.S. Pat. Nos. 6,328,960, 6,368, 636, 6,685,936, 6,797,269, 6,875,430, and 7,029,666.

Thus, stem cells of the invention may be used for immunosuppression or to treat autoimmune disease. Immunosuppression may be desirable prior to transplantation of tissues or organs into a patient (e.g., those described herein). Autoimmune disease which may be treated by administration of stem cells include multiple sclerosis (MS), systemic sclerosis (SSc), systemic lupus erythematosus (SLE), rheumatoid arthritis (RA), juvenile idiopathic arthritis, and immune cytopenias. Other autoimmune disease which may be treated using stem cells of the include acute disseminated encephalomyelitis (ADEM), Addison's disease, Ankylosing spondylitis, antiphospholipid antibody syndrome (APS), aplastic anemia, autoimmune hepatitis, autoimmune oophoritis, celiac disease, Crohn's disease, diabetes mellitus type 1, gestational pemphigoid, Goodpasture's syndrome, Graves' disease, Guillain-Barré syndrome (GBS), Hashimoto's disease, idiopathic thrombocytopenic purpura, Kawasaki's disease, lupus erythematosus, mixed connective tissue disease, multiple sclerosis, myasthenia gravis, opsoclonus myoclonus syndrome, Ord's thyroiditis, pemphigus, pernicious anaemia, primary biliary cirrhosis, rheumatoid arthritis, Reiter's syndrome, Sjögren's syndrome, Takayasu's arteritis, temporal arteritis, warm autoimmune hemolytic anemia, and Wegener's granulomatosis.

In other embodiments, the stem cells of the invention can be used to reduce or prevent rejection of a transplanted tissue or organ. For instance, such a method can include engrafting the hematopoietic system of the tissue or organ recipient with stem cells of the invention obtained from the organ donor prior to transplanting the organ. By engrafting the hematopoietic system of the recipient with stem cells derived from the organ donor, rejection of the transplanted organ is thereby inhibited. Prior to engraftment and organ transplantation, the bone marrow of the recipient would be ablated by standard methods well known in the art. Generally, bone marrow ablation is accomplished by X-radiating the animal to be transplanted, administering drugs such as cyclophosphamide or by a combination of X-radiation and drug administration. Bone marrow ablation can be produced by administration of radioisotopes known to kill metastatic bone cells such as, for example, radioactive strontium, $^{135}$Samarium, or $^{166}$Holmium (Applebaum et al., 1992, Blood 80:1608-1613).

In some embodiments, autologous stem cells can be transplanted into a subject. A population of stem cells can be isolated from the recipient according to the methods described herein prior to ablating bone marrow of the recipient. The bone marrow of the individual is purged of malignant blasts and other malignant cells such that by transplanting the non-malignant stem cells back into to the individual, diseases such as melanomas may be treated.

Wound Healing

The stem cells of the invention can also be used to improve wound healing. Inflammation during healing of wounds has been shown to increase scarring at wound sites (Redd et al., Philos. Trans. R. Soc. Lond. B Biol. Sci. 359:777-784, 2004). Doing so at a wound site can promote healing of the tissue and further can decrease fibrosis and scarring at the wound site. Because formation of age-related wrinkles may also be caused by a scarring process, administration of stem cells of the invention to the site of wrinkles may reduce wrinkle formation or result in reduction or elimination of such of wrinkles as well as scars. Wound healing using regenerative cells from adipose tissue is described, for example, in U.S. Patent Application Publication Nos. 2005/0048034 and 2006/0147430. Such approaches can be adapted for use with the cells of the present invention.

Tissue Generation

Stem cells of the invention may also be used in promoting tissue generation, e.g., to replace damaged or diseased tissue. The term "promoting tissue generation" includes activating, enhancing, facilitating, increasing, inducing, initiating, or stimulating the growth and/or proliferation of tissue, as well as activating, enhancing, facilitating, increasing, inducing, initiating, or stimulating the differentiation, growth, and/or proliferation of tissue cells. Thus, the term includes initiation of tissue generation, as well as facilitation or enhancement of tissue generation already in progress. The term "generation" also includes the generation of new tissue and the regeneration of tissue where tissue previously existed.

Stem cells of the invention are multipotent, and have the potential to differentiate into a variety of cell types as discussed above. As such, the cells are useful in tissue generation. For instance, the stem cells of the invention can be used in the generation of neural cells. More specifically, stem cells of the invention can be induced to differentiate into neural cells using, for example, commercially available products such as NEUROCULT (Stem Cell Technologies).

Stem cells of the invention may be used in the production of tissues according to methods known in the art. U.S. Pat. No. 5,834,312, incorporated by reference in its entirety herein, for example, describes media and methods for the in vitro formation of a histologically complete human epithelium. The media are serum-free, companion cell or feeder layer free and organotypic, matrix free solutions for the isolation and cultivation of clonally competent basal epithelial cells. The media and methods of the invention are useful in the production of epithelial tissues such as epidermis, cornea, gingiva, and ureter. U.S. Pat. No. 5,912,175, incorporated by reference in its entirety herein, describes media and methods for the in vitro formation of human cornea and gingival from stem cells.

U.S. Pat. No. 6,497,872, incorporated by reference in its entirety herein, describes the differentiation of stem cells into neural cells (e.g., neurons, astrocytes, and oligodendrocytes), and methods for neurotransplantation in the undifferentiated or differentiated state, into a subject to alleviate the symptoms of neurological disease, neurodegeneration and central nervous system (CNS) trauma. Methods for the generation of suitable in autografts, xenografts, and allografts are also described.

In certain embodiments, it may be desirable to treat the cells in order to decrease the likelihood of transplant rejection, especially where non-autologous cells are used. The invention therefore features methods of decreasing uric acid production in cells, and cells in which uric acid production has been reduced. Exemplary means for doing so are described in U.S. Patent Application Publication No. 2005/0142121 and include treatment with compounds that decrease xanthine oxidase activity, such as allopurinol, oxypurinol, and BOF-4272. Other approaches include pre-treatment with low levels of tungsten to deplete molybdenum, a necessary cofactor for xanthine oxidase. Genetic or RNAi approaches which reduce transcription or translation of the xanthine oxidase gene or mRNA, may also be used to decrease uric acid production.

Stem cells of the invention may also be used for the generation of tissue engineered constructs or grafts, such as for use in replacement of bodily tissues and organs (e.g., fat, liver, smooth muscle, osteoblasts, kidney, liver, heart, and neural tissue). Stem cells of the invention may also be particularly well suited for the generation of tissue engineered constructs for use in replacement of musculoskeletal tissues (e.g., cartilage, joint, ligament, tendon).

For instance, the inability to use articular cartilage for self-repair is a major problem in the treatment of patients who have their joints damaged by traumatic injury or suffer from degenerative conditions, such as arthritis or osteoarthritis. New approaches to cartilage tissue repair based on implanting or injecting expanded autologous cells into a patient's injured cartilage tissue can be used. More recently, it has been proposed in EP-A-0 469 070, incorporated by reference herein in its entirety, to use a biocompatible synthetic polymeric matrix seeded with chondrocytes, fibroblasts or bone-precursor cells as an implant for cartilaginous structures. Stem cells of the invention can be differentiated into chondroblasts, and optionally seeded on a matrix for implantation into a patient in need of cartilage replacement. A suitable matrix is described, for example, in U.S. Pat. No. 6,692,761, incorporated by reference in its entirety herein, in a material that has hydrogel properties and allows for diffusion through the material itself, in addition to diffusion through its porous structure. This feature is highly advantageous when cells are seeded onto the scaffold and are cultured thereon, as it enables a very efficient transport of nutrient and waste materials from and to the cells. Secondly, the material closely mimics the structure and properties of natural cartilage, which, containing 80% water, is also a hydrogel. Other matrix cell based cultures are described in U.S. Pat. Nos. 5,855,619 and 5,962,325.

Methods of transplanting stem cells, stem cell-derived progeny (e.g., differentiated cells) and/or stem cell-derived tissue grafts are well known in the art. For example, U.S. Pat. No. 7,166,277, ("the '277 patent"), incorporated by reference in its entirety herein, describes the use of stem cells and their progeny as neuronal tissue grafts. The methods taught in the '277 patent for the in vitro proliferation and differentiation of stem cells and stem cell progeny into neurons and/or glia for the treatment of neurodegenerative diseases can be applied to the stem cells of the invention. Differentiation occurs by exposing the stem cells to a culture medium containing a growth factor which induces the cells to differentiate. Proliferation and/or differentiation can be done before or after transplantation, and in various combinations of in vitro or in vivo conditions, including (1) proliferation and differentiation in vitro, then transplantation, (2) proliferation in vitro, transplantation, then further proliferation and differentiation in vivo, and (3) proliferation in vitro, transplantation and differentiation in vivo. As another example, U.S. Pat. No. 7,150,990, incorporated by reference in its entirety herein, describes methods for transplanting stem cells and/or stem cell-derived hepatocytes into a subject to supplement or restore liver function in vivo. Such methods can also be applied to the stem cells of the invention. As yet another example, U.S. Pat. No. 7,166,464, incorporated by reference in its entirety herein, provides methods for the formation of a tissue sheet comprised of living cells and extracellular matrix formed by the cells, whereby the tissue sheet can be removed from the culture container to generate a genetically engineered tissue graft. Practitioners can follow standard methodology known in the art to transform the stem cells of the invention into a desired cell type or engineered construct for use in transplantation.

Stem cells of the invention may be used to produce muscle cells (e.g., for use in the treatment of muscular dystrophy (e.g., as Duchenne's and Becker's muscular dystrophy and denervation atrophy). See, e.g., U.S. Patent Application Publication No. 2003/0118565.

Gene Therapy

The stem cells of the invention may be transfected for use in gene therapy applications. Stem cells of the invention may be transfected using any methods known in the art such as viral vector systems, microinjection, electroporation, liposomes, and chromosome transfer, or any other method described herein may be used.

A wide variety of nucleic acids may be transfected into the stem cells of the invention. Thus, the invention should be construed to include nucleic acid products which are useful for the treatment of various disease states in a mammal. Such nucleic acids and associated disease states include, but are not limited to: DNA encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain α-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding ornithine transcarbamylase, associated with ornithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotinidase, associated with biotinidase deficiency; DNA encoding beta-glucocerebrosidase, associated with Gaucher disease; DNA encoding beta-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding antitrypsin for treatment of alpha-1 antitrypsin deficiency (emphysema); DNA encoding erythropoietin for treatment of anemia due to thalassemia or to renal failure; and, DNA encoding insulin for treatment of diabetes. Such DNAs and their associated diseases are reviewed in Kay et al. (1994, T.I.G. 10:253-257) and in Parker and Ponder (1996, "Gene Therapy for Blood Protein Deficiencies," In: Gene Transfer in Cardiovascular Biology: Experimental Approaches and Therapeutic Implications, Keith and March, eds.).

Where a vector includes coding sequences in addition to those encoding selectable marker genes, such additional coding sequences may be operably linked to a separate promoter/regulatory sequence. Many promoter/regulatory sequences useful for driving constitutive expression of a gene are available in the art and include, but are not limited to, for example, the cytomegalovirus immediate early promoter enhancer sequence, the SV40 early promoter, the Rous sarcoma virus promoter, and the like. Inducible and tissue specific expression of the nucleic acid operably linked thereto may be accomplished by placing the nucleic acid under the control of an inducible or tissue specific promoter/regulatory sequence. Examples of tissue specific or inducible promoter/regulatory sequences which are useful for this purpose include, but are not limited to the MMTV long terminal repeat (LTR) inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention should be construed to include the use of any promoter/regulator sequence which is either know or is heretofore unknown, which is capable of driving expression of the nucleic acid operably linked thereto.

One skilled in the art will appreciate, based upon the disclosure provided herein, that stem cells of the invention are useful for cell therapy. That is, such a stem cell would, when introduced into an animal, express the nucleic acid thereby providing a method of producing a protein (or disrupting expression of an undesired protein through the use of an interfering RNA), thus correcting a genetic defect in a cell, encode a protein which is not otherwise present in sufficient and/or functional quantity such that it corrects a genetic defect in the cell, and/or encodes a protein which is useful as a therapeutic in the treatment or prevention of a particular disease condition or disorder or symptoms associated therewith. Thus, stem cells of the invention are useful therapeutics allowing the expression of an isolated nucleic acid present in such cell.

Stem cells of the invention can be genetically modified to express one or more RNA interference (RNAi) molecules when administered to a patient (e.g., a human). RNAi is a mechanism that inhibits gene expression by causing the degradation of specific RNA molecules or hindering the transcription of specific genes. Key to the mechanism of RNAi are small interfering RNA strands (siRNA), which have complementary nucleotide sequences to a targeted messenger RNA (mRNA) molecule. siRNAs are short, single-stranded nucleic acid molecule capable of inhibiting or down-regulating gene expression in a sequence-specific manner; see, for example, Zamore et al., Cell 101:25 33 (2000); Bass, Nature 411:428-429 (2001); Elbashir et al., Nature 411:494-498 (2001); and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. Methods of preparing a siRNA molecule for use in gene silencing are described in U.S. Pat. No. 7,078,196, which is hereby incorporated by reference.

The application of RNAi technology (e.g., an siRNA molecule) in the present invention can occur in several ways, each resulting in functional silencing of a gene product in a stem cell population. The functional silencing of one or more endogenous stem cell gene products may increase the longevity the stem cell in vivo (e.g., by silencing one or more pro-apoptotic gene products), or increase the expression of a therapeutic polypeptide (e.g., an antibody, cytokine, or hormone).

Functional gene silencing by an RNAi agent (e.g., an siRNA molecule) does not necessarily include complete inhibition of the targeted gene product. In some cases, marginal decreases in gene product expression caused by an RNAi agent can translate to significant functional or phenotypic changes in the host cell, tissue, organ, or animal. Therefore, gene silencing is understood to be a functional equivalent and the degree of gene product degradation to achieve silencing may differ between gene targets or host cell type. Gene silencing may decrease gene product expression by 1%, 2%, 3%, 4%, 5%, 6%, 7%, 8%, 9%, or 10%. Preferentially, gene product expression is decreased by 10%, 20%, 30%, 40%, 50%, 60%, 70%, 80%, 90%, or 100% (i.e., complete inhibition).

Recombinant expression of non-endogenous polypeptides or oligonucleotides in stem cells of the invention can be accomplished by using any standard gene transfer technique, examples of which are discussed below.

In some embodiments, viral transduction can be used to genetically modify a stem cell of the invention. Many viruses bind and infect mammalian cells and introduce their genetic material into the host cell as part of their replication cycle. Some types of viruses (e.g., retroviruses) integrate their viral genomes into the host's genome. This incorporates the genes of that virus among the genes of the host cell for the life span of that cell. In viruses modified for gene transfer, a donor gene (e.g., a humanized monoclonal antibody) is inserted into the viral genome. Additional modifications are made to the virus to improve infectivity or tropism (e.g., pseudotyping), reduce or eliminate replicative competency, and reduce immunogenicity. The newly-introduced mammalian gene will be expressed in the infected host cell or organism and, if replacing a defective host gene, can ameliorate conditions or diseases caused by the defective gene. Adenoviruses and retroviruses (including lentiviruses) are particularly attractive modalities for gene therapy applications, as discussed below, due to the ability to genetically-modify and exploit the life cycle of these viruses.

In some embodiments, an adenoviral vector is used. Recombinant adenoviral vectors offer several significant advantages for the expression of polypeptides (e.g., an antibodies, cytokines, or clotting factors) or oligonucleotides (e.g., an siRNA) in stem cells of the invention. The viruses can be prepared at extremely high titer, infect non-replicating cells, and confer high-efficiency and high-level transduction of target cells in vivo after directed injection or perfusion. Furthermore, as adenoviruses do not integrate their DNA into the host genome, there is a reduced risk of inducing spontaneous proliferative disorders. In animal models, adenoviral gene transfer has generally been found to mediate high-level expression for approximately one week. The duration of transgene expression may be prolonged, and ectopic expression reduced, by using tissue-specific promoters. Other improvements in the molecular engineering of the adenoviral vector itself have produced more sustained transgene expression and less inflammation. This is seen with so-called "second generation" vectors harboring specific mutations in additional early adenoviral genes and "gutless" vectors in which virtually all the viral genes are deleted utilizing a cre-lox strategy (Engelhardt et al., Proc. Natl. Acad. Sci. USA 91:6196-6200 (1994) and Kochanek et al., Proc. Natl. Acad. Sci. USA 93:5731-5736 (1996)). In addition, recombinant adeno-associated viruses (rAAV), derived from non-pathogenic parvoviruses, can be used to express a polypeptide or oligonucleotide, as these vectors evoke almost no cellular immune response, and produce transgene expression lasting months in most systems. Incorporation of a tissue-specific promoter may also be beneficial.

Other viral vectors useful for the delivery of polypeptides or oligonucleotides into a subject or cells are retroviruses, including lentiviruses. As opposed to adenoviruses, the genetic material in retroviruses is RNA, while the genetic material of their hosts is in the form of DNA. When a retrovirus infects a host cell, it introduces its RNA together with enzymes into the cell. This RNA molecule is used to produce a double-stranded DNA copy (provirus) by reverse transcription. Following transport into the cell nucleus, the proviral DNA is integrated in a host chromosome, permanently altering the genome of the infected cell and any progeny cells that may arise. Retroviruses include lentiviruses, a family of viruses including human immunodeficiency virus (HIV) that includes several accessory proteins to facilitate viral infection and proviral integration.

One problem with using retroviruses for gene therapy is that the integrase enzyme can insert the genetic material of the virus in an arbitrary position in the host genome, risking gene disruption (e.g., insertional mutagenesis). If the gene happens to be one regulating cell division, uncontrolled cell division (e.g., cancer) can occur. To address this problem, inclusion of zinc finger nucleases or certain sequences, such as the beta-globin locus control region, are used to direct the site of integration to specific chromosomal sites. Current, "third-generation" lentiviral vectors feature total replication incompetence, broad tropism, and increased gene transfer capacity for mammalian cells (see Mangeat et al., Human Gene Therapy 16:913-920 (2005) and Wiznerowicz et al., Trends Biotechnol. 23:42-7 (2005)). Lentiviruses pseudotyped with, e.g., vesicular stomatitis virus glycoprotein (VSV-G) or feline endogenous virus RD114 envelope glycoprotein can be used to transduce stem cells of the invention. (see, e.g., Zhang et al., J. Virol. 78:1219-1229 (2004)). U.S. Pat. Nos. 5,919, 458, 5,994,136, and 7,198,950, hereby incorporated by reference, describe the production and use of lentiviruses to genetically modify target cells.

Besides adenoviral and retroviral vectors, other viral vectors and techniques are known in the art that can be used to transfer a DNA vector (e.g., a plasmid) encoding a desired polypeptide or oligonucleotide into a subject or cells. These include, e.g., those described by Wattanapitayakul and Bauer (Biomed. Pharmacother 54:487-504 (2000), and citations therein.

Other transfection approaches, including naked DNA or oligonucleotides (e.g., DNA vectors such as plasmids) encoding polypeptides (e.g., an antibody, cytokine, or hormone) or RNA interference molecule (e.g., an siRNA or shRNA), can be used to genetically modify stem cells of the invention. Improved transfection efficiency of naked DNA can be achieved using electroporation or a "gene gun," which shoots DNA-coated gold particles into the cell using high pressure gas.

To improve the delivery of a DNA vector (e.g., a plasmid) into a stem cell of the invention, the DNA can be protected from damage and its entry into the cell facilitated, for example, by using lipoplexes and polyplexes. Plasmid DNA can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Hybrid methods have been developed that combine two or more techniques described above. Virosomes, for example, combine liposomes with an inactivated virus. This approach has been shown to result in more efficient gene transfer in respiratory epithelial cells than either viral or liposomal methods alone. Other methods involve mixing other viral vectors with cationic lipids or hybridising viruses. Each of these methods can be used to facilitate transfer of a DNA vector (e.g., a plasmid) into a stem cell of the invention.

Dendrimers, a highly branched macromolecule with a spherical shape, may be also used to genetically modify stem cells of the invention. The surface of the dendrimer particle may be functionalized to alter its properties. In particular, it is possible to construct a cationic dendrimer (i.e., one with a positive surface charge). When in the presence of genetic material such as a DNA plasmid, charge complimentarity leads to a temporary association of the nucleic acid with the cationic dendrimer. On reaching its destination, the dendrimer-nucleic acid complex can be taken into a stem cell of the invention by endocytosis.

Toxicology Screening

Stem cells of the invention may also be used in toxicity screening. For example, assays can be used to test the potential toxicity of compounds on stem cells of the invention or the differentiated progeny thereof. In one example, where the stem cells of the invention are differentiated into the hematopoietic lineage, hematopoietic stem cells and progenitor assays can be used as to investigate growth and differentiation of cells in response to positive and negative regulators of hematopoiesis. These assays provide the opportunity to assess the potential toxicity of compounds on specific hematopoietic (e.g. myeloid, erythroid) cell populations.

U.S. Pat. No. 7,166,277, incorporated by reference in its entirety herein, describes a method of generating neural cells for the purposes of drug screening of putative therapeutic agents targeted at the nervous system. Such screening methods can be applied to stem cells of the invention which have been differentiated into neuronal cell types.

Other approaches include, prior to applying the drug, transforming the cells with a promoter activated by metabolic or toxicologic challenge operably linked to a reporter gene. Exemplary promoters include those which respond to apoptosis, respond to DNA damage, respond to hyperplasia, respond to oxidative stress, are upregulated in liver toxicity, are responsive to receptors that act in the nucleus, upregulate hepatocyte enzymes for drug metabolism, are from genes which are deficient in particular disease conditions, and genes which regulate synthesis, release, metabolism, or reuptake of neurotransmitters. See, for example, the methods and exemplary promoters in U.S. Patent Application Publication No. 2006/0292695.

In preferred embodiments, for example, stem cell progeny of a selected cell type can be cultured in vitro can be used for the screening of potential therapeutic compositions. These compositions can be applied to cells in culture at varying dosages, and the response of the cells monitored for various time periods. Physical characteristics of the cells can be analyzed, for example, by observing cell growth with microscopy. The induction of expression of new or increased levels of proteins such as enzymes, receptors and other cell surface molecules, or other markers of significance (e.g., neurotransmitters, amino acids, neuropeptides and biogenic amines) can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Preservation

Once isolated and/or purified, it may be desirable to preserve the stem cells of the invention. Cell can be preserved by freezing in the presence of a cryoprotectant, i.e., an agent that reduces or prevents damage to cells upon freezing. Cryoprotectants include sugars (e.g., glucose, trehalose), glycols such as glycerol (e.g., 5-20% v/v in culture media), ethylene glycol, and propylene glycol, dextran, and dimethyl sulfoxide (DMSO) (e.g., 5-15% in culture media). Appropriate freezing conditions (e.g., 1-3° C. per minute) and storage conditions (e.g., between −140 and −180° C. or at −196° C. such as in liquid nitrogen) can be determined by one of skill in the art.

Other preservation methods are described in U.S. Pat. Nos. 5,656,498, 5,004,681, 5,192,553, 5,955,257, and 6,461,645.

Methods for banking stem cells are described, for example, in U.S. Patent Application Publication No. 2003/0215942.

EXEMPLIFICATION

The following examples are intended to illustrate, rather than limit, the invention.

Example 1

Purifying and Enriching Stem Cells from Synovial Fluid

In a first step, freshly isolated synovial fluid was obtained from an osteoarthritic (OA) patient. Synovial fluid mononuclear cells were thus derived from joint aspirates. Joint aspirates can be obtained by standard methods well known to those of skill in the art.

Harvesting ELA Stem Cell™ (Heterogenous Population).

Synovial fluid from OA patients was harvested, diluted in serum-free medium (AIM-V, GIBCO) or MCDB, MEM, IMDM, RPMI media, and spun at 200 g for 15 minutes at room temperature (RT). The pelleted population was then resuspended in AIM-V up to the original synovial fluid volume. The mononuclear cell number from the synovial fluid ranged between 500,000 to 5 million heterologous mononuclear cells.

Harvesting ELA Stem Cells™ (Homogenous Population)

The pelleted population was then resuspended in AIM-V, serum free medium developed for the ex vivo expansion of human lymphocytes, up to the original synovial fluid volume, counted, washed, and layered over a discontinuous density gradient (ROSETTE SEP DM-M, Stem Cell Technologies). The Rosette discontinuous density gradient does not allow granulocytes to pellet with smaller cells, for example, cells smaller than 2 micrometers to about 6 micrometers (μm) in diameter. In this regard, the gradient is different from, for example, a FICOLL gradient.

Next, the cells were spun for 500 g (2500 RPM) for 30 minutes at room temperature. This characteristic allows only two populations of cells, RBC and stem cells, to pellet, which is useful when enriching for stem cells from bone marrow aspirate. The DM-M separates SF mononuclear cells into a buffy layer, which is found at the AIM-V and ficoll interface, and a pelleted layer which is found at the bottom of the conical portion of the tube.

Immunomagnetic Bead Enrichment

Stem cells of the invention do not express major histocompatibility antigen class I (MHC I) or erythroblast specific glycophorin-A (Gly-A). Therefore, the separated cells were subjected to negative selection using anti-class I, CD66b, and anti-Gly-A antibodies. This negative selection step depletes the population of class I, CD66b, and glycophorin A cells, and recovers the remaining populations, which are from about 5% to 30% of the Oct-4 protein expressing cells, and from about 1-10% marrow, blood, and tissue mononuclear cells. Cells were resuspended in blocking buffer and incubated with anti-MHC class I, anti-CD66b, and anti-glycophorin b, immunomagnetic beads for 30 minutes at 4° C. Following incubation, samples were washed and resuspended in medium at a $10^5$-$10^6$ cells per ml and passed through a magnetic field to remove cells bound to immunomagnetic beads.

Example 2

Characterization and Expansion of Enriched or Sorted ELA Stem Cells™

Both populations of separated cells (i.e., from the buffy layer or the pellet) were incubated with anti-MHC class I, anti-CD66b, and anti-glycophorin b, immunomagnetic beads as described above. Samples were first assessed for the expression of MHC class I, MHC class II, CD44, CD45, CD13, CD34, CD49c, CD66b, CD73, CD105 and CD90 cell surface markers and then permeabilized to determine the presence of Oct-4, Nanog, Sox-2, Rex-1, GDF-3, and Stella intracellularly. FIGS. 1a-1e are dot plots of the enriched cells, sorted into 3 groups (e.g., Group-A, -B, and -C) and analyzed for Oct-4, Rex-1, Runx2, Sox-9, Nanog, Class I, CD44, and CD45 expression. Six to thirty percent of total mononuclear population, i.e., groups A and B, expressed Oct-4, Nanog, Sox-9, and Rex-1 while group C expressed the aforementioned transcription factors at high levels, with the exception of Oct-4. The majority of the cells were negative for the above cell surface and intracellular markers, as shown in FIGS. 1a-1e. Evaluation of the mononuclear cell fraction by PCR revealed Nanog, Oct-4, Rex-1, and Sox-2 gene expression (FIG. 2). The molecular weight of the synovial fluid transcripts were similar in size to the transcripts expressed by the Ntera-2 embryonic carcinoma cell line. Cells isolated according to the methods described herein above, which fail to express detectable levels of the aforementioned cell surface markers, but express embryonic stem cell genes, are referred to as ELA Stem Cells™. Accordingly, the ELA Stem Cells™ express embryonic stem cell genes.

Example 3

Propagation of ELA Stem Cells™

Figure 3B:
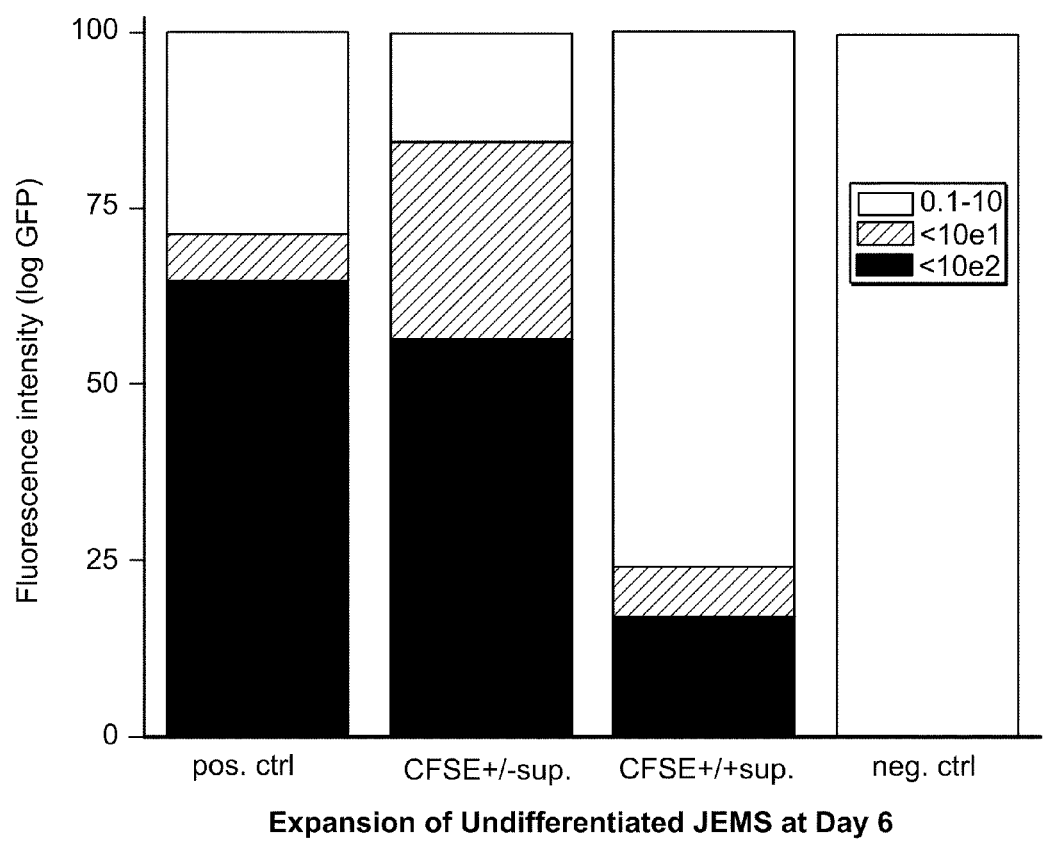
In FIG. 3b, freshly isolated stem cells were pulsed with carboxyfluorescein diacetate, succinimidyl ester (CFSE) and the percent positive was assessed after 6 days; the white bar region represents the percentage of highly proliferative stem cells, the stripped bar region represents the percentage of moderately proliferative stem cells, and black bar region represents the percentage of nonproliferative stem cells.

Heterogenous or homogenous populations of ELA Stem Cells™ not incubated with immunomagnetic beads were plated onto culture dishes coated with about 7-10 ng/ml serum fibronectin or other appropriate matrix coating. Cells were maintained in Dulbecco Minimal Essential Medium (DMEM) or 40-60% (e.g., 60%) Low Glucose DMEM and 40-60% (e.g., 40%) MCDB-201 medium supplemented with 1-50 ng/ml (e.g., about 5-15 ng/ml or 10 ng/ml) platelet-derived growth factor-BB (PDGF-BB), 1-50 ng/ml (e.g., about 5-15 ng/ml or 10 ng/ml) epidermal growth factor (EGF), 1-50 ng/ml (e.g., about 5-15 ng/ml or 10 ng/ml) insulin-like growth factor (IGF), or 100-10,000 IU (e.g., about 1,000) LIF, with $10^{-11}$ to $10^{-8}$ M (e.g., 0.01 nM) dexamethasone or other appropriate steroid(s), 2-10 μg/ml (e.g., 4.7 ng/ml) linoleic acid, and 0.05-0.15 μm (e.g., 0.1 μm) ascorbic acid. The culture medium may further include 10-50 ng/ml (e.g., 10 ng/ml) insulin, 0-10 ng/ml (e.g., 5.5 ng/ml) transferrin, and 2-10 ng/ml (e.g., 5 ng/ml) selenium. The cells can either be maintained without serum, in the presence of 1-2% fetal calf serum, or, preferably in 1-2% human AB serum or autologous serum. After 3 days, small colonies of adherent cells developed, and by days six and nine, the cells became semi-confluent (FIG. 3a). Freshly isolated ELA Stem Cells™ were pulsed with CFSE and the percentage of negative cells was assessed after 6 days. FIG. 3b demonstrates the proliferation capacity of ELA Stem Cells™.

Example 4

Formation of Embryoid Bodies

Stem cells of the invention can form embryoid bodies or colony forming units in culture using standard protocols. In one example, commercially available culture medium suitable for culturing endothelial cells (EndoCult® Liquid Medium) is added to a fibronectin-coated plate (Becton-Dickenson (BD) Biosciences Discovery BD Catalog No.

354402). $5\times10^6$ cells are plated per well in the 6-well fibronectin-coated plate and incubated for two days at 37° C., 5% $CO_2$ with >95% humidity. After two days, numerous cell populations including mature endothelial cells and some monocytes adhere to the bottom of the well. The non-adherent cells will contain the CFU-Hill colony-forming cells, which are then harvested and further cultured for an additional 3 days to allow formation of CFU-Hill colonies. The non-adherent cells are collected by pipetting the medium in each well up and down vigorously 3-4 times to remove any non-adherent cells transiently attached to the adherent population. The non-adherent cells from each well are transferred into individual 5 ml tubes (BD Catalog No. 352058). The volume from each well is measured, e.g., using a 2 ml pipette. Nucleated cells are counted using 3% acetic acid with Methylene Blue (StemCell Technologies, Inc., Catalog No. 07060) using a hemacytometer. Approximately $3.0\text{-}3.5\times10^6$ cells are expected from one well of a 6-well plate. From each well, $1\times10^6$ cells/well are added to a 24-well fibronectin-coated plate (BD Catalog No. 354411). Fresh EndoCult® Liquid Medium is added to a final volume of 1.0 ml per well. The cells are then incubated at 37° C., 5% $CO^2$ with >95% humidity for three days. Colonies of cells can then be observed.

Example 5

Differentiation

Stem cells of the invention were further characterized to assess their differentiation potential. As an example, after separation from synovial fluid as described in Example 1, the pelleted mononuclear population of stem cells was cultured in 24-well plates at $10^5$ cell per well. After 6-9 days in standard culture medium, lineage-specific differentiation agents were added to culture. The medium was changed every 3-4 days and after 14 or 21 days, cultures were evaluated. The committed or differentiated cells of the invention may be used in the transplantation methods described above.

Stem cells can also be differentiated using RNAi based methods. In one example, trophectoderm production is achieved by transfection of stem cells with OCT-4- or Nanog-targeted RNAi compounds, which reduces the levels of OCT-4 or Nanog transcripts and proteins. Reduction in OCT-4 expression correlated with induction of trophectoderm genes Cdx2, Hand1, and PL-1, with formation of cells with trophoblast giant cell phenotype after 6 days. Reduction in Nanog expression can correlate with induction of extraembryonic endoderm genes GATA4, GATA6, and laminin B1, with subsequent generation of groups of cells with parietal endoderm phenotype. Appropriate RNAi constructs for differentiation into other tissue types can be determined by one of skill in the art.

Differentiation may be carried out by any means known in the art. Exemplary differentiation procedures are described below.

Osteoblast Differentiation

Figure 4:
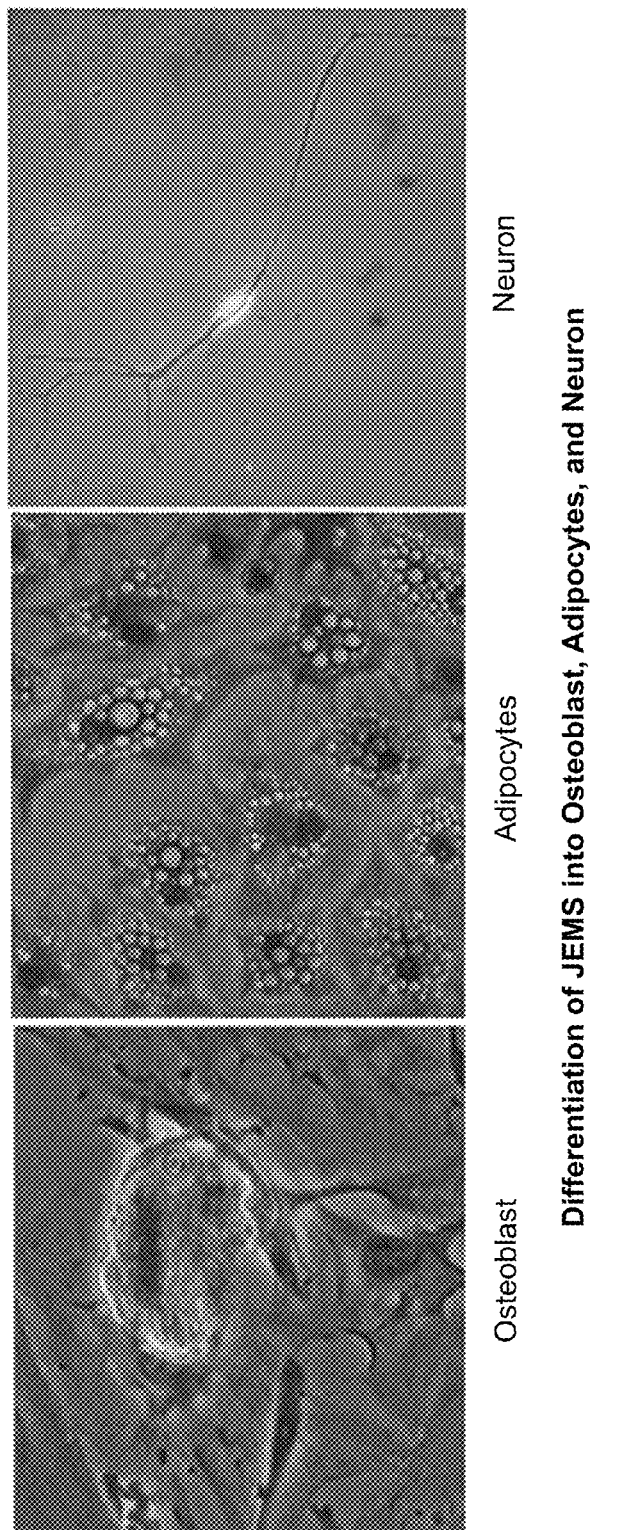
FIG. 4 shows differentiation of stem cells into osteoblasts, adipocytes, and a neuron.
Figure 5:
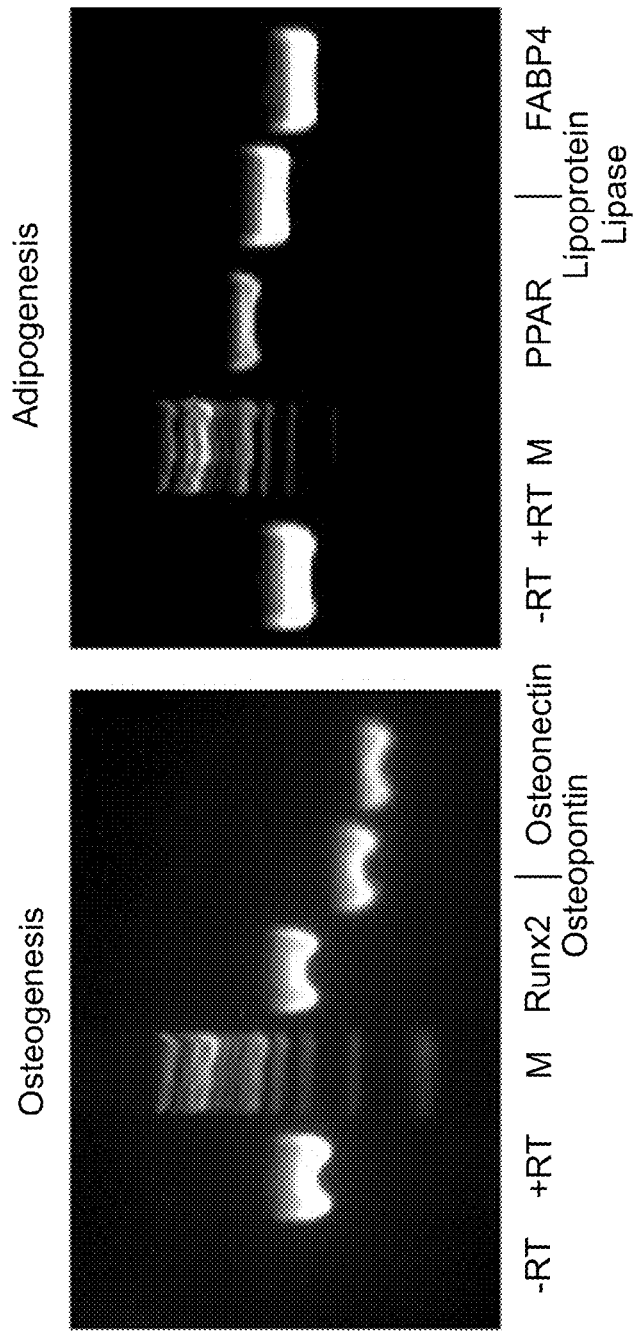
FIG. 5 shows expression of osteoblast- or adipocyte-specific genes in differentiated JEMS.

FIG. 4 (left panel) shows an example of osteoblast differentiation. Here, stem cells of the invention were plated into 24-well plates at $10^5$ cells per $cm^2$ in Cambrex MSC medium for 1 week. On the following day, the medium was replaced with fresh α-MEM containing 10% heat-inactivated FBS, 1% nonessential amino acids, 1% penicillin and streptomycin, 10 mM α-glycerophosphate, and 50 μM ascorbic acid 2-phosphate, with medium changes every 3-4 days. Differentiated stem cells were assayed for alkaline phosphatase activity and mineral deposition by histochemical staining with the Sigma Kit 85 and Alizarin red methods, respectively, at day 14 (Pittenger et al. (1999) Science; 284:143-147).

Osteoblasts can also be differentiated as follows. Medium from the cell monolayer is pipetted and discarded. The monolayer is washed with DPBS (Thermo Scientific HyClone ESQualified DPBS, Catalog No. SH30850.03) by adding 10 ml/75 $cm^2$ to the flask, being careful not to disturb the monolayer. The flask is rocked back and forth. The DPBS is then removed from the monolayer and discarded. Trypsin (Thermo Scientific HyClone Trypsin, Catalog No. SH30042.01) was added at 3-5 mL/75 $cm^2$ flask and rocked to cover the monolayer with the trypsin solution. Cells are incubated at 37° C. until the cells begin to detach (approximately 5 minutes, but not more than 15 minutes). Complete Mesenchymal Stem Cell Expansion Medium 90% Thermo Scientific AdvanceSTEM™ Mesenchymal Stem Cell Basal Medium, Catalog No. SH30879.02, and 10% Thermo Scientific AdvanceSTEM™ Stem Cell Growth Supplement, Catalog No. SH30878.01) is added in equal amounts to trypsin, and the cells are pipetted up and down to form a single cell suspension. The trypsin is removed by centrifuging the cells at approximately 200 g for 10 minutes at room temperature and removing the supernatant. The cell pellet is re-suspended in prewarmed complete Mesenchymal Stem Cell Expansion Medium at approximately 5 ml/pellet for a 75 $cm^2$ flask. A small cell sample is removed and counted with a hemacytometer or cell counter. The cells are then plated on a fresh tissue culture dish at 80-90% confluency using complete Mesenchymal Stem Cell Expansion Medium. The cells are allowed to attach for at least 24 hours or until normal morphology is observed. Once the cells have attached and this level of confluency is reached, the medium is removed, the cells are rinsed with two rinses of DPBS, and an appropriate amount of complete Osteogenic Differentiation Medium (90% Thermo Scientific AdvanceSTEM Osteogenic Differentiation Medium, Catalog No. SH30881.02, and 10% Thermo Scientific AdvanceSTEM Stem Cell Growth Supplement, Catalog No. SH30878.02) is added. For a 60 mm dish, about 7 ml is sufficient. The cells are then incubated at 37° C., 5% $CO_2$, with humidity. The medium is replaced every 3 days and osteogenesis typically takes approximately 21-28 days. Formation of osteoblasts and mineralized matrix can be detected by staining protocols known in the art.

In yet another protocol, stem cells are plated at 3,000 cells/$cm^2$ and cultured in the expansion media described above overnight. The following day, the medium is replaced with fresh α-MEM, 10% pooled human serum (PHS), 1% non-essential amino acids, 1% Pen-Strep, 10 mM β-glycerophosphate, and 50 μM ascorbic acid 2-phosphate, with media being changed every 3-4 days until osteoblasts form.

Exemplary methods for forming bone are also described in U.S. Pat. No. 6,863,900, which describes enhancing bone repair by transplantation of mesenchymal stem cells. ELA Stem Cells™ will respond similarly to mesenchymal stem cells when exposed to the same methodology as described in U.S. Pat. No. 6,863,900. To further enhance bone formation it may be desirable to inhibit osteoclastogenesis, i.e., cells which decrease bone mass. Such methods are described in U.S. Pat. No. 6,239,157. Stem cells of the invention may also be used to augment bone formation by administration in conjunction with a resorbable polymer, e.g., as described in U.S. Pat. No. 6,541,024.

Adipocyte Differentiation

FIG. 4 (middle panel) shows an example of adipocyte differentiation. Here, adipocyte differentiation was induced using a commercially available adipocyte differentiation kit (Cambrex, East Rutherford, N.J.) according to the manufacturer's recommendations. Differentiated cells were evaluated by oil red O stain. ELA Stem Cells™ were suspended in Mesenchymal Stem Cell Expansion Medium at a density of 100,000 cells per well in a 24-well culture dish with 1 ml volume per well and incubated overnight at 37° C. in a 5% $CO_2$ humidified incubator. When the cells were 100% confluent, medium was removed from each well and replaced with 0.5-1 ml Adipogenesis Induction Medium (DMEM ~90%, heat inactivated fetal bovine serum 10%, 1 μM dexamethasone, 0.5 mM IBMX, 10 μg/ml insulin, 100 μM indomethacin, 1× penicillin and streptomycin). The Adipogenesis Induction Medium was replaced every 2-3 days for 21 days. Lipid droplets were detected by microscopic examination as early as 5 days into the differentiation period. After 21 days of differentiation, adipocytes were fixed and the lipid droplets stained with Oil Red O Solution.

In another example, adipocyte differentiation may be achieved as follows. Adipocytes can also be generated using the Thermo Scientific HyClone AdvanceSTEM™ Adipogenic Differentiation Kit. In this procedure, spent media from cultured cells is pipetted from the cell monolayer and discarded. The cell monolayer is then washed with Dulbecco's Phosphate Buffered-Saline (Thermo Scientific HyClone ESQualified DPBS Catalog No. SH30850.03) by adding 10 ml/75 $cm^2$ to the flask, being careful not to disturb the monolayer. The flask is rocked back and forth, and then the DPBS is removed from the monolayer and discarded. Trypsin (e.g., Thermo Scientific HyClone Trypsin (Catalog No. SH30042.01)) is added at 3-5 ml/75 $cm^2$ flask. The flask is rocked to ensure that the entire monolayer is covered with the trypsin solution, and incubated at 37° C. until the cells begin to detach (about 5 minutes), but no more than 15 minutes. Care should be taken that the cells are not forced to detach prematurely, as this may result in clumping. Next, complete Mesenchymal Stem Cell Expansion Medium (90% Thermo Scientific AdvanceSTEM™ Mesenchymal Stem Cell Basal Medium (Catalog No. SH30879.02) and 10% Thermo Scientific AdvanceSTEM™ Stem Cell Growth Supplement (Catalog No. SH30878.01)) are added in equal amounts to the trypsin solution and the solution is pipetted up and down until the cells are dispersed into a single cell suspension. Next, the trypsin is removed by centrifuging the cells at approximately 200 g for 10 minutes at room temperature, and the supernatant is removed. The cell pellet is then re-suspended in prewarmed complete Mesenchymal Stem Cell Expansion Medium at approximately 5 ml/pellet for a 75 $cm^2$ flask. A small volume sample is then removed for counting with a hemacytometer or cell counter. The cells are then plated on a fresh tissue culture dish at 80-90% confluency using complete Mesenchymal Stem Cell Expansion Medium. The cells are allowed to attach for a minimum of 24 hours, or until normal morphology is observed. Once the cells have attached and this level of confluency is reached, the Mesenchymal Stem Cell Expansion Medium is removed, the cells are rinsed with two rinses of DPBS, and Adipogenic Differentiation Medium is added (90% Thermo Scientific AdvanceSTEM™ Adipogenic Differentiation Medium (Catalog No. SH30886.02) and 10% Thermo Scientific AdvanceSTEM™ Growth Supplement (Catalog No. SH30878.02)). The amount of medium will vary depending on the size of the culture dish being used; for a 60 mm dish, about 7 ml is sufficient. The cells are then incubated 37 C, 5% $CO_2$, with humidity. Every 3 days the media is removed and replaced with fresh complete Adipogenic Differentiation Medium. Adipogenesis can then be observed as formation of lipid droplets, generally within 7 days, peaking at 3-4 weeks.

Other commercially available adipocyte kits include Chemicon SCR020.

In another embodiment, adipogenic differentiation is achieved by seeding cells at $10^4$ cells per $cm^2$. First, at confluence, cells are put in D10 medium and supplemented with 1 μM dexamethasone, 0.2 mM indomethacin, 10 ng/ml insulin, and 0.5 mM 3-isobutyl-1-methyl-xanthine (all from Sigma-Aldrich). Medium is replaced every 3-4 days for 21 days. Cells are washed three times with PBS, fixed in 10% formalin for 1-2 hours, and stained for 15 minutes with fresh oil red O solution (Sigma-Aldrich) to detect adipocyte formation.

Adipocytes can also be differentiated on a solid support, as described in U.S. Pat. No. 6,709,864.

Neuroectoderm Differentiation

FIG. 4 (right panel) shows one example of ectodermal differentiation. ELA Stem Cells™ were plated in a FN-coated (10 ng/ml) 24-well plate at 3,000 or $10^5$ overnight in basal stem cell medium or expansion medium. The following day, 100 ng/ml bFGF, 10 ng/ml Noggin, 20 μM retinoic acid and cultures continued for 28 days. After 14 days, 10 ng/ml BDNF and GDNF were also added. Every 7 days, half of the medium was replaced until day 28.

Neural differentiation can be evaluated via Q-RT-PCR for early neural transcription factors, Islet-1 transcription factor, orthodenticle homolog 2 (Otx-2), and paired box gene 6 (Pax-6), as well as neural cell adhesion molecule and the more mature neuronal marker MAP2, NF200, tau, and myelin basic protein (MBP). Cultures can be further analyzed via immunofluorescence for NF200, MAP2, and GFAP.

Neural differentiation can also be achieved as follows. Spent medium from cell monolayer is discarded, and the cells are washed with Dulbecco s Phosphate Buffered Saline (DPBS) (Thermo Scientific HyClone ESQualified DPBS, Catalog No. CSH30850.03) by adding 10 ml/75 $cm^2$ to the flask, being careful not to disturb the monolayer. The flask is then rocked back and forth. Next, the DPBS is removed from the monolayer and discarded. Trysin (Thermo Scientific HyClone Trypsin, Catalog No. SH30042.01) is added at 3-5 ml/75 $cm^2$ to the flask which is rocked to ensure that the entire monolayer is covered with the trypsin solution. The flask is incubated at 37° C. until the cells begin to detach (approximately 5, but less than 15, minutes). Commercially available mesenchymal stem cell culture media (Complete Thermo Scientific HyClone AdvanceSTEM™ Mesenchymal Stem Cell Expansion Media (90% Thermo Scientific AdvanceSTEM™ Mesenchymal Stem Cell Basal Medium (Catalog No. SH30879.02) and 10% Thermo Scientific AdvanceSTEM™ Stem Cell Growth Supplement (Catalog No. SH30878.01)) is added in equal amounts to trypsin. The cells are then pipetted up and down to form a single cell suspension. The trypsin is removed by centrifuge cells at approximately 200 g for 10 minutes at room temperature and aseptically removing the supernatant. The cells are resuspended in prewarmed complete commercially available neural differentiation culture media (Thermo Scientific HyClone AdvanceSTEM Neural Differentiation Media (90% Thermo Scientific AdvanceSTEM Neural Differentiation Medium, Catalog No. SH30893.02 and 10% Thermo Scientific 50 ml AdvanceSTEM Stem Cell Growth Supplement, Catalog No. SH30878.02) at approximately 5 ml/pellet for a 75 $cm^2$ flask. A small sample is removed for counting with a hemacytometer or cell counter. On a fresh tissue culture dish, cells are plated at 30% confluency (approximately 2,500 cells/$cm^2$) using complete Mesenchymal Stem Cell Expansion Media. The cells are allowed to attach (e.g., for 24 hours or until normal morphology is seen). Once the cells have attached and this level of confluency is reached, the Mesenchymal Stem Cell Expansion Media is removed. The cells are rinsed with DPBS, and complete Neural Differentiation Media is added. For a 60 mm dish, for example, about 7 ml is sufficient. The cells are then incubated at 37° C., 5% $CO_2$, with humidity. Neural differentiation can be observed as formation of neuron-like cells, typically within 24 hours and peaking at 72 hours. To maintain cells in a differentiated state, the media is replaced every 48 hours.

Differentiation into neurons, astrocytes, and oligodendrocytes can also be achieved as follows. Poly-L-Ornithine coated glass coverslips are placed into individual wells of a 24-well culture dish (e.g., Corning Catalog No. 3526) containing 1 ml/well of commercially available neuron differentiation culture media "Complete" NeuroCult® NS-A Differentiation Medium (Human) (StemCell Technologies. If using BioCoat 8-well Culture Slides (pre-coated with Poly-D-Lysine/Laminin, StemCell Technologies Catalog No. 35-4688, or Poly-D-Lysine Catalog No. 35-4631), add 0.75 ml/well of "Complete" NeuroCult® NS-A Differentiation Medium (Human). Proliferating stem cells are then exchanged in to in "Complete" NeuroCult® NS-A Differentiation Medium (Human) using a 10 ml disposable plastic pipette and centrifuge, and repeat to remove the expansion media. The cells are counted using hemacytometer and standard protocols. The cells are then resuspended in an appropriate volume of "Complete" NeuroCult® NS-A Differentiation Medium (Human) to yield a plating cell density of 0.8-$1 \times 10^5$ cells/$cm^2$ in 0.75 ml medium on a coated coverslip in a 24-well dish (e.g., 0.9-$1.13 \times 10^5$ cells) or in a BioCoat 8-well Culture Slide (e.g., 0.56-$0.7 \times 10^5$ cells). The cells are incubated in a 5% $CO_2$ incubator at 37° C. After 5-10 days, the cultures are observed with an inverted light microscope to determine if cells have differentiated (attached) and are viable (phase contrast bright). Plates can be checked daily to determine if the medium needs to be changed during the differentiation procedure. If the medium becomes acidic (turns yellow), a half medium change is performed. Differentiation can be assessed using standard methods.

Chondroblast Differentiation of ELA Stem Cells™

Chondroblast differentiation was conducted according to methods known in the art. Such cells may be useful for repair of articular cartilage (e.g., due to injury), in prostheses or in joint (e.g., knee reconstruction), or for cosmetic purposes.

Stem cells of the invention ($10^5$ cells per $cm^2$) were cultured in 1 ml of basal medium (the expansion medium described herein above without serum, EGF, or PDGF) with 10 ng/ml TGF-β1 and 100 ng/ml BMP-4 in the tip of a 15-ml conical tube and briefly spun to allow aggregation of the cells in micromass suspension culture. After 9 days, cultures were evaluated by quantitative reverse-transcription-polymerase chain reaction (Q-RT-PCR) for collagen type II and aggrecan transcripts and stained with Alcian Blue to demonstrate cartilage matrix production.

Chondroblast differentiation was also conducted as follows. To induce chondrogenic differentiation, spent medium was pipetted from the cell monolayer and discarded. The monolayer was washed with DPBS (Thermo Scientific HyClone ESQualified DPBS (Catalog No. SH30850.03) by adding 10 ml/75 $cm^2$ to the flask, being careful not to disturb the monolayer. The flask was rocked back and forth. The DPBS was removed and discarded from the monolayer. Trypsin (Thermo Scientific HyClone Trypsin (Catalog No. SH30042.01) was added at 3-5 mL/75 cm2 flask and rocked to ensure coverage of the entire monolayer. The cells were incubated at 37° C. until they begin to detach (5 minutes, but less than 15 minutes). The trypsin was then removed by adding an equal volume of complete Chondrogenic Differentiation medium (90% Thermo Scientific AdvanceSTEM Chondrogenic Differentiation Medium (Catalog No. SH30889.02) and 10% Thermo Scientific AdvanceSTEM Stem Cell Growth Supplement (Catalog No. SH30878.01), spinning the cells for 10 minutes at 200 g in a swing bucket centrifuge and gently aspirating the supernatant. Next 4 ml of fresh complete Chondrogenic Differentiation medium was added to the tube without disturbing the pellet. The cap was then loosely fitted on top of the conical tube to allow gas exchange. The tube was then incubated at 37° C., 5% $CO_2$, with humidity. The media was replaced every 3 days without disturbing the pellet. Chrondrogenesis generally requires 28 days, which can be visualized, for example, by staining and microscopy.

Other methods for differentiation of chondrocytes are described in U.S. Pat. No. 5,908,784. Here, chondrocytes are differentiated culture by culture in a cell pellet, optionally with a corticosteroid such as dexamethasone. Other methods include the use of TGF-β or BMPs such as BMP-2, BMP-12 and BMP-13, with or without ascorbate for chondrocyte differentiation, as described in U.S. Pat. No. 5,919,702. Any of these cultures may be performed in three-dimensional culture, as known in the art.

Myocardiocyte Differentiation:

Myocardiocyte differentiation is accomplished by adding basic fibroblast growth factor to the standard serum-free culture media without growth factors. Confluent stem cells are exposed to 5-azacytidine and to retinoic acid and cultured in stem cell expansion medium afterwards. Alternatively, stem cells are cultured with either of these inducers alone or a combination and then cultured in serum-free medium with FGF-2 or BMP-4. Cultures are assessed for expression of any of Gata4, Gata6, cardiac troponin-T, cardiac troponin-1, ANP, Myf6 transcription factor, desmin, myogenin, and skeletal actin.

Endothelial Cell Differentiation

Endothelial cell differentiation can be conducted according to methods known in the art. Stem cells of the invention can be plated at 0.5-1.0 $10^5$ cells/$cm^2$ in basal medium (described above) with 100 ng/ml of VEGF-165 for 14 days. During the differentiation course, medium can be changed every 3-4 days. Differentiation cultures can be evaluated by Q-RT-PCR for VWF, CD31/Pecam, fms-like tyrosine kinase-1 (Flt-1), fetal liver kinase-1 (Flk-1), VE-cadherin, tyrosine kinase with Ig, and EGF homology domains 1 (Tie-1) and tyrosine kinase endothelial (Tek), every 3 days until day 10. Differentiated endothelial cells are stained for CD31, VWF, VE-cadherin, and VCAM-1 and evaluated for their ability to form tubes on ECMatrix and uptake acetylated low density lipoprotein (a-LDL). Tube formation can be induced by plating the differentiated endothelial cells according to the ECM625 angiogenesis assay (Chemicon) per the manufacturer's recommendations, and a-LDL uptake was performed by using Dil-Ac-LDL staining kit (Biomedical Technologies, Stoughton, Mass.) per the manufacturer's recommendations. Briefly, differentiated stem cells can be incubated with endothelium differentiation medium containing 10 μg/ml 1,1\'-dioctadecyl-3,3,3\',3\'-tetramethyl-indocarbocyanine perchlorate (Dil)-Ac-LDL for 4 hours at 37° C. and rinsed twice by Dil-Ac-LDL free endothelium medium. LDL uptake was visualized via fluorescence microscopy.

Hepatocyte Differentiation

Hepatocyte differentiation can be conducted according to methods known in the art. Hepatocyte differentiation will be achieved by plating 0.5-1.0 $10^5$ cells/$cm^2$ of stem cells on 2% Matrigel-coated (BD354234; BD Biosciences, San Diego)

plastic chamber slides in basal medium (described above) with 100 ng/ml FGF-4 and HGF for 15 days. During the differentiation course, medium can be changed every 3 days as needed. Differentiation cultures can be evaluated by Q-RT-PCR for HNF-3, HNF-1, CK18 and CK19 albumin, and CYB2B6 every 3 days until day 12. Differentiated cells can be evaluated by immunofluorescence microscopy for albumin, CK18, and HNF-1 protein expression. To assess the function of hepatocyte-like cells, karyotyping, telomere length, and telomerase activity measurements can be performed. Karyotyping can be conducted by plating enriched cells at 500 cells per $cm^2$ 48 hours prior to harvesting, followed by 10 µl/ml colcemid incubation for 2-3 hours. After collection with 0.25% Trypsin-EDTA cells can be lysed with a hypotonic solution and fixation in alcohol. Metaphases can be analyzed after Giemsa staining. For the telomerase assay, equal numbers of enriched cells can be lysed in 1×3-[(3-cholamidopropyl)dimethylammonio]-1-propanesulfonic acid (CHAPS) buffer for 10 minutes on ice. Debris can then be pelleted at 13,000 g for 10 minutes. Protein can be quantified by the method of Bradford. One to two µg of protein can be used in the telomere repeat amplification protocol (TRAP). The TRAP protocol, which uses an enzyme-linked immunosorbent assay (ELISA)-based detection system to determine telomerase activity, can be done according to the manufacturer's instructions (Chemicon). Positive activity is defined as OD 450-690 reading >0.2 of test samples after subtracting heat-inactivated controls.

Smooth Muscle Cell Differentiation

Smooth muscle cell differentiation can be conducted according to methods known in the art. For example, stem cells of the invention can be plated into 24-well plates at 3000 or $10^5$ cells/$cm^2$ in basal medium (described above) supplemented with 10 ng/ml PDGF and 5 ng/ml TGF-β1. During the differentiation course, medium can be changed every 3-4 days as needed. Smooth muscle cell (SMC) differentiation can be evaluated by RT-PCR for calponin, SM actin, smoothelin, gata-6, and myocardin and immunofluorescence (IF) staining for calponin, SM actin, sm22, and caldesmon.

Skeletal Muscle Cell Differentiation

Stem cells of the invention can also be differentiated into skeletal muscle tissue. In one example, 5-Azacytidine can be used to differentiate stem cells of the invention into muscle cells. Stem cells can be plated in a variety of densities of 1-4×$10^4$ cells per $cm^2$ on glass or TPX slides coated with fibronectin, Matrigel, gelatin, or collagen (Stem Cell Technologies). The cells can then be exposed to concentrations of 5-azacytidine (e.g., 1-24 µM) for 6-48 hours duration in either 2% human serum, FBS, or serum-free medium (defined as DMEM with 2 mM L-glutamine, 50 U/ml penicillin, 50 µg/ml streptomycin supplemented with 10 ng/ml platelet-derived growth factor-BB, and epidermal growth factor (Sigma-Aldrich) and ITS-plus (Fisher Scientific International). In some experiments, cells received a further 24-hour exposure to 5-azacytidine 3 days later. Following 5-azacytidine exposure, cells were maintained in serum-free medium for up to 21 days. To augment differentiation after a few days, human serum with dexamethasone and hydrocortisone, myoblast-Conditioned medium, or Galectin-1 may be added.

Myogenic differentiation can be observed by morphological criteria and immunostaining for desmin and sarcomeric myosin. Myogenic conversion can be assessed by counting the number of cells positive for desmin and MF20, Pax7, MyoD, and Myogenin expression can be similarly assessed using immunocytochemical staining.

Pancreatic Islet-Like Differentiation

Stem cells of the invention are plated onto gelatinized dishes in the presence of LIF, in expansion medium or other appropriate maintenance medium (e.g., DMEM containing 15% FBS, 1 mM sodium pyruvate, 100 U/ml penicillin, 100 µg/ml streptomycin, 2 mM glutamine, 0.1 mM Non-essential amino acids (StemCell Technologies, Catalog No. 07100), 10 ng/ml LIF, 100 µm MTG). The cells are allowed to grow for two days. Next, Differentiation Medium (15% Fetal Bovine Serum 0.1 mM MEM Non-Essential Amino Acids (StemCell Technologies, Catalog No. 07600) 2 mM L-Glutamine, and 1 mM MTG in High Glucose DMEM) is added low adherent dishes (e.g., Ultra-Low Adherent dishes, StemCell Technologies). The stem cells are trypsinized, and resuspended in Differentiation Medium, and plated onto the low adherent plates. On the second day, the medium is exchanged for fresh Differentiation Medium. The culture continues for 4 days. Next, nestin positive cells are enriched. The cells are transferred to a 14 ml polystyrene tube, and allowed to settle (3-5 min). The media is removed, and replaced with ES-Cult Basal Medium-A (StemCell Technologies Catalog No. 07151) supplemented with a commercially available preparation of insulin, transferrin, sodium selinte (ITS). The cells are then plated, and cultured for six days, changing media every two days. The medium is then removed, the cells are washed with PBS. Cells are then trypsinized, and the medium is replaced with Pancreatic Proliferation Medium (1×N2 Supplement-A (Catalog No. 07152), 1×B27 Supplements 50× (Catalog No. 07153), 25 ng/ml recombinant human FGF-b (Catalog No. 02634), and ES-Cult™ Basal Medium-A (Catalog No. 05801) to final volume of 100 ml). The cells are counted and seeded at 5×$10^5$ cells/ml media in a 24 well dish. Media is changed every 2 days for 6 days total. On the sixth day, the medium is replaced with Pancreatic Differentiation Medium (1×N2 Supplement-A, 1×B27 Supplements, 10 mM nicotinamide (Catalog No. 07154), ES-Cult™ Basal Medium-A to final volume of 100 ml). After six days, the insulin production can be detected (e.g., by ELISA).

Other methods for pancreatic cell differentiation can be found in U.S. Pat. No. 6,022,743.

Bone and Bone Cell Production

Stem cells of the invention may also be cultured under conditions which result in production of bone or bone cells, and related compositions. Such cells and compositions may be useful, for example, in treating bone diseases such as osteoporosis or to treat injuries to bone.

Bone Marrow Production

Stem cells of the invention may also be used to produce bone marrow or to enhance bone marrow engraftment. Exemplary procedures are described in U.S. Pat. Nos. 5,733,542 and 5,806,529.

Hematopoietic Stem Cell Production

Stem cells of the invention may also be cultured under conditions that form hematopoietic stem cells. Exemplary methods for doing so are described in U.S. Patent Application Publication No. 2003/0153082. Briefly, cell can be cultured in the presence of hematogenic cytokines such as stem cell factor (SCF), interleukin 3 (IL-3), interleukin 6 (IL-6), granulocyte-colony-stimulating factor (G-CSF)—either alone, or in combination with bone morphogenic proteins such as BMP-2, BMP-4, or BMP-7. Typically, at least two, three, or more than three such factors are combined to create a differentiation cocktail. In one example, embryoid bodies are cultured for 10 days, and then plated in an environment containing 100-300 ng/ml of both SCF and Flt-3L, 10-50 ng/ml of IL-3, IL-6, and G-CSF, 100 ng/ml SHH, and 5-100 ng/ml BMP-4-all in a medium containing 20% fetal calf serum or in serum-free medium containing albumin, transferring and insulin. After 8 to 15 days, hematopoietic cells can be evaluated for CD45+ and CD34+ expression. In another example, the cytokines and BMP-4 can be added to the culture the next day after embryoid body formation, which can further enhance the proportion of CD45+ cells after 15 to 22 days. The presence of BMP-4 can allow the user to obtain populations in which 4, 10, or more secondary CFUs form from each primary CFU, which indicate the presence of self-renewing hematopoietic progenitors.

Dendritic Cells

Stem cells of the invention may also be cultured under conditions which form dendritic cells. Such cells may be useful in vaccinations against cancer by genetically altering the cells to express a cancer antigen such as telomerase reverse transcriptase (TERT). The vaccine may then be administered to a subject having a cancer or at increased risk of developing such a cancer. Exemplary differentiation procedures are described in U.S. Patent Application Publication 2006/0063255. Thus, differentiation can be initiated in a non-specific manner by forming embryoid bodies or culturing with one or more non-specific differentiation factors. Embryoid bodies (EBs) can be made in suspension culture. Undifferentiated stem cells can be harvested by brief collagenase digestion, dissociated into clusters or strips of cells, and passaged to non-adherent cell culture plates. The aggregates can be fed every few days, and then harvested after a suitable period, typically 4-8 days. Specific recipes for making EB cells from stem cells of are found in U.S. Pat. No. 6,602,711, WO 01/51616, and U.S. Patent Application Publication Nos. 2003/0175954 and 2003/0153082. Alternatively, fairly uniform populations of more mature cells can be generated on a solid substrate; see, e.g., U.S. Patent Application Publication Nos. 2002/019046.

In one example, the cells can be first differentiated into an intermediate cell (either as an isolated cell type or in situ) that has features of multipotent hematopoietic precursor cells (e.g., CD34+CD45+CD38− and the ability to form colonies in a classic CFU assay). This can be accomplished by culturing with hematopoietic factors such as interleukin 3 (IL-3), BMP-4, optionally in combination with factors such SCF, Flt-3L, G-CSF, other bone morphogenic factors, or monocytes conditioned medium. The medium used can be any compatible medium (e.g., X-VIVO™ 15 expansion medium (Biowhittaker/Cambrex), and Aim V (Invitrogen/Gibco)). See also WO 98/30679 and U.S. Pat. No. 5,405,772. In addition or as a substitute for some of these factors, hematopoietic differentiation can be promoted by co-culturing with a stromal cell lineage (e.g., mouse lines OP9 or Ac-6, commercially available human mesenchymal stem cells, or the hES derived mesenchymal cell line HEF1 (U.S. Pat. No. 6,642,048)), or by culturing medium preconditioned in stromal cells culture.

The hematopoietic intermediate can be further differentiated into antigen presenting cells or dendritic cells that may have one or more of the following features in any combination: CD40+, CD80+, CD83+, CD86+, Class II MHC+, highly Class I MHC+, CD14−, CCR5+, and CCR7+. This can be accomplished by culturing with factors such as GM-CSF, IL-4, or IL-13, a pro-inflammatory cytokine such as TNFα or IL-6, and interferon gamma (IFNγ).

Another approach directs stem cells towards the phagocytic or dendritic cell subset early on. Intermediate cells may already bear hallmarks of monocytes ontologically related to dendritic cells or phagocytic antigen presenting cells, and may have markers such as cell surface F4/80 and Dec205, or secreted IL-12. They need not have the capability of making other types of hematopoietic cells. They are made by using IL-3 and/or stromal cell conditioned medium as before, but the GM-CSF is present in the culture concurrently.

Maturation of the phagocytic or dendritic cell precursor is achieved in a subsequent step: potentially withdrawing the IL-3, but maintaining the GM-CSF, and adding IL-4 (or IL-13) and a pro-inflammatory cytokine. Other factors that may be use include IL-1β, IFNγ, prostaglandins (e.g., PGE2), and transforming growth factor beta (TGFβ); along with TNFα and/or IL-6. A more mature population of dendritic cells can emerge.

In either the above methods, it may be beneficial to mature the cells further by culturing with a ligand or antibody that is a CD40 agonist (U.S. Pat. Nos. 6,171,795 and 6,284,742), or a ligand for a Toll-like receptor (such as LPS, a TLR4 ligand; poly I:C, a synthetic analog of double stranded RNA, which is a ligand for TLR3; Loxoribine, which a ligand for TLR7; or CpG oligonucleotides, synthetic oligonucleotides that contain unmethylated CpG dinucleotides in motif contexts, which are ligands for TLR9), either as a separate step (shown by the open arrows), or concurrently with other maturation factors (e.g., TNFα and/or IL-6).

In some embodiments, the cells are divided into two populations: one of which is used to form mature dendritic cells that are immunostimulatory, and the other of which is used to form toleragenic dendritic cells. The toleragenic cells may be relatively immature cells that are CD80−, CD86−, and/or ICAM-1−. They may also be adapted to enhance their toleragenic properties (e.g., transfected to express Fas ligand, or inactivated by irradiation or treatment with mitomycin c).

Functional studies described below can be carried out to characterize the committed progeny.

Albumin Secretion

Human albumin concentrations can be determined using an ELISA. Concentrations of albumin can be determined by generating standard curves from known concentrations of human albumin. Peroxidase-conjugated and affinity-purified anti-human albumin and reference human albumin can be obtained from Brigham and Women's Hospital Laboratory. To verify specificity of results, conditioned medium from endothelial differentiations and unconditioned hepatocyte differentiation medium can be used.

Urea Secretion

Urea secretion can be assessed by colorimetric assay (DIUR-500 BioAssay Systems) per the manufacturer's instructions. Conditioned medium from endothelial differentiations and unconditioned hepatocyte differentiation medium can be used as negative controls.

Periodic Acid-Schiff Staining

Slides can be oxidized for 5 minutes in 1% periodic acid-Schiff (PAS) (Sigma-Aldrich) and rinsed several times with double-distilled H2O (ddH2O). Samples can be incubated with Schiff's reagent for 15 minutes, rinsed several times with ddH2O, immediately counterstained with hematoxylin for 1 minute, and washed several times with ddH2O.

The observations made in this example demonstrate that the adult synovial fluid contains a sub-population of stem cells and that with the appropriate stimuli, these cells can function as mesodermal, ectodermal, or endodermal cell types.

Example 6

Isolation of Proliferative Stem Cells with a Lenti-Oct-4 GFP Vector

Figure 6:
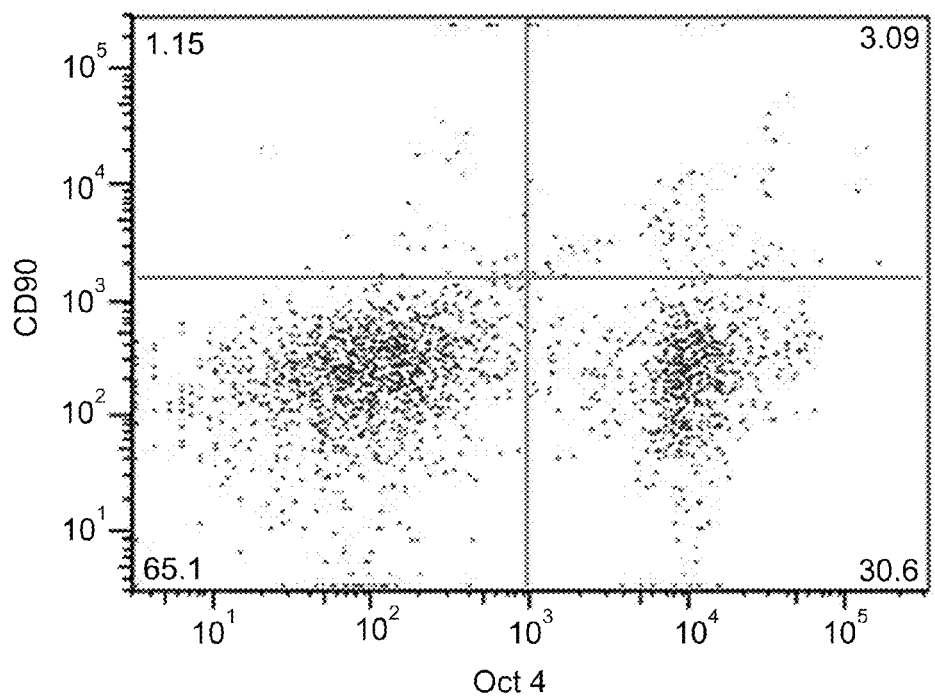
FIG. 6 shows a slide dot plot of the Oct-4 intercellular staining.

FACs analysis of the ELA Stem Cells™, performed according to the methods described in Example 2, reveals varying levels of intracellular Oct-4 protein expression (FIG. 6). An additional enrichment scheme involves the use of a vector to isolate a proliferative stem cell of the invention. The vector comprises a stem cell-specific promoter coupled to a heterologous nucleic acid sequence encoding at least one selectable marker gene, which enables isolation of the desired stem cell.

Figure 7C:
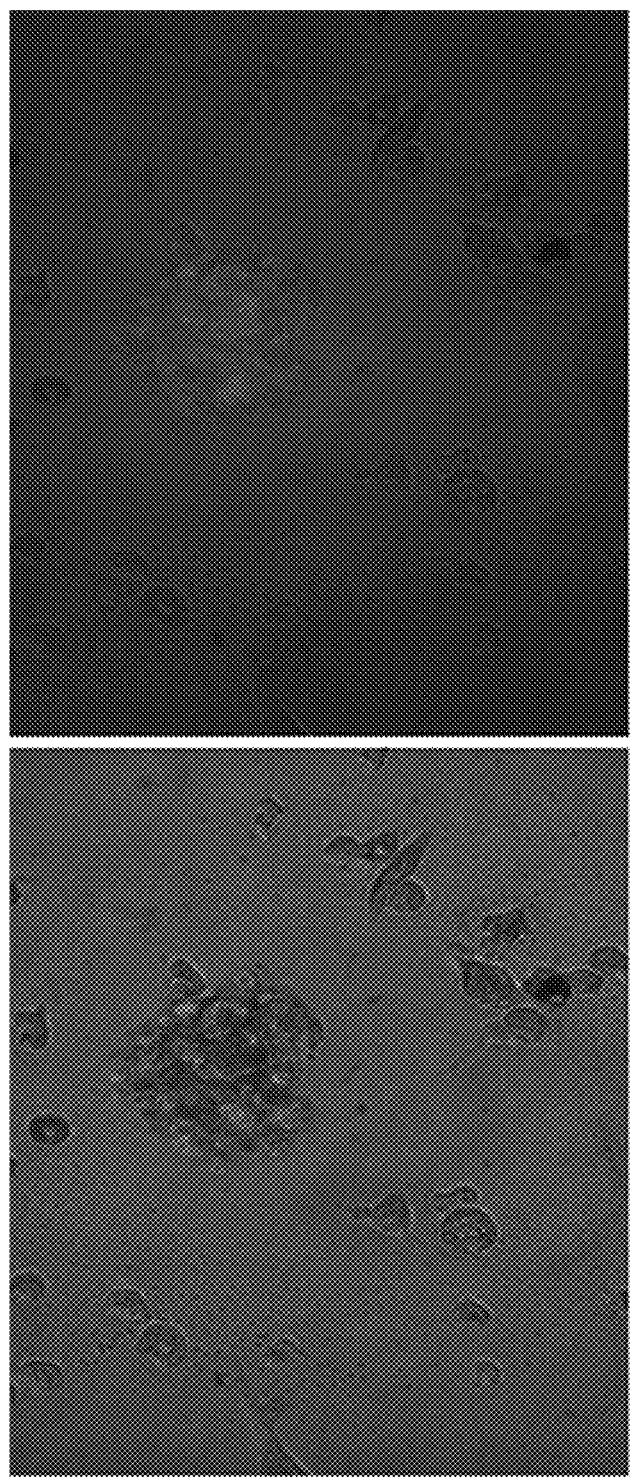
Figure 7D:
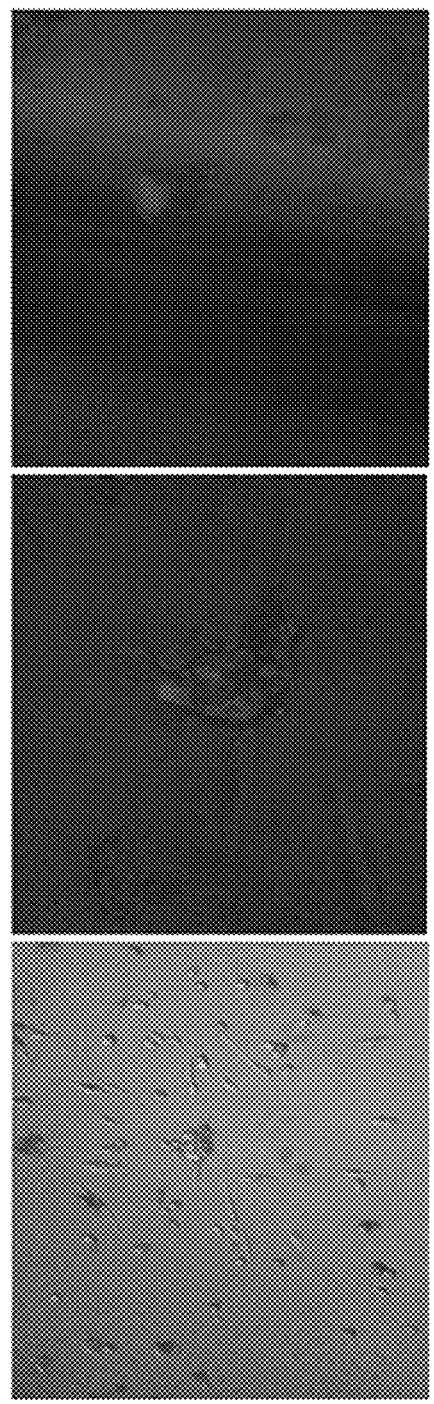

After separation from synovial fluid as described in Example 1, the pelleted mononuclear population of stem cells were resuspended to $10^5$ per ml and placed in 6-well tissue culture plastic. Lenti-Oct-4-GFP was added to the suspension and cultured for three days (FIG. 7a), four days (FIG. 7b), and nine days (FIG. 7c). The GFP-expressing cells were subsequently sorted into individual wells by flow cytometry. FIG. 6 shows a slide dot plot of the Oct-4 intracellular stain of the pelleted population of stem cells. 30% of the freshly isolated synovial fluid stem cells are Oct-4$^+$ but in most samples, Oct-4 is expressed in 5%-6% of the stem cells.

Vector Design

Figure 8A:
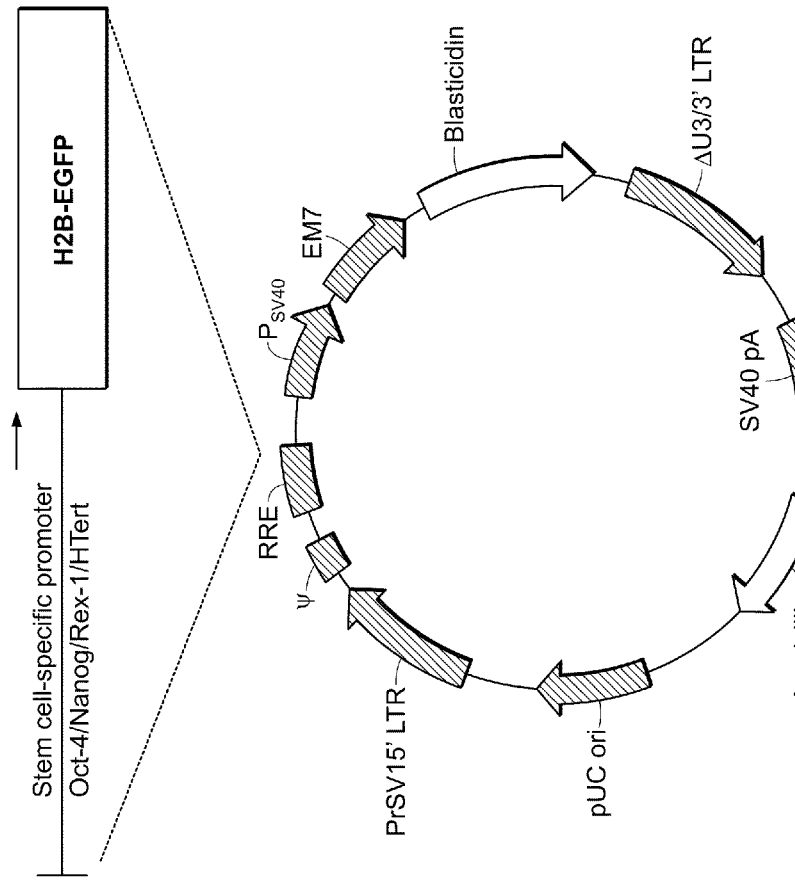
FIGS. 8a-8c are maps of the lentiviral vector for the stem cell expression.
Figure 8B:
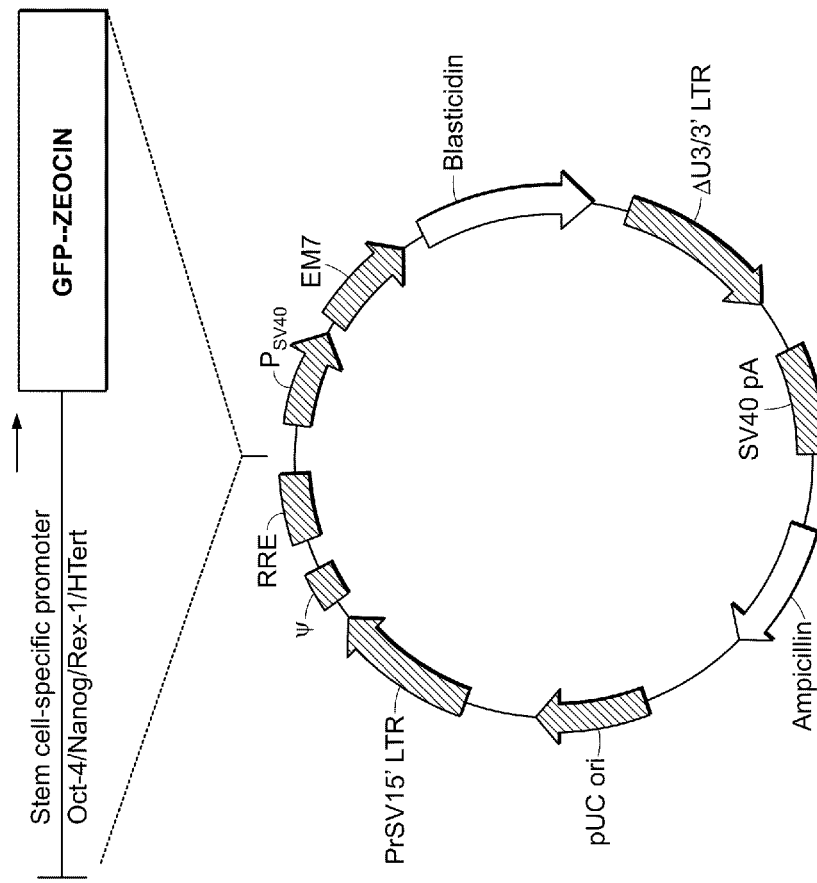
Figure 8C:
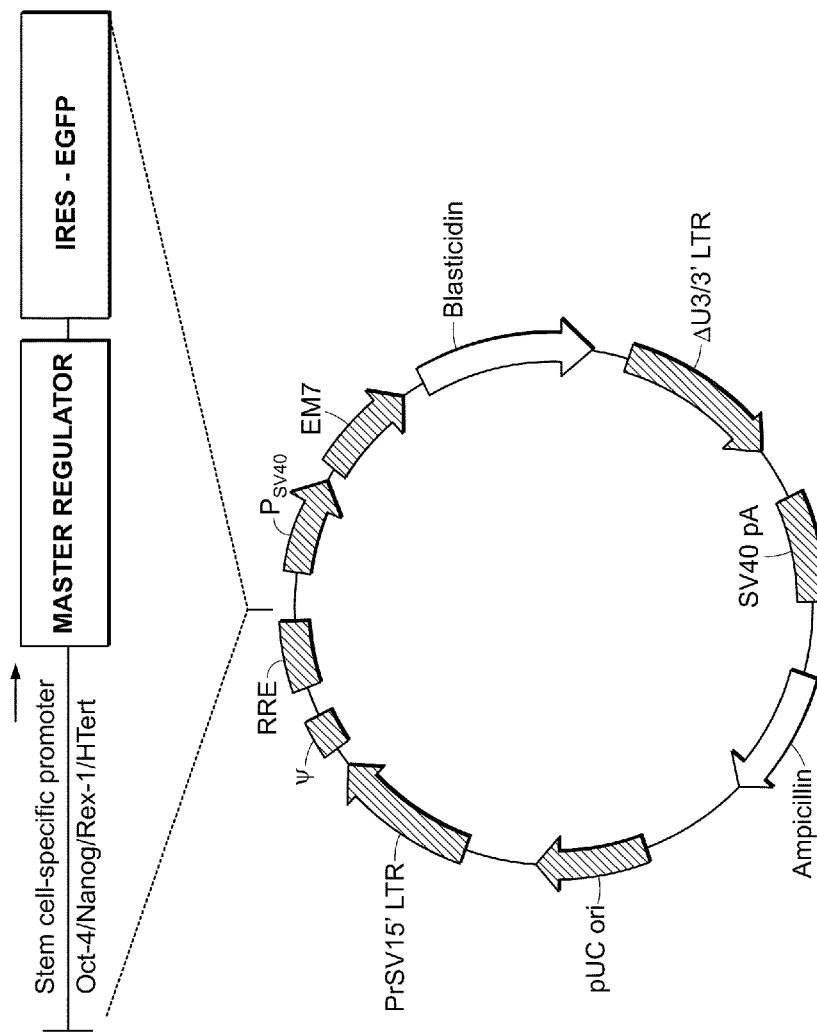

FIGS. 8a-8c show a vector map of an exemplary lentiviral vector for use in the invention. The lentiviral vector shown in panel a is used for the stem cell specific expression of H2B-EGFP in stem cells. The lentiviral vector in panel b is used for the stem cell specific expression of GFP-ZEOCIN in stem cells. In certain embodiments of the invention, the vector may be used for the stem-cell specific expression of a master regulator gene, for example as shown in FIG. 6c, where the lentiviral vector is constructed for the stem-cell specific expression of IRES EGFP in stem cells.

Figure 9A:
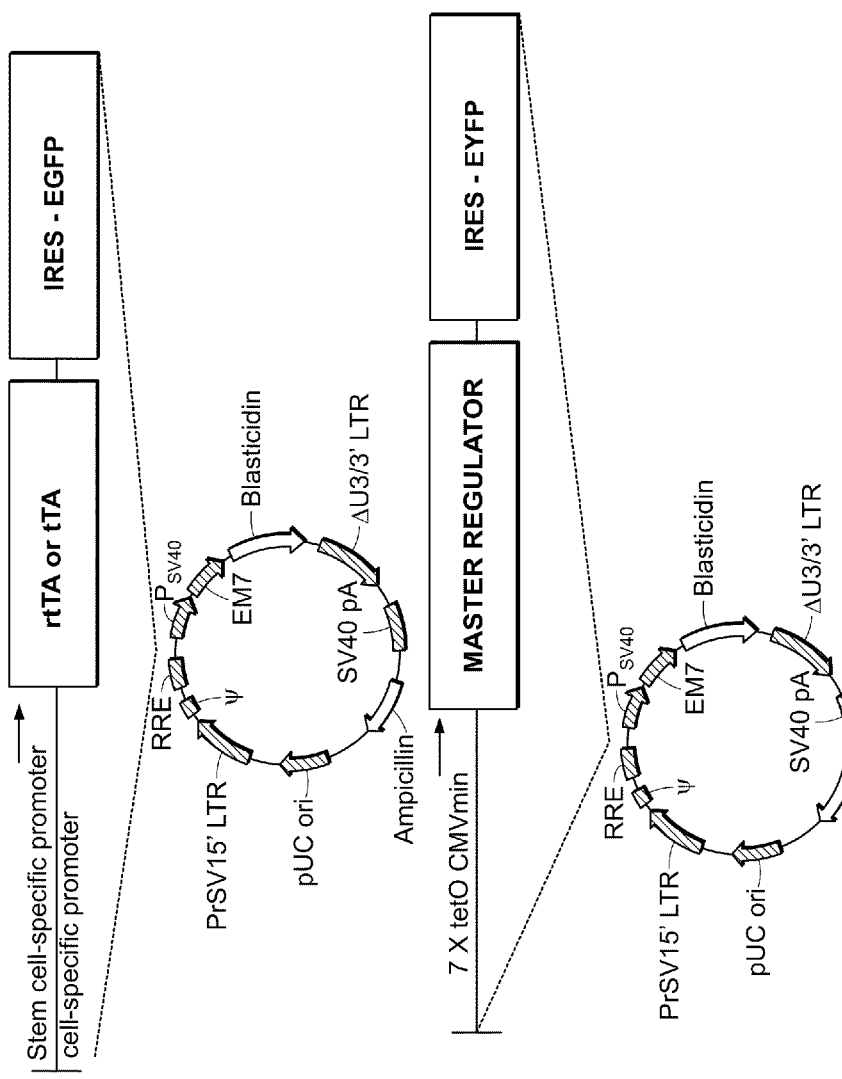
FIGS. 9a and 9b show co-transducible lentiviral vectors.
Figure 9B:
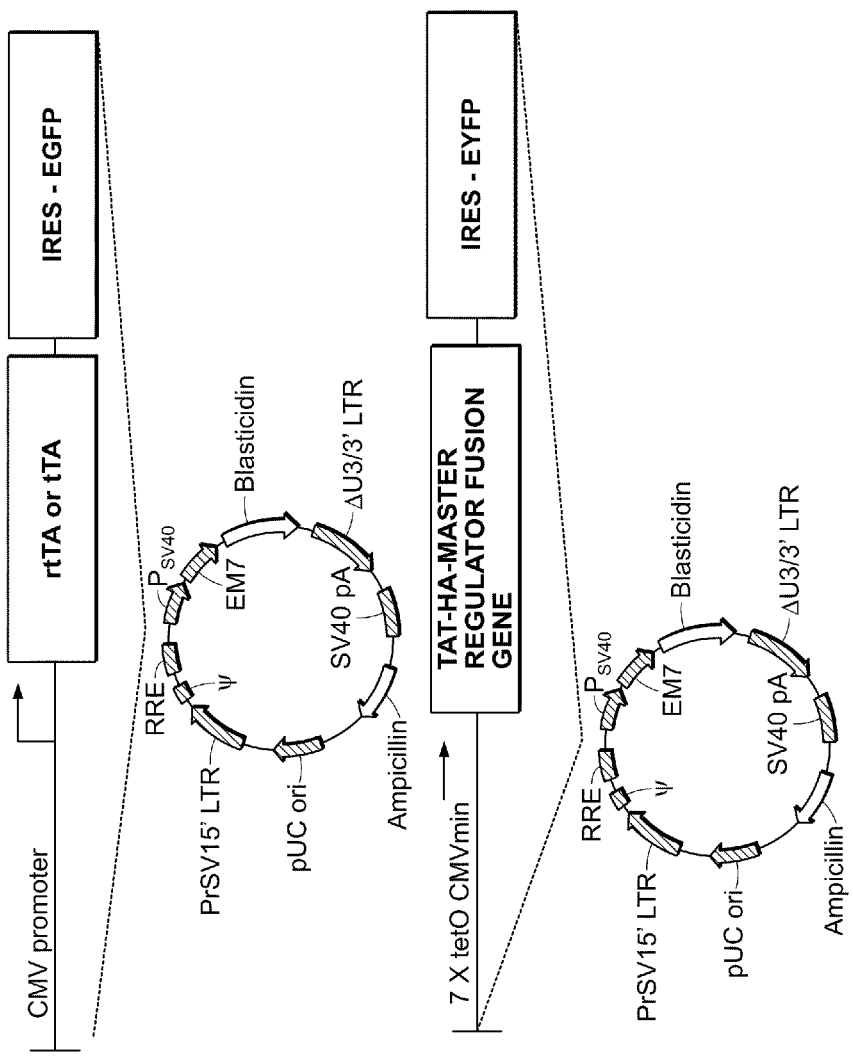

In other embodiments of the invention, co-transducible viral vectors are desirable for the tetracycline-inducible and stem/lineage progenitor cell-specific expression of a master regulator gene, for example CDX4 and/or one of the HOX genes, and IRES EGFP in stem cells. FIGS. 9a and 9b show a cotransducible lentiviral vector that is suitable for use according to this embodiment.

Transduction and Selection

Figure 10A:
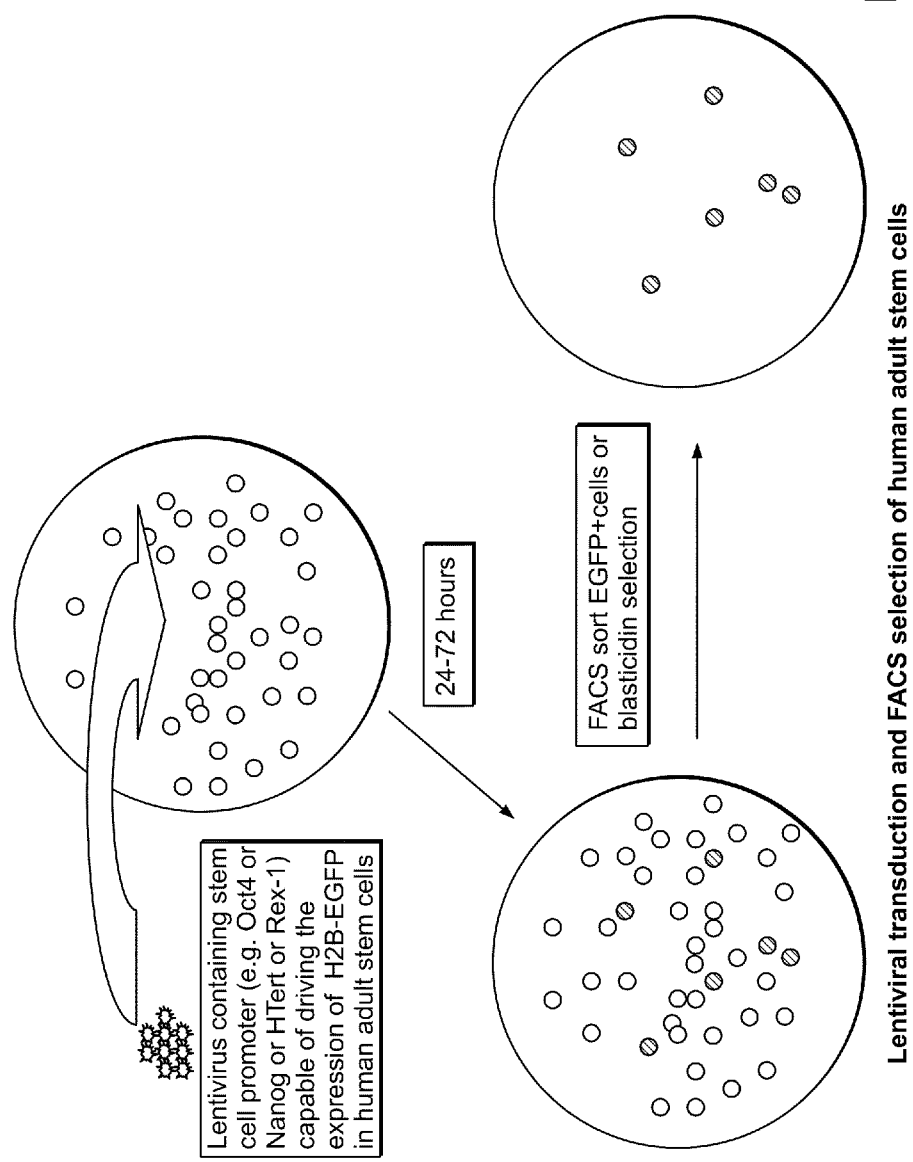
Figure 10C:
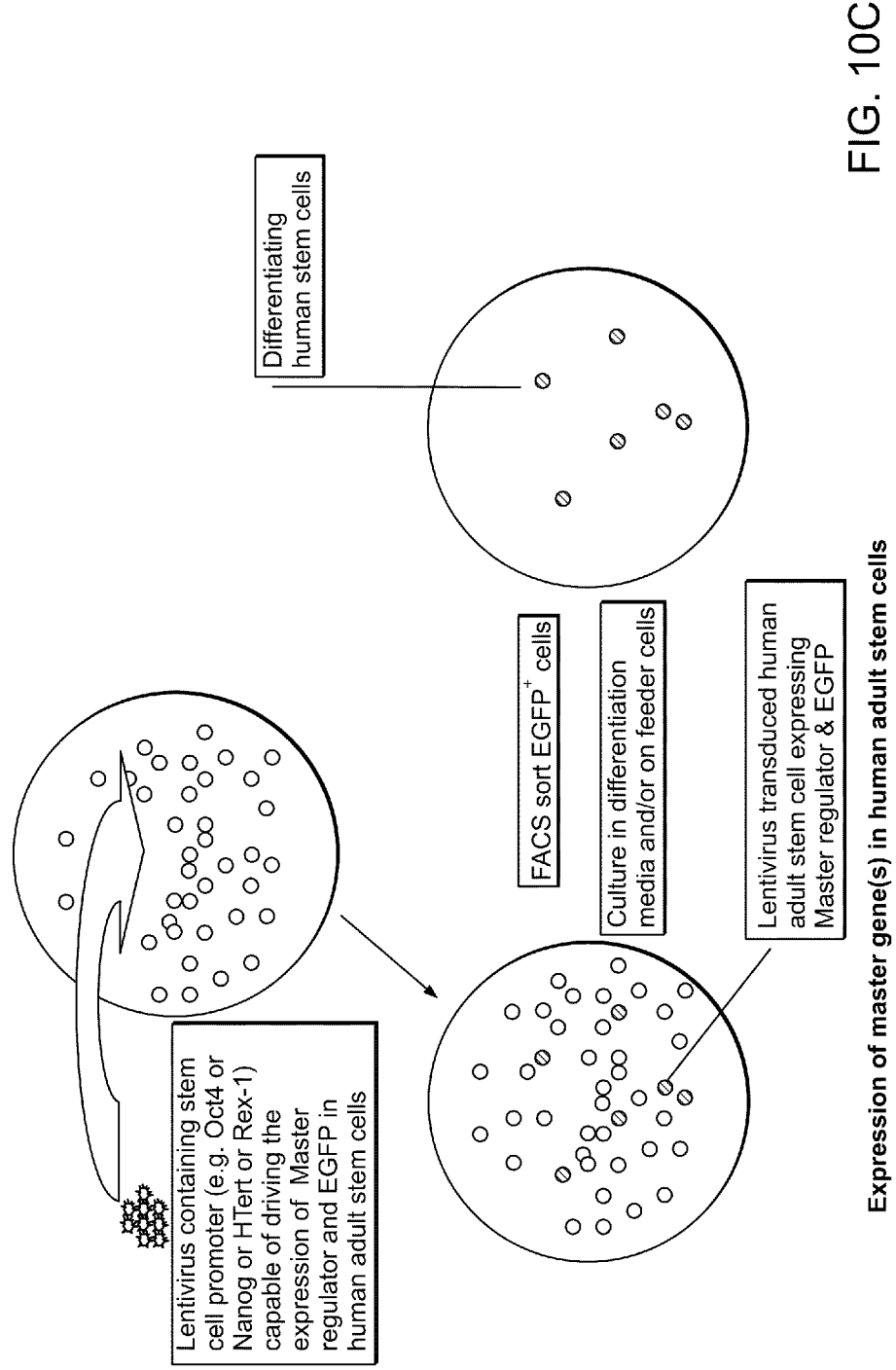
Figure 11A:
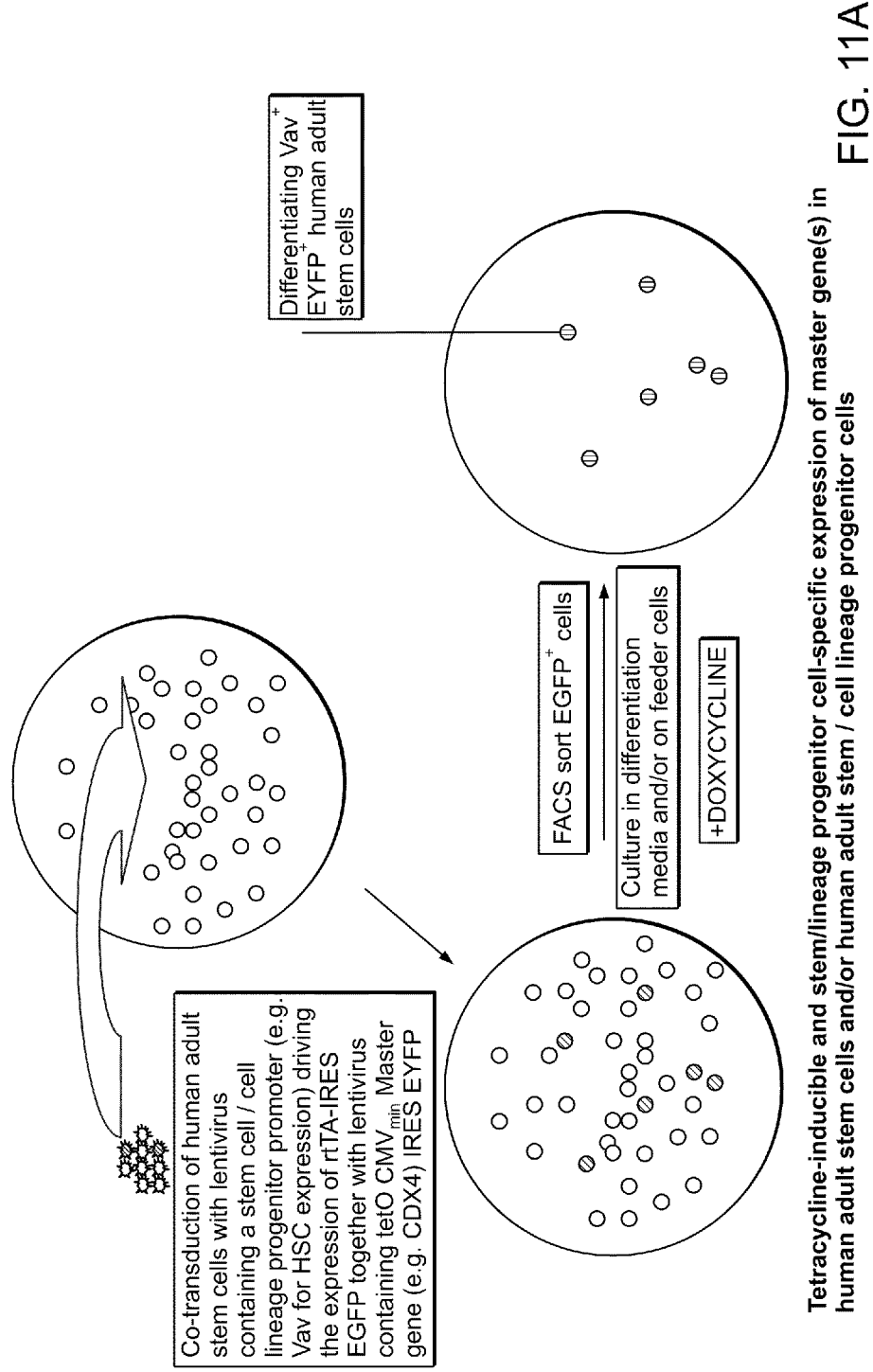
FIGS. 11a and 11b show tetracycline-inducible and stem/lineage progenitor cell-specific expression of master gene(s) (FIG. 11a) or TAT-HA-master gene (FIG. 11b) constructs in human adult stem cells and/or human adult stem/cell lineage progenitor cells and co-culture with human adult stem cells.
Figure 11B:
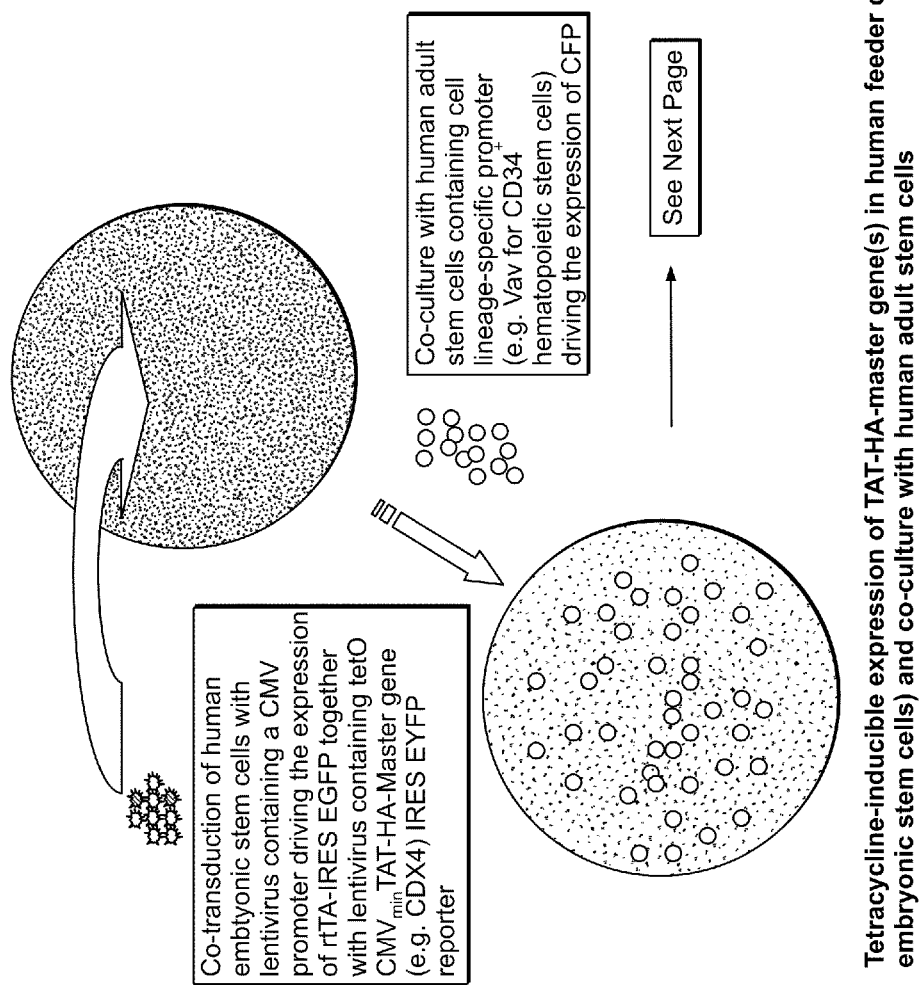
Figure 11B:
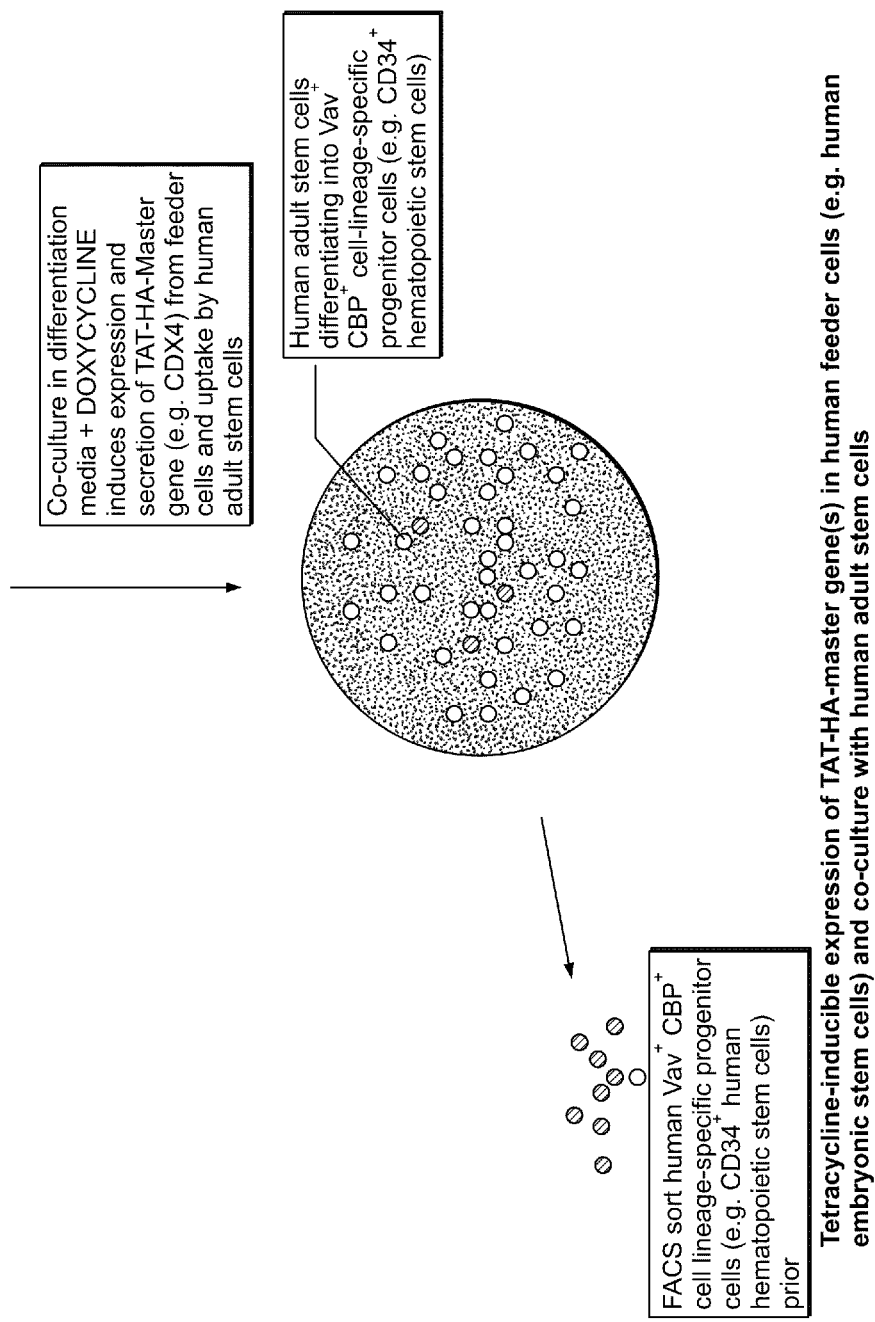
Figure 12A:
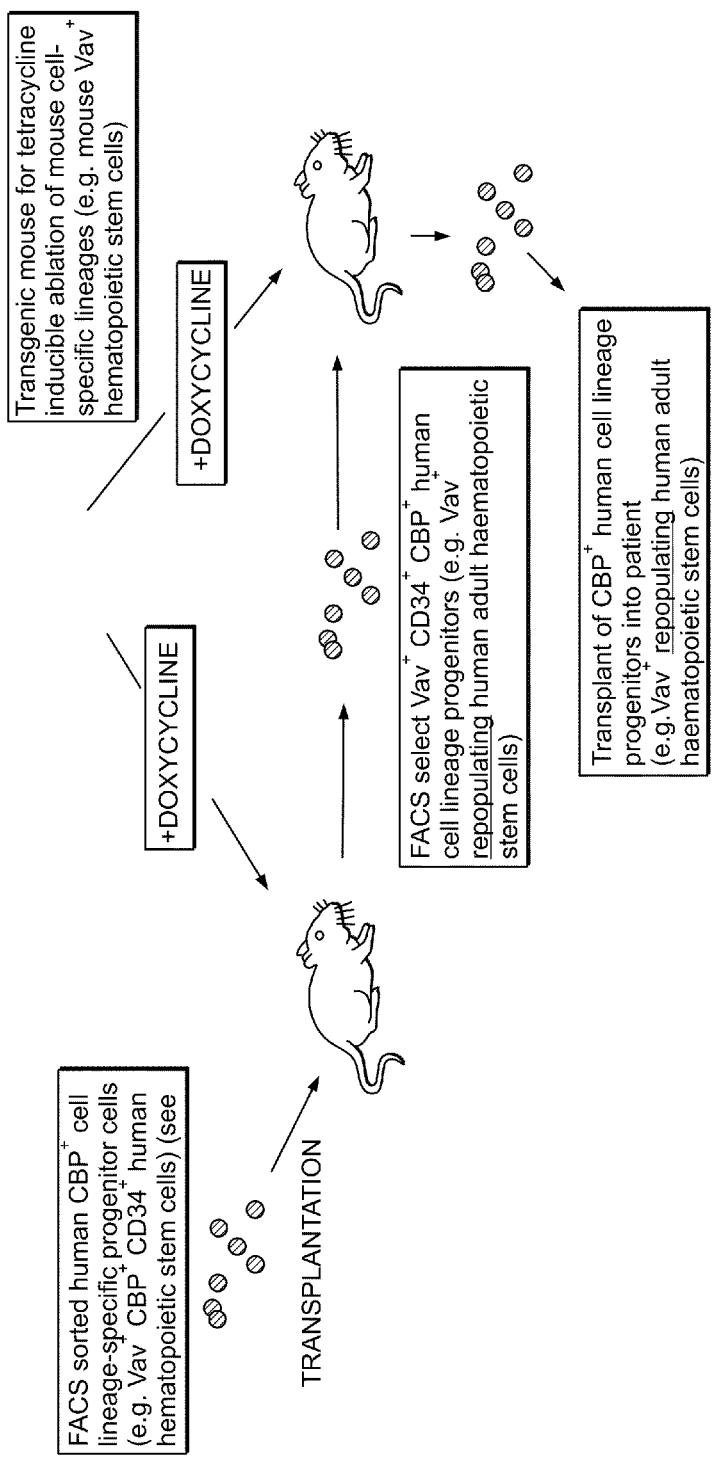
FIGS. 12a and 12b shows schema for the generation of transgenic mice.
Figure 12B:
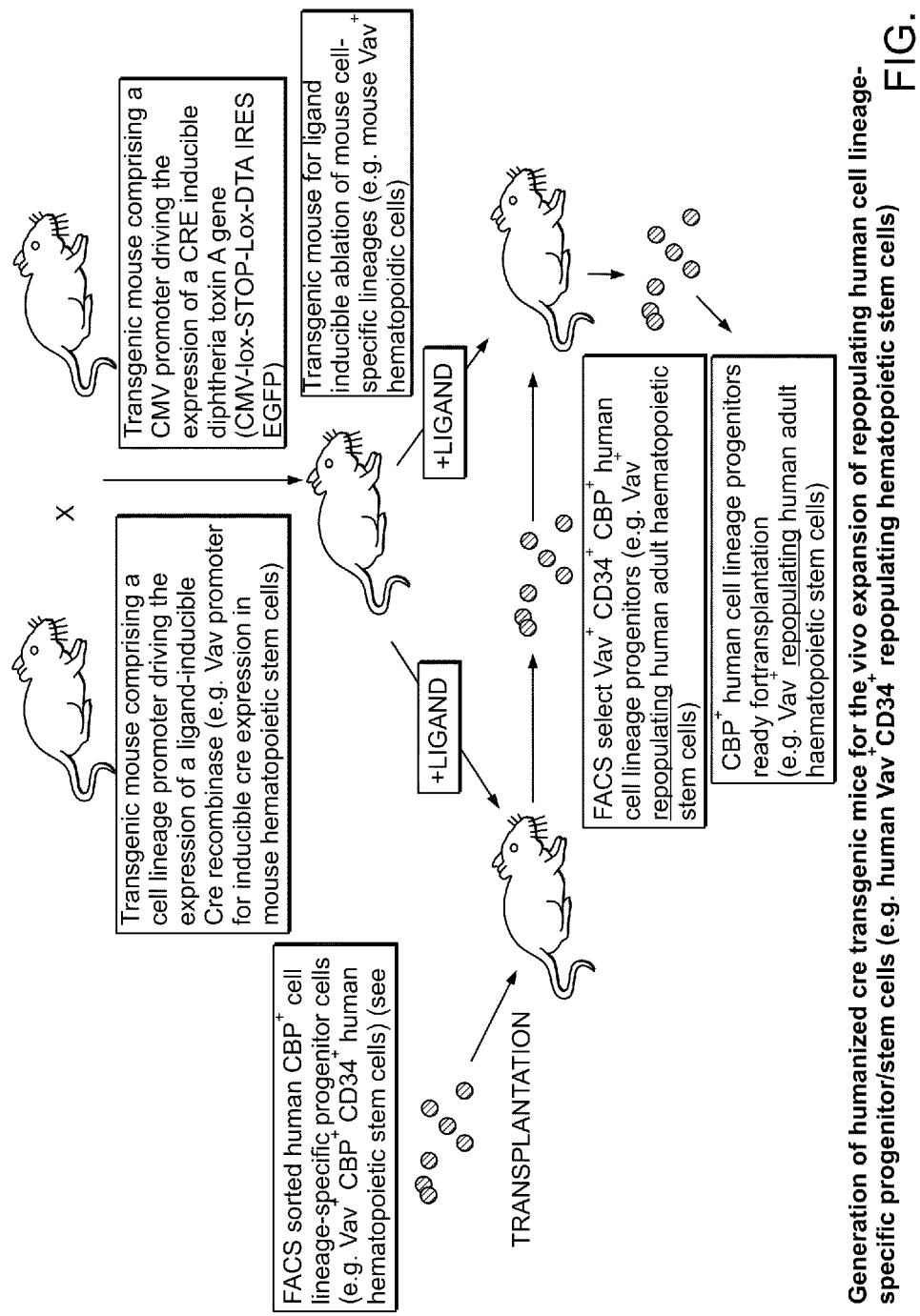

FIGS. 10a and 10b show schematics of lentiviral constructs containing a stem cell-specific promoter, for example Oct-4, Nanog, HTert, Rex, that is capable of driving the expression of a marker such as H2B-EGFP or GFP in stem cells. Following transduction with the lentivirus, the cells the of the invention are left in culture for 24-72 hours. At this time, selection is carried out. A number of methods are useful for selection, dependent upon the construction of the vector. For instance, FACS sorting can be used to sort EGFP$^+$ cells. Alternatively, blasticidin or Zeocin selection can be used when appropriate. Accordingly, following selection those transduced cells expressing H2B-EGFP will be sorted and selected. FIG. 11a shows the same experimental procedure, using a lentiviral vector that expresses a master regulator gene, for example CDX4 or a HOX gene. FIG. 11b shows cotransduction of a lentiviral vector that uses a stem cell promoter driving the expression of a tetracycline (TA)-IRES-EGFP together with a lentiviral vector containing tetracycline (tetO) linked to CMV promoter (CMVmin) and a master gene. The experiments can also be applied in vivo. FIG. 12a shows the generation of humanized rTtA transgenic mice for the in vivo expansion of repopulating human cell lineage-specific progenitor/stem cells. Transgenic mice comprising rTtA that is knocked in downstream of a cell lineage promoter, for example Vav promoter, for expression in mouse stem cells. These mice are crossed with transgenic mice comprising tetracycline responsive promoter driving the expression of diphtheria toxin, for example tetO-CMVmin-DTA. This cross produces a transgenic mouse for tetracycline ablation of mouse cell-specific lineages. Addition of doxycycline allows for selection of tetracycline-resistant cells. FIG. 12b shows the generation of humanized rTtA transgenic mice for the in vivo expansion of repopulating human cell lineage-specific progenitor/stem cells (e.g. human CD34$^+$ repopulating hematopoietic stem cells).

Lentiviral transduction can be carried out using the VIRAPOWER T-REX Lentiviral Expression System, a product of Invitrogen (full product information available on the world wide web at invitrogen.com/content/sfs/manuals/virapower_trex_lenti_man.pdf). The VIRAPOWER T-REX Lentiviral Expression System is a Gateway-adapted, lentiviral destination vector for high-level, regulated expression in dividing and non-dividing mammalian cells. The VIRAPOWER Lentiviral Technology facilitates highly efficient, in vitro or in vivo delivery of a target gene or RNA to dividing and non-dividing mammalian cells using a replication-incompetent lentivirus. The TREX Technology facilitates tetracycline-regulated expression of a gene of interest in mammalian cells through the use of regulatory elements from the E. coli Tn10-encoded tetracycline (Tet) resistance operon (Hillen and Berens, Annu. Rev. Microbiol. 48, 345-369, 1994; Hillen et al., J. Mol. Biol. 169, 707-721, 1983). Tetracycline regulation in the T-REX System is based on the binding of tetracycline to the Tet repressor and derepression of the promoter controlling expression of the gene of interest (Yao et al., Hum. Gene Ther. 9, 1939-1950, 1998). When the inducible expression construct and the regulatory expression construct are present in the same mammalian cell, expression of the gene of interest is repressed in the absence of tetracycline and induced in its presence (Yao et al., as above). GATEWAY Technology is a universal cloning method that takes advantage of the site-specific recombination properties of bacteriophage lambda (Landy, 1989) to provide a rapid and highly efficient way to move the DNA sequence of interest into multiple vector systems. The expression system contains the gene of interest under the control of a tetracycline-regulatable, hybrid CMV/TO promoter. This expression plasmid contains elements that allow packaging of the construct into virions and the ZEOCIN resistance marker for selection of stably transduced cell lines. The system includes an expression plasmid that constitutively expresses high levels of the tetracycline (Tet) repressor under the control of a CMV promoter. This expression plasmid also contains elements that allow packaging of the construct into virions and the Blasticidin resistance marker for selection of stably transduced VIRAPOWER T-REX cell lines.

Example 7

ELA Stem Cell™ Lack Many Markers Characteristic of Most Stem Cells and Differentiated Cells Stem cell surface markers are used to distinguish different types of mesenchymal stem cells (FIG. 13). Cell surface proteins common to adult stem cells are not expressed in ELA Stem Cell™. In particular, CXCR4 and CD133 are not present at detectable levels on ELA Stem Cell™.

Figure 14A:
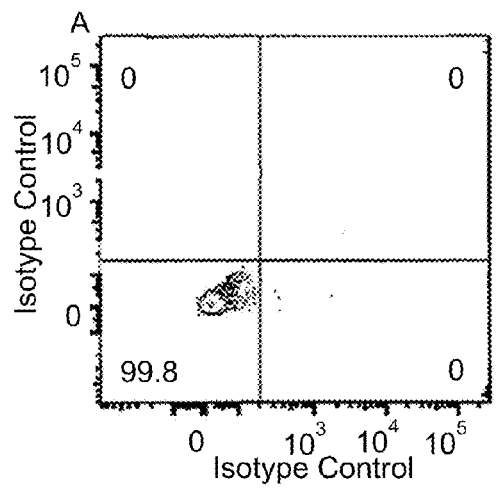
FIG. 14 is a FACS analysis that shows that the ELA Stem Cell™ is distinct from terminally differentiated cells from various tissues because it lacks the expression of lineage specific markers (Lin$^+$) (e.g. Class I, CD45) (Panel B). In addition, the ELA Stem Cell™ lacks the expression of the classical adult stem cell surface makers CD49e, CXCR-4, SSEA-4 and CD133. This indicates that the ELA Stem Cell™ is phenotypically distinct from MSCs, MIAMI cells, MAPCs, and VSEL cells.
Figure 14B:
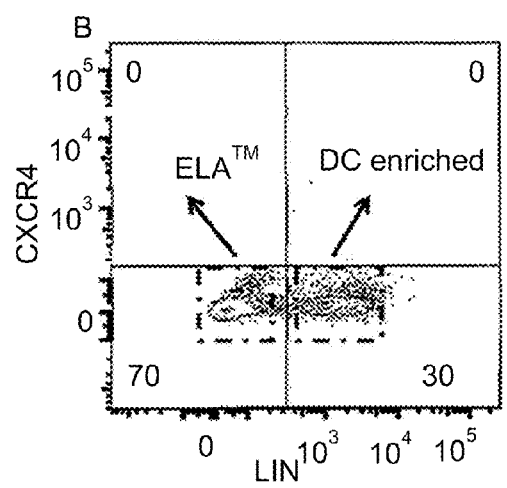
Figure 14C:
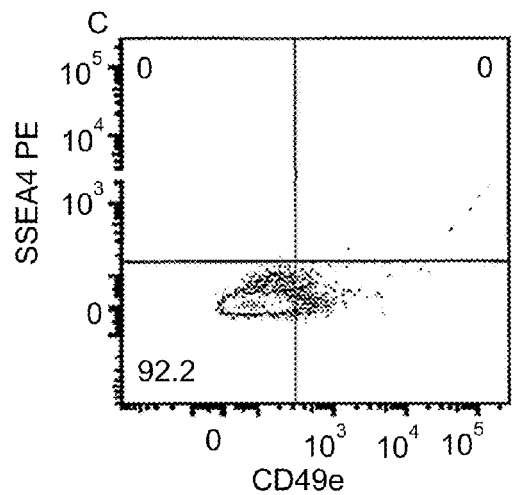
Figure 14D:
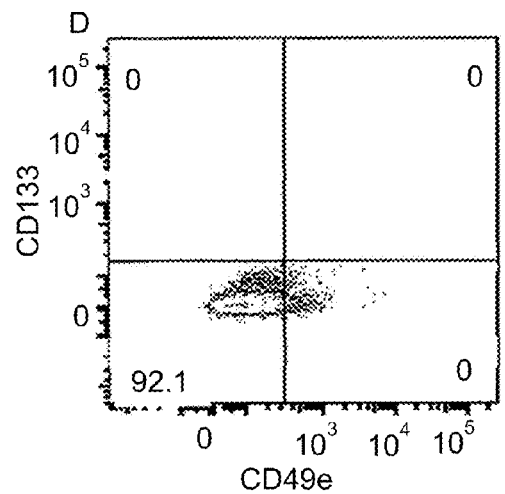
Figure 17:
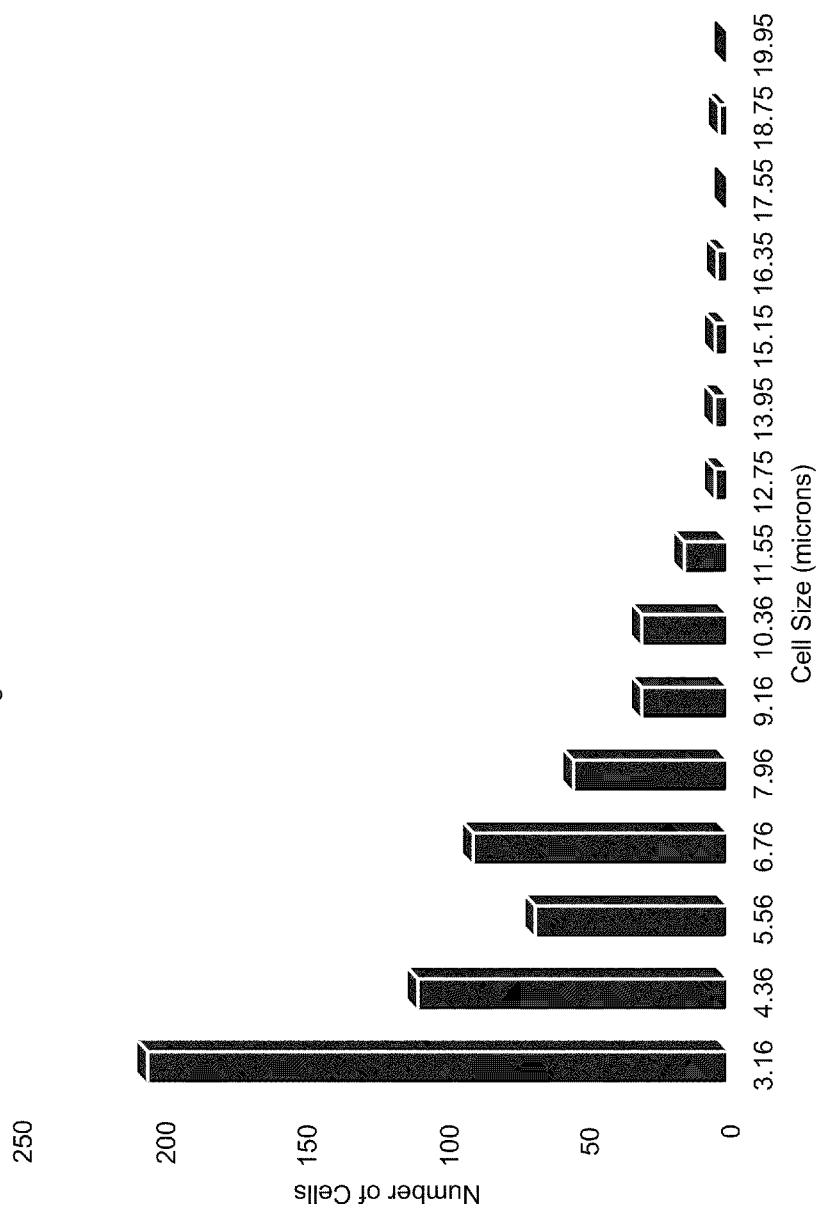
FIG. 17 shows the results from a sample of 629 cells that were taken from a population 1.69 million cells/ml. More specifically, in this case, the number of cells isolated from a single aspiration totaled 8.45 million cells. By gross inspection of the small sample of 629 cells, there was not evidence of red blood cells contamination. Cells were viewed by phase contrast and sizes from 2 microns to 20 microns were counted. The bulk of cells range in size from 3.16 to 11.55, representing 90% of the population.

ELA Stem Cell™ does not express detectable levels of Lin+, which is a marker characteristic of terminally differentiated cells (FIG. 14B). In addition, the ELA Stem Cell™ lacks the expression of the classical adult stem cell surface makers CD49e, CXCR-4, SSEA-4 and CD133 (FIGS. 14A, B, C). ELA Stem Cell viewed by phase contrast ranged in size from 2 microns to 20 microns. Ninety percent of cells range in size from 3.16 to 11.55 microns (FIG. 17).

Example 8

ELA Stem Cell™ Alter Natural Killer Cell Function

Figure 15:
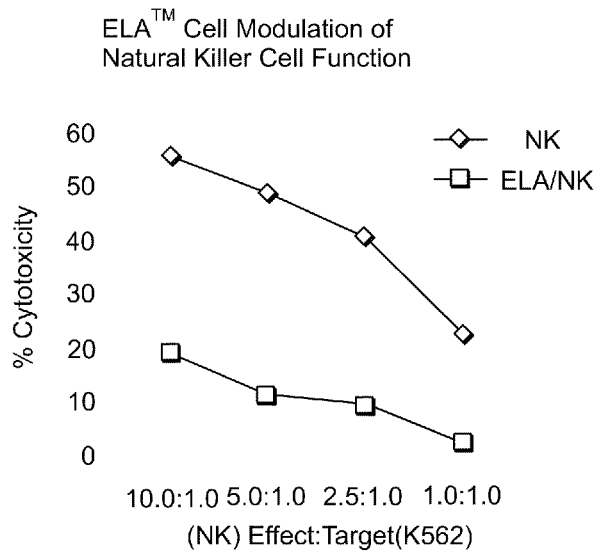
FIG. 15 shows the ELA Stem Cell™ modulation of natural killer cell functionality. Natural Killer cells induce the death of K562 cell-lines. When NK cells were precultured with ELA cells, sorted, and subsequently cultured with K562 cells, the capacity of the NK to kill the target cell decreased dramatically. Therefore, it is likely that the ELA Stem Cell™ interferes with NK cell's capacity to kill target cells.

Natural Killer cells induce the death of K562 cell-lines. Natural Killer cells pre-cultured with ELA Stem Cell™ cells showed a reduced ability to kill target cells. Based on these results it is likely that the ELA Stem Cell™ interferes with NK cell's capacity to kill target cells (FIG. 15).

Example 9

ELA Stem Cell™ Alter T Cell Function

Figure 16:
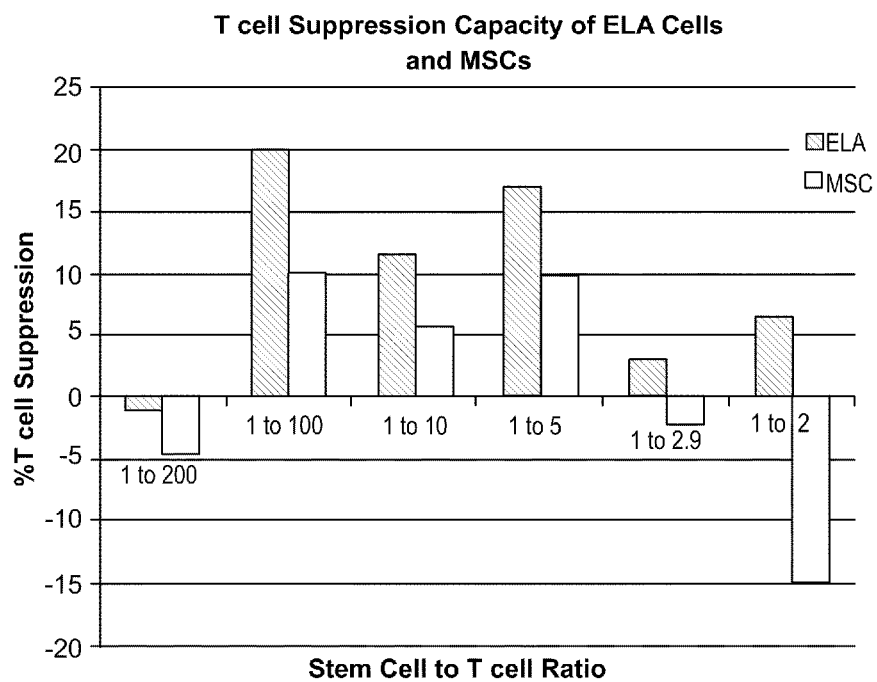
FIG. 16 shows the T cell suppression capacity of the cells of the invention in comparison to the T cell suppression capacity of mesenchymal stem cells. CD4 T cells, cultured in the presence of anti-CD3 and anti-CD28 monoclonal antibodies, undergo pan-activation. This monoclonal antibody-induced pan-activation of CD4 is suppressed when CD4$^+$ T cells are co-cultured with either ELA Stem Cells™ or MSCs. The ELA Stem Cells™ and MSCs demonstrated optimum T cell suppression at 1 to 10 ratios of adult stem cells to T cells. Note that the ELA cell more efficiently suppressed T cell function than MSCs at any concentration. More importantly, this data suggests that at high concentrations, MSCs begin to enhance T cell activation.

CD4 T cells, cultured in the presence of anti-CD3 and anti-CD28 monoclonal antibodies, undergo pan-activation. This monoclonal antibody-induced pan-activation of CD4 was suppressed when CD4$^+$ T cells were co-cultured with either ELA Stem Cells™ or MSCs (FIG. 16). The ELA Stem Cell™ more efficiently suppressed T cell function than MSCs at any concentration.

Those skilled in the art will recognize, or be able to determine using no more than routine experimentation, variations on the foregoing examples that will permit them to identify many other stem cells than the ones described herein.

Other Embodiments

All patents, patent applications, and publications mentioned in this specification including U.S. Provisional Application No. 60/927,596, filed May 3, 2007 are herein incorporated by reference to the same extent as if each independent patent, patent application, or publication was specifically and individually indicated to be incorporated by reference.

Incorporation by Reference

The entire contents of all patents published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. An isolated human adult stem cell that is capable of proliferating and differentiating into at least two of ectoderm, mesoderm, or endoderm, expresses at least one of Oct-4, KLF-4, Nanog, Sox-2, Rex-1, GDF-3, and Stella, and does not detectibly express CD13, CD45, CD90, and CD34 and further does not detectibly express at least one of MHC class I, MHC class II, CD44, CD49c, CD73, CD66A, CD66E, CXCR4, CD133 or an SSEA.

2. An isolated quiescent human adult stem cell that is capable of proliferating and differentiating into at least two of ectoderm, mesoderm, and endoderm and does not detectibly express Oct-4, CD13, CD45, CD90, CD34 and further does not detectibly express at least one of MHC class I, MHC class II, CD44, CD49c, CD73, CD66A, CD66E, CXCR4, CD133 or an SSEA.

3. The cell of claim 1, wherein the SSEA is SSEA-4.

4. The cell of claim 1, wherein said cell is synovial fluid derived, blood derived or tissue derived.

5. The cell of claim 1, wherein said cell is substantially purified.

6. The cell of claim 1, further comprising a heterologous nucleic acid sequence.

7. A population of isolated human adult stem cells that are capable of proliferating and differentiating into at least two of ectoderm, mesoderm, and endoderm, express at least one of Oct-4, KLF-4, Nanog, Sox-2, Rex-1, GDF-3, and Stella, and does not detectibly express CD13, CD45, CD90, CD34 and further does not detectibly express at least one of MHC class I, MHC class II, CD44, CD49c, CD73, CD66A, CD66E, CXCR4, CD133 or an SSEA, wherein from about 10% to about 30% of the population of human adult stem cells are quiescent.

8. The population of claim 7, wherein said population is a culture expanded population.

9. The population of claim 7, wherein said cells are cryopreserved and wherein said population is included within a container.

10. The population of claim 9, wherein said container is a vial, syringe or other container suitable for local delivery into a site within a human.

11. The population of claim 9, wherein said container is a bag or other container suitable for intravenous delivery of cells within a human.

12. The population of claim 7, wherein said population comprises said stem cells in an amount of at least $1\times10^3$, at least $1\times10^6$, at least $1\times10^9$, at least $1\times10^{12}$, or at least $1\times10^{14}$.

13. The population of claim 7, wherein said population is contained in a 0.9% NaCl solution.

14. The population of claim 7, further comprising a bioactive compound.

15. The population of claim 7, wherein said bioactive compound is a growth factor, a cytokine, an antibody or fragment thereof, or an organic molecule, the molecule having a mass of less than 5,000 daltons.

16. A master cell bank comprising a plurality of cryopreserved individually packaged populations of isolated human adult stem cells, each population including at least $1\times10^2$ or more of the cells of claim 1.

17. A population of human stem cells obtained by expanding the population of claim 7.

18. The population of human stem cells as recited in claim 8, wherein expanding the population comprises passaging the population of human stem cells at least three times.

19. The isolated human adult stem cell of claim 1 that further does not detectably express CD105.

* * * * *